US012576277B2

(12) United States Patent
Beatty et al.

(10) Patent No.: US 12,576,277 B2
(45) Date of Patent: Mar. 17, 2026

(54) ADVANCED PACING

(71) Applicant: Maxwell Biomedical, Inc., San Diego, CA (US)

(72) Inventors: Graydon Beatty, San Diego, CA (US); Walter Botongo Bomela, El Cajon, CA (US); Benjamin Anthony Coppola, Carlsbad, CA (US); Timothy J. Corvi, San Diego, CA (US); Randell L. Werneth, San Diego, CA (US); Janice Shima Barstad, Chaska, MN (US); Stephen Wood, National City, CA (US); Hector Augusto Velasco Perez, San Diego, CA (US); R. Maxwell Flaherty, Topsfield, MA (US); J. Christopher Flaherty, Nottingham, NH (US)

(73) Assignee: MAXWELL BIOMEDICAL, INC., San Diego, CA (US)

( * ) Notice: Subject to any disclaimer, the term of this patent is extended or adjusted under 35 U.S.C. 154(b) by 0 days.

(21) Appl. No.: 18/976,825

(22) Filed: Dec. 11, 2024

(65) Prior Publication Data

US 2025/0108220 A1     Apr. 3, 2025

Related U.S. Application Data

(63) Continuation of application No. PCT/US2023/027740, filed on Jul. 14, 2023.
(Continued)

(51) Int. Cl.
*A61N 1/36* (2006.01)
*A61N 1/05* (2006.01)
(Continued)

(52) U.S. Cl.
CPC .......... *A61N 1/365* (2013.01); *A61N 1/0587* (2013.01); *A61N 1/3624* (2013.01)

(58) Field of Classification Search
CPC ..... A61N 1/365; A61N 1/0587; A61N 1/3624
See application file for complete search history.

(56) References Cited

U.S. PATENT DOCUMENTS 4,388,927 A     6/1983   Schober
4,612,940 A     9/1986   Kasevich et al.
(Continued)

FOREIGN PATENT DOCUMENTS

CN     104767291     7/2015
CN     110446529     11/2019
(Continued)

OTHER PUBLICATIONS

Abiri et al., "Inductively powered wireless pacing via a miniature pacemaker and remote stimulation control system", Science Reports, vol. 7, No. 6180, Jul. 21, 2017. pp. 1-10, doi: 10.1038/s41598-017-06493-5.
(Continued)

*Primary Examiner* — Rex R Holmes
(74) *Attorney, Agent, or Firm* — Onello & Mello P.C.

(57) ABSTRACT

Systems, devices, and methods for providing therapy to a heart of a patient are disclosed. The system includes an implantable device to be implanted proximate the heart of the patient. The implantable device includes at least one sensing electrode configured to sense electrical activity of the heart, at least two pacing electrodes configured to deliver electrical stimulation energy to tissue of the heart, and a controller including one or more algorithms. The one or more algorithms are executable to determine a pacing strategy to terminate atrial fibrillation.

20 Claims, 25 Drawing Sheets

Related U.S. Application Data

(60) Provisional application No. 63/453,570, filed on Mar. 21, 2023, provisional application No. 63/389,094, filed on Jul. 14, 2022.

(51) Int. Cl.

| | |
|---|---|
| *A61N 1/362* | (2006.01) |
| *A61N 1/365* | (2006.01) |

(56) References Cited

U.S. PATENT DOCUMENTS

| | | | |
|---|---|---|---|
| 4,719,919 A | 1/1988 | Marchosky et al. |
| 5,464,429 A | 11/1995 | Hedberg et al. |
| 5,522,865 A | 6/1996 | Schulman et al. |
| 5,630,426 A | 5/1997 | Eggers et al. |
| 5,749,909 A | 5/1998 | Schroeppel et al. |
| 5,785,660 A | 7/1998 | van Lake et al. |
| 6,148,230 A | 11/2000 | KenKnight |
| 6,402,689 B1 | 6/2002 | Scarantino et al. |
| 6,423,056 B1 | 7/2002 | Ishikawa et al. |
| 6,735,472 B2 | 5/2004 | Helland |
| 6,813,518 B2 | 11/2004 | Bernhard |
| 6,870,503 B2 | 3/2005 | Mohamadi |
| 6,882,315 B2 | 4/2005 | Richley et al. |
| 7,010,340 B2 | 3/2006 | Scarantino et al. |
| 7,043,301 B1 | 5/2006 | Kroll et al. |
| 7,132,173 B2 | 11/2006 | Daulton |
| 7,177,341 B2 | 2/2007 | McCorkle |
| 7,228,228 B2 | 6/2007 | Bartlett et al. |
| 7,339,883 B2 | 3/2008 | Santhoff et al. |
| 7,532,933 B2 | 5/2009 | Hastings et al. |
| 7,610,092 B2 | 10/2009 | Cowan et al. |
| 7,751,881 B2 | 7/2010 | Cowan et al. |
| 8,032,227 B2 | 10/2011 | Parramon et al. |
| 8,126,418 B2 | 2/2012 | Nowak et al. |
| 8,188,841 B2 | 5/2012 | Dowla et al. |
| 8,290,600 B2 | 10/2012 | Hastings et al. |
| 8,547,248 B2 | 10/2013 | Zdeblick et al. |
| 8,552,597 B2 | 10/2013 | Song et al. |
| 8,634,919 B1 | 1/2014 | Hou et al. |
| 8,644,933 B2 | 2/2014 | Ozawa et al. |
| 8,670,824 B2 | 3/2014 | Anderson et al. |
| 8,939,928 B2 | 1/2015 | Savoie et al. |
| 9,026,212 B2 | 5/2015 | Imran |
| 9,031,658 B2 | 5/2015 | Chiao et al. |
| 9,037,223 B2 | 5/2015 | Oral et al. |
| 9,153,642 B2 | 10/2015 | Li et al. |
| 9,161,693 B2 | 10/2015 | Rizwan |
| 9,168,380 B1 | 10/2015 | Greenhut et al. |
| 9,168,383 B2 | 10/2015 | Jacobson et al. |
| 9,205,258 B2 | 12/2015 | Simon et al. |
| 9,270,137 B2 | 2/2016 | Greene |
| 9,277,874 B2 | 3/2016 | Joshi et al. |
| 9,421,369 B2 | 8/2016 | Liu et al. |
| 9,423,438 B2 | 8/2016 | Lin et al. |
| 9,486,621 B2 | 11/2016 | Howard et al. |
| 9,522,270 B2 | 12/2016 | Perryman et al. |
| 9,544,068 B2 | 1/2017 | Arbabian et al. |
| 9,669,223 B2 | 6/2017 | Auricchio et al. |
| 9,669,230 B2 | 6/2017 | Koop |
| 9,685,793 B2 | 6/2017 | Zargham et al. |
| 9,700,712 B2 | 7/2017 | Towe |
| 9,711,978 B2 | 7/2017 | Manova-Elssibony et al. |
| 9,953,195 B2 | 4/2018 | Turner et al. |
| 10,014,730 B2 | 7/2018 | Nayak |
| 10,238,872 B2 | 3/2019 | Pivonka et al. |
| 10,312,743 B2 | 6/2019 | Ouda et al. |
| 10,369,369 B2 | 8/2019 | Perryman et al. |
| 10,493,288 B2 | 12/2019 | Hastings et al. |
| 10,530,421 B2 | 1/2020 | Muthali et al. |
| 10,537,403 B2 | 1/2020 | Vora et al. |
| 10,742,222 B2 | 8/2020 | Emira et al. |
| 10,806,932 B2 | 10/2020 | Koop et al. |
| 10,978,917 B2 | 4/2021 | Freitas et al. |
| 11,048,893 B2 | 6/2021 | Babakhani et al. |
| 11,050,263 B2 | 6/2021 | Bae et al. |
| 11,058,880 B2 | 7/2021 | Yang et al. |
| 11,071,857 B2 | 7/2021 | Sun et al. |
| 11,515,733 B2 | 11/2022 | Babakhani et al. |
| 2002/0064245 A1 | 5/2002 | McCorkle |
| 2002/0103507 A1 | 8/2002 | Helland |
| 2002/0137991 A1 | 9/2002 | Scarantino et al. |
| 2003/0032986 A1 | 2/2003 | Kuepper |
| 2003/0229379 A1 | 12/2003 | Ramsey |
| 2004/0054471 A1 | 3/2004 | Bartlett et al. |
| 2004/0058186 A1 | 3/2004 | Daulton |
| 2004/0095287 A1 | 5/2004 | Mohamadi |
| 2004/0108954 A1 | 6/2004 | Richley et al. |
| 2005/0058121 A1 | 3/2005 | Santhoff et al. |
| 2005/0256549 A1 | 11/2005 | Holzer |
| 2006/0085039 A1 | 4/2006 | Hastings et al. |
| 2006/0136004 A1 | 6/2006 | Cowan et al. |
| 2007/0043416 A1 | 2/2007 | Callas et al. |
| 2007/0118187 A1 | 5/2007 | Denker et al. |
| 2007/0120677 A1 | 5/2007 | Park et al. |
| 2007/0293895 A1 | 12/2007 | Cowan et al. |
| 2008/0021505 A1 | 1/2008 | Hastings et al. |
| 2008/0039904 A1 | 2/2008 | Bulkes et al. |
| 2008/0252422 A1 | 10/2008 | Dowla et al. |
| 2008/0262580 A1 | 10/2008 | Gerber et al. |
| 2008/0300660 A1 | 12/2008 | John |
| 2008/0306359 A1 | 12/2008 | Zdeblick et al. |
| 2009/0157141 A1 | 6/2009 | Chiao et al. |
| 2009/0219139 A1 | 9/2009 | Slesinski |
| 2009/0292341 A1 | 11/2009 | Parramon et al. |
| 2010/0076517 A1 | 3/2010 | Imran |
| 2010/0114243 A1 | 5/2010 | Nowak et al. |
| 2011/0022025 A1 | 1/2011 | Savoie et al. |
| 2011/0034912 A1 | 2/2011 | De Graff et al. |
| 2011/0288615 A1 | 11/2011 | Armstrong et al. |
| 2012/0008714 A1 | 1/2012 | Rizwan |
| 2012/0109236 A1 | 5/2012 | Jacobson et al. |
| 2012/0239118 A1 | 9/2012 | Ozawa et al. |
| 2012/0256492 A1 | 10/2012 | Song et al. |
| 2013/0041235 A1 | 2/2013 | Rogers et al. |
| 2013/0066400 A1 | 3/2013 | Perryman et al. |
| 2013/0109987 A1 | 5/2013 | Kunis et al. |
| 2013/0123882 A1 | 5/2013 | Towe |
| 2013/0197380 A1 | 8/2013 | Oral et al. |
| 2014/0046389 A1 | 2/2014 | Anderson et al. |
| 2014/0058239 A1 | 2/2014 | Joshi et al. |
| 2014/0198062 A1 | 7/2014 | Kreutzer et al. |
| 2014/0243848 A1 | 8/2014 | Auricchio et al. |
| 2014/0252543 A1 | 9/2014 | Li et al. |
| 2014/0336474 A1 | 11/2014 | Arbabian et al. |
| 2014/0375261 A1 | 12/2014 | Manova-Elssibony et al. |
| 2015/0042358 A1 | 2/2015 | Lin et al. |
| 2015/0076920 A1 | 3/2015 | Zargham et al. |
| 2015/0127068 A1 | 5/2015 | Simon et al. |
| 2015/0217123 A1 | 8/2015 | Deterre et al. |
| 2015/0229139 A1 | 8/2015 | Greene |
| 2015/0297900 A1 | 10/2015 | Perryman et al. |
| 2015/0343205 A1 | 12/2015 | Howard et al. |
| 2015/0356332 A1 | 12/2015 | Turner et al. |
| 2016/0008602 A1 | 1/2016 | Perryman et al. |
| 2016/0030743 A1* | 2/2016 | Kaiser ............... A61N 1/36514 607/14 |
| 2016/0038739 A1 | 2/2016 | Liu et al. |
| 2016/0048710 A1 | 2/2016 | Nekoogar et al. |
| 2016/0149441 A1 | 5/2016 | Nayak |
| 2016/0228718 A1 | 8/2016 | Koop |
| 2016/0338798 A1 | 11/2016 | Vora et al. |
| 2017/0001003 A1 | 1/2017 | Pivonka et al. |
| 2018/0069486 A1 | 3/2018 | Ouda et al. |
| 2018/0071539 A1 | 3/2018 | Hastings et al. |
| 2018/0123639 A1 | 5/2018 | Muthali et al. |
| 2018/0140850 A1 | 5/2018 | Linder et al. |
| 2018/0177431 A1 | 6/2018 | Rottenberg |
| 2018/0235692 A1 | 8/2018 | Efimov et al. |
| 2018/0264270 A1 | 9/2018 | Koop et al. |
| 2019/0097430 A1 | 3/2019 | Bae et al. |
| 2019/0180065 A1 | 6/2019 | Babakhani et al. |
| 2019/0224476 A1 | 7/2019 | Sun et al. |
| 2019/0247050 A1 | 8/2019 | Goldsmith |

(56) References Cited

U.S. PATENT DOCUMENTS

| | | | |
|---|---|---|---|
| 2019/0247664 A1 | 8/2019 | Irazoqui et al. | |
| 2019/0262605 A1 | 8/2019 | Babakhani et al. | |
| 2019/0290905 A1 | 9/2019 | Yang et al. | |
| 2019/0326785 A1 | 10/2019 | Freitas et al. | |
| 2020/0022607 A1 | 1/2020 | Pratt et al. | |
| 2020/0155828 A1 | 5/2020 | Shepard et al. | |
| 2020/0195256 A1 | 6/2020 | Emira et al. | |
| 2021/0339017 A1 | 11/2021 | Sun et al. | |
| 2021/0356417 A1 | 11/2021 | Babakhani et al. | |
| 2021/0397257 A1 | 12/2021 | Rogers et al. | |
| 2022/0032067 A1* | 2/2022 | Kornet | A61B 5/361 |
| 2022/0158497 A1 | 5/2022 | Babakhani et al. | |
| 2022/0252506 A1 | 8/2022 | Babakhani et al. | |
| 2022/0264196 A1 | 8/2022 | Lyu et al. | |
| 2022/0273944 A1 | 9/2022 | Werneth et al. | |
| 2023/0181910 A1 | 6/2023 | Werneth | |
| 2025/0161691 A1 | 5/2025 | Werneth et al. | |

FOREIGN PATENT DOCUMENTS

| | | |
|---|---|---|
| CN | 113228464 | 8/2021 |
| EP | 3884562 | 9/2021 |
| JP | 2022507813 | 1/2022 |
| WO | 9627327 | 9/1996 |
| WO | 0038783 | 7/2000 |
| WO | 2007028035 | 3/2007 |
| WO | 2007109656 | 9/2007 |
| WO | 2013058958 | 4/2013 |
| WO | 2016199142 | 12/2016 |
| WO | 2017066121 | 4/2017 |
| WO | 2017070322 | 4/2017 |
| WO | 2017205565 | 11/2017 |
| WO | 2018039162 | 3/2018 |
| WO | 2018053467 | 3/2018 |
| WO | 2020106440 | 5/2020 |
| WO | 2020106862 | 5/2020 |
| WO | 2020125839 | 6/2020 |
| WO | 2021007071 | 1/2021 |
| WO | 2021007210 | 1/2021 |
| WO | 2021046313 | 3/2021 |
| WO | 2021055146 | 3/2021 |
| WO | 2021174215 | 9/2021 |
| WO | 2021183487 | 9/2021 |
| WO | 2021247490 | 12/2021 |
| WO | 2022133501 | 6/2022 |
| WO | 2024015555 | 1/2024 |

OTHER PUBLICATIONS

Agarwal et al., "A 4 µW, ADPLL-Based Implantable Amperometric Biosensor in 65nm CMOS", 2017 Symposium on VLSI Circuits, Kyoto, Japan, 2017, pp. C108-C109. doi: 10.23919/VLSIC.2017.8008566.

Ahn et al., "Optimal Design of Wireless Power Transmission Links for Millimeter-Sized Biomedical Implants", IEEE Transactions on Biomedical Circuits and Systems, Jan. 20, 2015, vol. 10, Issue 1, pp. 125-137, DOI: 10.1109/TBCAS.2014.2370794.

Arfin et al., "An energy-efficient, adiabatic electrode stimulator with inductive energy recycling and feedback current regulation", IEEE Transactions on Biomedical Circuits and Systems, Feb. 2012, vol. 6, Issue 1, pp. 1-14, first published Oct. 6, 2011, DOI: 10.1109/TBCAS.2011.2166072.

Atzori et al., "The Internet of Things: A survey", Computer Networks, Oct. 2010, vol. 54, Issue 15, pp. 2787-2805, https://doi.org/10.1016/j.comnet.2010.05.010.

Bahrami et al., "Flexible, polarization-diverse UWB antennas for implantable neural recording systems", IEEE Transactions on Biomedical Circuits and Systems, vol. 10, No. 1, Feb. 2016, pp. 38-48.

Balanis, Constantine A., "Antenna Theory: Analysis and Design", John Wiley & Sons, 2016, 1095 pgs. (presented in nine parts).

Bereuter et al., "Hot Topic in Cardiac Devices—Leadless cardiac dualchamber pacing", Europace Abstracts Supplement, 2018, 1 pg. doi:10.1093/europace/euy015.

Bereuter et al., "Leadless Dual-Chamber Pacing, A Novel Communication Method for Wireless Pacemaker Synchronization", JACC: Basic to Translational Service, Dec. 2018, vol. 3, No. 6, pp. 813-823, https://doi.org/10.1016/j.jacbts.2018.07.009.

Biederman et al., "A Fully-Integrated, Miniaturized (0.125 mm²) 10.5 µW Wireless Neural Sensor", IEEE Journal of Solid-State Circuits, vol. 48, No. 4, Mar. 22, 2013, pp. 960-970, DOI: 10.1109/JSSC.2013.2238994.

Bigio et al., "Microwave absorption spectroscopy of DNA", Biopolymers, Jan. 1993, vol. 33, Issue 1, pp. 147-150, https://doi.org/10.1002/bip.360330114.

Bourdel et al., "A 9-pJ/Pulse 1.42-Vpp OOK CMOS UWB Pulse Generator for the 3.1—10.6-GHz FCC Band", IEEE Transactions on Microwave Theory and Techniques, vol. 58, No. 1, Jan. 2010, pp. 1-9.

Brown et al., "An Ultra-Low-Power 9.8 GHz Crystal-Less UWB Transceiver with Digital Baseband Integrated in 0.18 µm BiCMOS", IEEE International Solid-State Circuits Conference, 2013, pp. 442-443.

Carlson et al., "A 20 mV Input Boost Converter with Efficient Digital Control for Thermoelectric Energy Harvesting", IEEE Journal of Solid-State Circuits, vol. 45, Issue 4, Apr. 2010, pp. 741-750.

Chae et al., "A 128-Channel 6 mW Wireless Neural Recording IC With Spike Feature Extraction and UWB Transmitter", IEEE Transactions on Neural Systems and Rehabilitation Engineering, vol. 17, No. 4, Aug. 2009, pp. 312-321.

Chang et al., "27.7 A 30.5mm3 fully packaged implantable device with duplex ultrasonic data and power links achieving 95kb/s with <10-4 BER at 8.5cm depth", IEEE International Solid-State Circuits Conference (ISSCC), Feb. 5-9, 2017, pp. 460-461, DOI: 10.1109/ISSCC.2017.7870460.

Charthad et al., "A mm-sized implantable medical device (IMD) with ultrasonic power transfer and a hybrid bi-directional data link", IEEE Journal of Solid-State Circuits, vol. 50, Issue 8, Aug. 2015, pp. 1741-1753, DOI: 10.1109/JSSC.2015.2427336.

Charthad et al., "A mm-Sized Wireless Implantable Device for Electrical Stimulation of Peripheral Nerves", IEEE Transactions on Biomedical Circuits and Systems, vol. 12, No. 2, Apr. 2018, pp. 257-270, doi: 10.1109/TBCAS.2018.2799623.

Charthad et al., "System-Level Analysis of Far-Field Radio Frequency Power Delivery for mm-Sized Sensor Nodes", IEEE Transactions on Circuits and Systems I: Regular Papers, Feb. 3, 2016, vol. 63, No. 2, pp. 300-311, DOI: 10.1109/TCSI.2015.2512720.

Chen et al., "3D Radar Imaging based on a Synthetic Array of 30GHz Impulse Radiators with On-Chip Antennas in 130nm SiGe BiCMOS", IEEE Transactions on Microwave Theory and Techniques, Nov. 2017, vol. 65, No. 22, pp. 4373-4384.

Chen et al., "Multiple leadless pacemakers implanted in the right ventricle of swine", Europace, 2016, vol. 18, 1748-1752, published online Jan. 31, 2016, doi:10.1093/europace/euv418.

Cheng, "Field and wave electromagnetics", Pearson Education India, 1989, 720 pgs., (presented in three parts).

Chinitz et al., "Accelerometer-based atrioventricular synchronous pacing with a ventricular leadless pacemaker: Results from the Micra atrioventricular feasibility studies", Heart Rhythm, 2018, vol. 15, pp. 1363-1371, https://doi.org/10.1016/j.hrthm.2018.05.004.

Cogan et al., "Neural stimulation and recording electrodes", Annual Review of Biomedical Engineering, 2008, vol. 10, pp. 275-309, first published online Apr. 22, 2008, doi: 10.1146/annurev.bioeng.10.061807.160518.

Extended European Search Report dated Aug. 2, 2023 issued in European Application No. 20860681.4.

Extended European Search Report dated Jul. 19, 2022 issued in European Application No. 199887763.1.

International Preliminary Report on Patentability dated Jan. 11, 2022 issued in International Application No. PCT/US2020/040283.

International Preliminary Report on Patentability dated Jan. 11, 2022 issued in International Application No. PCT/US2020/041007.

International Preliminary Report on Patentability dated Jan. 25, 2024 issued in International Application No. PCT/US2022/036926.

International Preliminary Report on Patentability dated Mar. 15, 2022 issued in International Application No. PCT/US2020/048001.

(56)        References Cited

OTHER PUBLICATIONS

International Preliminary Report on Patentability dated May 25, 2021 issued in International Application No. PCT/US2019/062443.
International Preliminary Report on Patentability dated May 25, 2021 issued in related International Application No. PCT/US2019/059657.
International Preliminary Report on Patentability dated Sep. 22, 2022 issued in International Application No. PCT/US21/21467.
International Preliminary Report on Patentability dated Sep. 9, 2022 issued in International Application No. PCT/US2021/020343.
International Search Report and Written Opinion dated Dec. 12, 2017 issued in International Application No. PCT/US2017/052163.
International Search Report and Written Opinion dated Jan. 21, 2020 issued in International Application No. PCT/US2019/059657.
International Search Report and Written Opinion dated Jan. 29, 2020 issued in International Application No. PCT/US2019/062443.
International Search Report and Written Opinion dated Jun. 22, 2021 issued in International Application No. PCT/US2021/020343.
International Search Report and Written Opinion dated Jun. 3, 2021 issued in International Application No. PCT/US21/21467.
International Search Report and Written Opinion dated Mar. 14, 2018 issued in International Application No. PCT/US2017/047901.
International Search Report and Written Opinion dated May 3, 2022 issued in International Application No. PCT/US2021/073036.
International Search Report and Written Opinion dated Nov. 20, 2020 issued in International Application No. PCT/US2020/048001.
International Search Report and Written Opinion dated Nov. 24, 2020 issued in International Application No. PCT/US2020/049349
International Search Report and Written Opinion dated Oct. 17, 2022 issued in International Application No. PCT/US2022/036926.
International Search Report and Written Opinion dated Oct. 2, 2020 issued in International Application No. PCT/US2020/041007.
International Search Report and Written Opinion dated Oct. 4, 2021 issued in International Application No. PCT/US2021/035132.
International Search Report and Written Opinion dated Sep. 28, 2020 issued in International Application No. PCT/US2020/040283.
Dagan et al., "A low-power low-cost 24 ghz rfid tag with a c-flash based embedded memory", IEEE Journal of Solid-State Circuits, Sep. 2014, vol. 49, No. 9, pp. 1942-1957, DOI: 10.1109/JSSC.2014.2323352.
Dagdeviren et al., "Conformal piezoelectric energy harvesting and storage from motions of the heart, lung, and diaphragm", PNAS, vol. 111, No. 5, Feb. 4, 2014, published online Jan. 21, 2014, pp. 1927-1932, doi: 10.1073/pnas.1317233111.
De Roover et al., "A fully integrated wireless power supply for pinless active RFID-devices in 130nm CMOS", 2007 IEEE Asian Solid-State Circuits Conference, Nov. 12-14, 2007, pp. 123-126, DOI: 10.1109/ASSCC.2007.4425747.
Yi et al., "Analysis and design strategy of UHF micro-power CMOS rectifiers for micro-sensor and RFID applications", IEEE Transactions on Circuits and Systems I: Regular Papers, Jan. 15, 2007, vol. 54, Issue 1, pp. 153-166, DOI: 10.1109/TCSI.2006.887974.
Yu et al., "Cardiac resynchronization therapy: state of the art 2013", European Heart Journal, vol. 34, Issue 19, May 14, 2013, online published Jan. 25, 2013, pp. 1396-1403, https://doi.org/10.1093/eurheartj/ehs454.
Yvanoff et al., "A Feasibility Study of Tissue Characterization Using Implanted LC Sensors", IEEE Transactions on Antennas and Propagation, Apr. 2009, vol. 57, Issue 4, pp. 885-893, DOI: 10.1109/TAP.2009.2016073.
Zargham et al., "Fully Integrated On-Chip Coil in 0.13 μm CMOS for Wireless Power Transfer Through Biological Media", IEEE Transactions on Biomedical Circuits and Systems, Apr. 2015, vol. 9, Issue 2, pp. 259-271, DOI: 10.1109/TBCAS.2014.2328318.
Zhang et al., "A 23 μA RF-powered transmitter for biomedical applications", 2011 IEEE Radio Frequency Integrated Circuits Symposium, 4 pgs., DOI: 10.1109/RFIC.2011.5940711.
Zhang et al., "A Miniature Mode Reconfigurable Inductorless IR-UWB Transmitter—Receiver for Wireless Short-Range Com-munication and Vital-Sign Sensing", IEEE Journal of Emerging and Selected Topics in Circuits and Systems, vol. 8, No. 2, Jun. 2018, pp. 294-305.
International Search Report and Written Opinion dated Oct. 18, 2023 issued in International Application No. PCT/US2023/027740.
Deer et al., "The Appropriate Use of Neurostimulation: Avoidance and Treatment of Complications of Neurostimulation Therapies for the Treatment of Chronic Pain", Neuromodulation: Technology at the Neural Interface, Aug. 12, 2014. vol. 17, No. 6, pp. 571-598, DOI: 10.1111/ner.12206.
Derksen M.D., Richard et al., "Tissue Discontinuities Affect Con-duction Velocity Restitution, a Mechanism by Which Structural Barriers May Promote Wave Break", http://circ.ahajournals.org/content/108/7/882, Aug. 19, 2003, 8 pages, Copyright 2003 Ameri-can Heart Association, Inc.
Dickson, "On-chip high-voltage generation in MNOS integrated circuits using an improved voltage multiplier technique", IEEE Journal of Solid-State Circuits, 1976, vol. 11, No. 3, pp. 374-378, http://dx.doi.org/10.1109/JSSC.1976.1050739.
Dorta-Quinones et al., "A Wireless FSCV Monitoring IC With Analog Background Subtraction and UWB Telemetry", IEEE Trans-actions on Biomedical Circuits and Systems, vol. 10, No. 2, Apr. 2016, 36 pgs.
Dosdall et al., "Mechanisms of defibrillation", Annual Review of Biomedical Engineering, vol. 12, Aug. 15, 2010, first published as a Review in Advance May 5, 2010, pp. 233-258, https://doi.org/10.1146/annurev-bioeng-070909-105305.
Eldeeb et al., "A 0.4-V Miniature CMOS Current Mode Instrumen-tation Amplifier", IEEE Transactions on Circuits and Systems—II Express Briefs, Mar. 2018, Vo. 65, No. 3, pp. 261-265, DOI: 10.1109/TCSII.2017.2685589.
FCC, "First Report and Order 02-48", Federal Communication Commission (FCC), Feb. 2002, 118 pgs., (presented in two parts).
Fenton PhD, Flavio H. et al., Termination of Atrial Fibrillation Using Pulsed Low-Energy Far-Field Stimulation, http://circ.ahajournals.org/content/120/6/467, Aug. 11, 2009, 15 pages, Copyright 2009 American Heart Association, Inc.
Gao et al., "A 71GHZ Rf Energy Harvesting Tag with 8% Efficiency for Wireless Temperature Sensors in 65nm CMOS", IEEE Radio Frequency Integrated Circuits Symposium (RFIC), Jun. 2013, pp. 403-406, DOI: 10.1109/RFIC.2013.6569616.
Gilbert, "Impedance matching with lossy components", IEEE Trans-actions on Circuits and Systems, Feb. 1975, vol. 22, Issue: 2, pp. 96-100, DOI: 10.1109/TCS.1975.1084016.
Grenier et al., "Recent advances in microwave-based dielectric spectroscopy at the cellular level for cancer investigations", IEEE Transactions on Microwave Theory and Techniques, Apr. 11, 2013, vol. 61, No. 5, pp. 2023-2030, doi:10.1109/TMTT.2013.2255885.
Guler et al., "Power Management in Wireless Power-Sipping Devices: A Survey", IEEE Circuits and Systems Magazine, Nov. 20, 2017, pp. 64-82, DOI: 10.1109/MCAS .2017.2757090.
Gunturi et al., "A 250-Mb/s Data Rate IR-UWB Transmitter Using Current-Reused Technique", IEEE Transactions on Microwave Theory and Techniques, vol. 65, No. 11, Nov. 2017, pp. 4255-4265, DOI: 10.1109/TMTT.2017.2695189.
H. Lyu et al., "A Multi-site Heart Pacing Study Using Wirelessly Powered Leadless Pacemakers," 2018 40th Annual International Conference of the IEEE Engineering in Medicine and Biology Society (EMBC), Honolulu, HI, 2018, pp. B434-B3437, doi: 10.1109/EMBC.2018.8512977. Retrieved from Internet on Nov. 16, 2020; https://ieeexplore.eee.org/abstract/document/8512977; entire docu-ment.
Hannan et al., "Energy harvesting for the implantable biomedical devices: issues and challenges", BioMedical Engineering OnLine, 2014, vol. 13, No. 79, 23 pgs., https://doi.org/10.1186/1475-925X-13-79.
Hehn et al., "A Fully Autonomous Integrated Interface Circuit for Piezoelectric Harvesters", IEEE Journal of Solid-State Circuits, Sep. 2012, vol. 47, Issue 9, pp. 2185-2198, DOI: 10.1109/JSSC.2012.2200530.
Higgins et al., "Advances in Pacing Therapy: Examining the Poten-tial Impact of Leadless Pacing Therapy", Journal of Innovations in

(56) References Cited

OTHER PUBLICATIONS

Cardiac Rhythm Management, Nov. 2014, vol. 5, pp. 1825-1833, DOI: 10.19102/icrm.2014.051106.

Ho, John S. et al., "Wireless power transfer to deep-tissue microimplants," PNAS, Jun. 3, 2014, vol. 11, No. 22, www.pnas. org/cgi/content/short/1403002111, 12 pages.

Huang et al., "A simple subthreshold cmos voltage reference circuit with channel-length modulation compensation", IEEE Transactions on Circuits and Systems—II: Express Briefs, Sep. 2006, vol. 53, No. 9, pp. 882-885, DOI: 10.1109/TCSII.2006.881813.

Huang et al., "Materials and designs for wireless epidermal sensors of hydration and strain", Advanced Functional Materials, Jul. 2, 2014, vol. 24, Issue 25, pp. 3846-3854, first published Mar. 2, 2014, doi: 10.1002/adfm.201303886.

Huang et al., "Neurostimulation Strategy for Stress Urinary Incontinence", IEEE Transactions on Neural Systems and Rehabilitation Engineering, Jul. 2017, vol. 25, No. 7, pp. 1068-1078, first published Mar. 7, 2017, doi: 10.1109/TNSRE.2017.2679077.

Jawad et al., "Opportunities and Challenges for Near-Field Wireless Power Transfer: A Review", Energies, vol. 10, No. 1022, Jul. 18, 2017, 28 pgs., doi:10.3390/en10071022.

Jeon et al., "A 143nW Glucose-Monitoring Smart Contact Lens IC with a Dual-Mode Transmitter for Wireless-Powered Backscattering and RF-Radiated Transmission Using a Single Loop Antenna", Symposium on VLSI Circuits, Jun. 9-14, 2019, pp. C294-C295, DOI: 10.23919/VLSIC.2019.8777984.

Jia et al., "A mm-sized free-floating wirelessly powered implantable optical stimulating system-on-a-chip", 2018 IEEE International Solid—State Circuits Conference—(ISSCC), Feb. 11-15, 2018, San Francisco, CA, pp. 468-470, DOI: 10.1109/ISSCC.2018.8310387.

Jiang et al., "A Sub-1 µW Multiparameter Injectable BioMote for Continuous Alcohol Monitoring", IEEE Custom Integrated Circuits Conference (CICC), 2018, pp. 1-4.

Johnson et al., "StimDust: A 6.5 mm3, wireless ultrasonic peripheral nerve stimulator with 82% peak chip efficiency", UC Berkeley. Retrieved from https://escholarship.org/uc/item/8px811qc, published May 5, 2019, 5 pgs., http://dx.doi.org/10.1109/CICC.2018. 8357047.

Kang et al., "A 1.7×4. 1×2 mm3 Fully Integrated pH Sensor for Implantable Applications Using Differential Sensing and Drift-Compensation", 2019 Symposium on VLSI Circuits Digest of Technical Papers, C25-1, pp. C310-C311.

Kang et al., "Design and Optimization of Area-Constrained Wirelessly Powered CMOS UWB SoC for localization applications", IEEE Transactions on Microwave Theory and Techniques, Apr. 2016, vol. 64, No. 4, pp. 1042-1054, DOI: 10.1109/TMTT.2016. 2536663.

Karthaus et al., "Fully Integrated Passive UHF RFID Transponder IC With 16.7-µW Minimum RF Input Power", IEEE Journal of Solid State Circuits, Oct. 2003, vol. 38, No. 10, pp. 1602-1608, DOI: 10.1109/JSSC.2003.817249.

Kelly et al., "A power-efficient neural tissue stimulator with energy recovery", IEEE Transactions on Biomedical Circuits and Systems, Feb. 2011, vol. 5, Issue 1, pp. 20-29, first published Jan. 24, 2011, DOI: 10.1109/TBCAS.2010.2076384.

Kennedy et al., "High intensity focused ultrasound: surgery of the future?", British Journal of Radiology, Sep. 2003, vol. 76, No. 909, pp. 590-599, doi: 10.1259/bjr/17150274.

Kim et al., "A 144-MHz Fully Integrated Resonant Regulating Rectifier with Hybrid Pulse Modulation for mm-Sized Implants", IEEE Journal of Solid-State Circuits, Nov. 2017, vol. 52, Issue 11, pp. 3043-3055, DOI: 10.1109/JSSC.2017.2734901.

Kim et al., "Design of miniaturized wireless power receivers for mm-sized implants", 2017 IEEE Custom Integrated Circuits Conference (CICC), Apr. 30-May 30, 2017, 8 pgs., DOI: 10.1109/CICC. 2017.7993703.

Kim et al., "Wireless power transfer to a cardiac implant", Applied Physics Letters, vol. 101, 2012, pp. 073701-1-073701-4; doi: 10.1063/ 1.4745600.

Kocer et al., "A new transponder architecture with on-chip ADC for longrange telemetry applications", IEEE Journal of Solid-State Circuits, vol. 41, No. 5, Apr. 24, 2006, pp. 1142-1148 [online], [retrieved on Aug. 14, 2020]. Retrieved from the Internet URL: https://www.mpflynngroup.com/uploads/7/3/4/9/73490609/01624404. pdf.

Kotani et al., "High-Efficiency Differential-Drive CMOS Rectifier for UHF RFIDs", IEEE Journal of Solid-State Circuits, Nov. 2009, vol. 44, Issue 11, pp. 3011-3018, DOI:10.1109/JSSC.2009. 2028955.

Kulkarni et al., "A 750 Mb/s, 12 pJ/b, 6-to-10 GHz CMOS IR-UWB Transmitter with Embedded On-Chip Antenna", IEEE Journal of Solid-State Circuits, vol. 44, No. 2, Feb. 2009, pp. 394-403, DOI: 10.1109/JSSC.2008.2011034.

Kuo et al., "Near-field power transfer and backscattering communication to miniature RFID tag in 65 nm CMOS technology", 2016 IEEE MTT-S International Microwave Symposium (IMS), May 22-27, 2016, 4 pgs., DOI: 10.1109/MWSYM.2016.7540221.

Kurs et al., "Wireless Power Transfer via Strongly Coupled Magnetic Resonances", Science, vol. 317, No. 5834, Jul. 6, 2007, published online Jun. 7, 2007, pp. 83-86, DOI: 10.1126/science. 1143254.

Le et al., "Efficient Far-Field Radio Frequency Energy Harvesting for Passively Powered Sensor Networks", IEEE Journal of Solid-State Circuits, May 2008, vol. 43, No. 5, pp. 1287-1302, DOI: 10.1109/JSSC.2008.920318.

Lepock, James R., "Cellular effects of hyperthermia: relevance to the minimum dose for thermal damage," International Journal of Hyperthermia, vol. 19:3, pp. 252-266, 2003, Copyright 2003 Taylor & Francis Ltd.

Li, Xing et al., "A 13.56 MHz Wireless Power Transfer System With Reconfigurable Resonant Regulating Rectifier and Wireless Power Control for Implantable Medical Devices," IEEE Journal of Solid-State Circuits, vol. 50, No. 4, Apr. 2015, 12 pages, Copyright 2015 IEEE.

Liu et al., "A 650-pJ/bit MedRadio transmitter with an FIR-embedded phase modulator for medical micro-power networks (MMNs)", IEEE Transactions on Circuits and Systems I: Regular Papers, 2013, vol. 60, No. 12, pp. 3279-3288, DOI: 10.1109/TCSI. 2013.2265970.

Lo et al., "A fully integrated wireless SoC for motor function recovery after spinal cord injury", IEEE Transactions on Biomedical Circuits and Systems, Jun. 2017, vol. 11, Issue 3, pp. 497-509, first published May 23, 2017, DOI: 10.1109/TBCAS.2017.2679441.

Lo et al., "Bio-Impedance Characterization Technique with Implantable Neural Stimulator Using Biphasic Current Stimulus", Conference Proceedings of the IEEE Engineering in Medicine and Biology Society, 2014, pp. 474-477, doi: 10.1109/EMBC.2014.6943631.

Lonappan et al., "Nondestructive Measurement of Human Blood at Microwave Frequencies", Journal of Electromagnetic Waves and Applications, 2007, vol. 21, Issue 8, 1131-1139, DOI: 10.1163/ 156939307781749740.

Lopez-Lapena et al., "A closed-loop maximum power point tracker for subwatt photovoltaic panels", IEEE Transactions on Industrial Electronics, Mar. 2012, vol. 59, No. 3, pp. 1588-1596, DOI: 10.1109/TIE.2011.2161254.

Lu et al., "Flexible Neural Electrode Array Based-on Porous Graphene for Cortical Microstimulation and Sensing", Scientific Reports, Sep. 19, 2016, vol. 6, No. 33526, 9 pgs., DOI: 10.1038/srep33526.

Lu et al., "Ultra-flexible Piezoelectric Devices Integrated with Heart to Harvest the Biomechanical Energy", Scientific Reports, vol. 5, No. 16065, Nov. 5, 2015, 9 pgs., https://doi.org/10.1038/srep16065.

Lyu et al., "A 430-Mhz Wirelessly Powered Implantable Pulse Generator with Intensity/Rate Control and Sub-1 µA Quiescent Current Consumption", IEEE Transactions on Biomedical Circuits and Systems, vol. 13, No. 1, Feb. 2019, pp. 180-190, DOI: 10.1109/ TBCAS.2018.2879357.

Lyu et al., "A 915-MHz Far-Field Energy Harvester with -22-dBm Sensitivity and 3-V Output Voltage Based on Antenna-and-Rectified Codesign", IEEE Microwave and Wireless Components Letters, Aug. 2019, vol. 29, No. 8, pp. 557-559, DOI: 10.1109/LMWC. 2019.2923685.

(56) References Cited

OTHER PUBLICATIONS

Lyu et al., "An Energy-Efficient Wirelessly Powered Millimeter-Scale Neurostimulator Implant Based on Systematic Codesign of an Inductive Loop Antenna and a Custom Rectifier", IEEE Transactions on Biomedical Circuits and Systems, vol. 12, No. 5, Oct. 2018, pp. 1131-1143, DOI: 10.1109/TBCAS.2018.2852680.

Lyu et al., "Synchronized Biventricular Heart Pacing in a Closed-chest Porcine Model based on Wirelessly Powered Leadless Pacemakers", Scientific Reports, 10, Article No. 2067, 2020, 13 pgs.

Lyu et al., "Towards the Implementation of a Wirelessly Powered Dielectric Sensor with Digitized Output for Implantable Applications", IEEE Sensors Letters, Mar. 2019, vol. 3, No. 3, pp. 1-4, first published Jan. 30, 2019.

Mandal et al., "Low-power CMOS rectifier design for RFID applications", IEEE Transactions on Circuits and Systems I: Regular Papers, Jul. 2007, vol. 54, No. 6, pp. 1177-1188, DOI: 10.1109/TCSI.2007.895229.

Meyer et al., "First in a series on the leadless pacing: Percutaneous implantable transcatheter pacemaker—background, technical aspects, and possible pitfalls", d-Journal of Cardiology Practice, Aug. 23, 2016, vol. 14, No. 20, 18 pgs.

Mirbozorgi et al., "A Single-Chip Full-Duplex High Speed Transceiver for Multi-Site Stimulating and Recording Neural Implants", IEEE Transactions on Biomedical Circuits and Systems, vol. 10, No. 3, Jun. 2016, pp. 643-653, DOI: 10.1109/TBCAS.2015.2466592.

Mirzavand et al., "High-Resolution Dielectric Sensor Based on Injection-Locked Oscillators", IEEE Sensors Journal, Jan. 1, 2018, vol. 18, Issue 1, pp. 141-148, published online published Nov. 13, 2017, DOI: 10.1109/JSEN.2017.2772923.

Montgomery et al., "Wirelessly powered, fully internal optogenetics for brain, spinal and peripheral circuits in mice", Nature Methods, 2015, vol. 12, No. 10, pp. 969-974, published online Aug. 17, 2015, DOI: 1031038/NMETH.3536.

Niemann et al., "Longevity of Implantable Pulse Generators in Bilateral Deep Brain Stimulation for Movement Disorders", Neuromodulation, vol. 21, No. 6, Aug. 2018, published online Dec. 19, 2017, pp. 597-603, doi: 10.1111/ner.12743.

Pandey et al., "A Sub-100 µW MICS/ISM Band Transmitter Based on Injection-Locking and Frequency Multiplication", IEEE Journal of Solid-State Circuits, May 2011, vol. 46, Issue 5, pp. 1049-1058, first published Apr. 5, 2011, DOI: 10.1109/JSSC.2011.2118030.

Papotto et al., "A 90nm CMOS 5mb/s crystal-less rf transceiver for rf-powered wsn nodes", 2012 IEEE International Solid-State Circuits Conference, Feb. 19-23, 2012, pp. 451-453, DOI: 10.1109/ISSCC.2012.6177087.

Paul, "Inductance: loop and partial", John Wiley & Sons, 2011, 395 pgs., presented in two parts.

Pellerano et al., "A mm-Wave Power-Harvesting RFID Tag in 90 nm CMOS", IEEE Journal of Solid-State Circuits, Aug. 2010, vol. 45, Issue 8, pp. 1627-1637, DOI: 10.1109/JSSC.2010.2049916.

Pozar, David M., "Microwave Engineering", John Wiley & Sons, Inc., Third Edition, 2005, Chapter 13 (Oscillators and Mixers): pp. 604-657, Chapter 14 (Introduction to Microwave Systems): pp. 658-708, 105 pgs.

Radiom et al., "Far-Field On-Chip Antennas Monolithically Integrated in a Wireless-Powered 5.8-GHz Downlink/UWB Uplink RFID Tag in 0.18-µm Standard CMOS", IEEE Journal of Solid-State Circuits, Sep. 2010, vol. 45, Issue 9, pp. 1746-1758, DOI: 10.1109/JSSC.2010.2055630.

Rahmani et al., "A 1.6mm3 Wirelessly Powered Reconfigurable FDD Radio with On-Chip Antennas Achieving 4.7 pJ/b TX and 1 pJ/b RX Energy Efficiencies for Medical Implants", Conference: 2020 IEEE Custom Integrated Circuits Conference (CICC), Apr. 2020, 4 pgs., DOI:10.1109/CICC48029.2020.9075935.

Rahmani et al., "A Dual-Mode RF Power Harvesting System With an On-Chip Coil in 180-nm SOI CMOS for Millimeter-Sized Biomedical Implants", IEEE Transactions on Microwave Theory and Techniques, Oct. 2018, vol. 67, No. 1, pp. 414-428, DOI:10.1109/TMTT.2018.2876239.

Rahmani et al., "A Wireless Power Receiver with an On-chip Antenna for Millimeter-size Biomedical Implants in 180 nm SOI CMOS", in 2017 IEEE MTT-S International Microwave symposium (IMS), Jun. 2017, pp. 300-303.

Rahmat-Samii et al., "Implanted antennas in medical wireless communications", Synthesis Lectures on Antennas, 2005, 1.1 pp. 1-82.

Rajavi et al., "An RF-powered FDD radio for neural microimplants", IEEE Journal of Solid-State Circuits, May 2017, vol. 52, Issue: 5, pp. 1221-1229, DOI: 10.1109/JSSC.2016.2645601.

Ramrakhyani, Anil Kumar et al., "Design and Optimization of Resonance-Based Efficient Wireless Power Delivery Systems for Biomedical Implants," IEEE Transactions on Biomedical Circuits and Systems, vol. 5, No. 1, Feb. 2011, 16 pages, Copyright 2010 IEEE.

Randles, "Kinetics of rapid electrode reactions", Discussions of the Faraday Society, 1947, vol. 1, pp. 11-19.

Rategh et al., "Superharmonic Injection-Locked Frequency Dividers", IEEE Journal of Solid-State Circuits, Jun. 1999, vol. 34, No. 6, pp. 813-821.

Razavi, "Design of analog CMOS Integrated Circuits", McGraw-Hill Series in Electrical and Computer Engineering, 2001, 706 pgs., (presented in eight parts).

Razavi, Behzad, "RF Microelectronics", New Jersey: Prentice Hall, 1998, vol. 1, 98 pgs., Chapter 8: pp. 497-594.

Rodriguez et al, "Long-term results of electrical stimulation of the lower esophageal sphincter for the treatment of gastroesophageal reflux disease", Endoscopy, Aug. 2013, vol. 45, No. 8, pp. 595-604, DOI: 10.1055/s-0033-1344213.

Sample et al., "Analysis, Experimental Results, and Range Adaptation of Magnetically Coupled Resonators for Wireless Power Transfer", IEEE Transactions on Industrial Electronics, vol. 58, No. 2, Feb. 2011, pp. 544-554, DOI: 10.1109/TIE.2010.2046002.

Sankaragomathi et al., "A 27w subcutaneous wireless biosensing platform with optical power and data transfer", Proceedings of the IEEE 2014 Custom Integrated Circuits Conference, Sep. 15, 2014, pp. 1-4.

Sayenko et al., "Spinal segment-specific transcutaneous stimulation differentially shapes activation pattern among motor pools in humans", Journal of Applied Physiology, 2015, vol. 118, pp. 1364-1374, first published Mar. 26, 2015; doi: 10.1152/japplphysiol.01128.2014.

Shi et al., "A 10 mm3 Inductive Coupling Radio for Syringe-Implantable Smart Sensor Nodes", IEEE Journal of Solid-State Circuits, Nov. 2016, vol. 51, No. 11, pp. 2570-2583, DOI: 10.1109/JSSC.2016.2606162.

Shi et al., "A 10mm3 syringe-implantable near-field radio system on glass substrate", IEEE Int. Solid-State Circuits Conf. (ISSCC) Dig. Tech. Papers, pp. 448-449, Feb. 2016.

Silvetti et al., "Cardiac pacing in pediatric patients with congenital heart defects: transvenous or epicardial?", Europace, vol. 15, No. 9, Sep. 2013, published online Feb. 24, 2013, pp. 1280-1286. doi: 10.1093/europace/eut029.

Soontornpipit, "Design of an Implantable Antenna Feasibility Study for Continuous Glucose Monitoring", ECTI Transactions on Electrical Engineering, Electronics, and Communications, Feb. 2014, vol. 12, No. 1, pp. 44-52.

Stoopman et al., "Co-Design of a CMOS Rectifier and Small Loop Antenna for Highly Sensitive RF Energy Harvesters", IEEE Journal of Solid-State Circuits, Mar. 2014, vol. 49, Issue 3, pp. 622-634, DOI: 10.1109/JSSC.2014.2302793.

Sun et al., "A Wirelessly Powered Injection-Locked Oscillator With On-Chip Antennas in 180-nm SOI CMOS for Spectroscopy Application", IEEE Sensors Letters, vol. 3, No. 7, Jul. 3, 2019, pp. 1-4 [online], [retrieved on Aug. 14, 2020]. Retrieved from the Internet URL: https://ieeexplore.ieee.org/abstract/document/8754750.

Sun, Yuxiang et al., "A Wirelessly Powered Injection-Locked Oscillator with On-Chip Antennas in 180nm SOI CMOS," EEE Paper 978-1-5090-0698-4/16, 3 pages, Copyright 2016 IEEE.

Tabesh et al., "A Power-Harvesting Pad-Less Millimeter-Sized Radio", IEEE Journal of Solid-State Circuits, Apr. 2015, vol. 50, Issue: 4, pp. 962-977, DOI: 10.1109/JSSC.2014.2384034.

(56) References Cited

OTHER PUBLICATIONS

Teh et al., "Design and analysis of UHF micropower CMOS DTMOST rectifiers", IEEE Transactions on Circuits and Systems—II: Express Briefs, Feb. 2009, vol. 56, No. 2, pp. 122-126, doi: 10.1109/TCSII.2008.2010190.

Theilmann et al., "A $\mu$W Complementary Bridge Rectifier with Near Zero Turn-on Voltage in SOS CMOS for Wireless Power Supplies", IEEE Transactions on Circuits and Systems I: Regular Papers, 2012, vol. 59, No. 9, pp. 2111-2124, DOI: 10.1109/TCSI.2012.2185293.

Tjong et al., "Permanent Leadless Cardiac Pacemaker Therapy a Comprehensive Review", Circulation, Apr. 11, 2017, vol. 135, pp. 1458-1470, Doi: 10.1161/Circulationaha.116.025037.

Tolosa et al., "Electrochemically deposited iridium oxide reference electrode integrated with an electroenzymatic glutamate sensor on a multielectrode array microprobe", Biosensors and Bioelectronics, 2013, vol. 42, pp. available online Nov. 6, 2012, pp. 256-260, http://dx.doi.org/10.1016/jbios.2012.10.061.

Van Dongen et al., "Does a coupling capacitor enhance the charge balance during neural stimulation? An empirical study", Medical & Biological Engineering and Computing, 2016, vol. 54, pp. 93-101, published online May 29, 2015, DOI 10.1007/s11517-015-1312-9.

Van Rees et al., "Implantation-related complications of implantable cardioverter-defibrillators and cardiac resynchronization therapy devices: a systematic review of randomized clinical trials", Journal of the American College of Cardiology, Aug. 30, 2011, vol. 58, Issue 10, pp. 995-1000, https://doi.org/10.1016/j.jacc.2011.06.007.

Wan et al., "Analysis and design of a thermoelectric energy harvesting system with reconfigurable array of thermoelectric generators for IoT applications", IEEE Transactions on Circuits and Systems I: Regular Papers, Sep. 2017, vol. 64, No. 9, pp. 2346-2358, DOI: 10.1109/TCSI.2017.2708763.

Weber et al., "A Miniaturized Single-Transducer Implantable Pressure Sensor With Time-Multiplexed Ultrasonic Data and Power Links", IEEE Journal of Solid-State Circuits, Apr. 2018, vol. 53, No. 4, pp. 1089-1101, DOI: 10.1109/JSSC.2017.2782086.

Weber et al., "Functional electrical stimulation using microstimulators to correct foot drop: a case study1", Canadian Journal of Physiology and Pharmacology, 2004, vol. 82, No. 8-9, first published Oct. 19, 2004, pp. 784-792, doi: 10.1139/Y04-078.

Xie et al., "Wireless power transfer and applications to sensor networks", IEEE Wireless Communications, Aug. 2013, vol. 20, Issue: 4, pp. 140-145, DOI: 10.1109/MWC.2013.6590061.

Xu et al., "A fully implantable stimulator with wireless power and data transmission for experimental investigation of epidural spinal cord stimulation", IEEE Transactions on Neural Systems and Rehabilitation Engineering, 2015, vol. 23, No. 4, pp. 683-692, Doi: 10.1109/TNSRE.2015.2396574.

Yadav et al., "Low Voltage Low Power Sub-threshold Operational Amplifier in 180nm CMOS", 2017 IEEE Third International Conference on Sensing signal Processing and Security (ICSSS), 2017, 4 pgs.

International Preliminary Report on Patentability dated Jan. 23, 2025 issued in International Application No. PCT/US2023/027740.

J. N. Burghartz, "You can't be too thin or too flexible," in IEEE Spectrum, vol. 50, No. 3, pp. 38-61, Mar. 2013, doi: 10.1109/MSPEC.2013.6471057. keywords: {Remote sensing; Mobile communication; Medical diagnostic imaging; Sensors; Home appliances}, (Year: 2013).

* cited by examiner

Method
2000

2010 — Open Loop

Pace — 2020

100

111p

111s

SENSE   SENSE   SENSE   SENSE

2030

NO

2040 — Regular?

YES

Stop Pading — 2050

Method
3000

Closed
Loop — 3010

Sense — 3020

100

NO

111

Excitable
gap?

3030

3040

Pace Pace    Pace Pace    Pace Pace    Pace Pace

NO

3050

Regular?

Stop
Pacing

3060

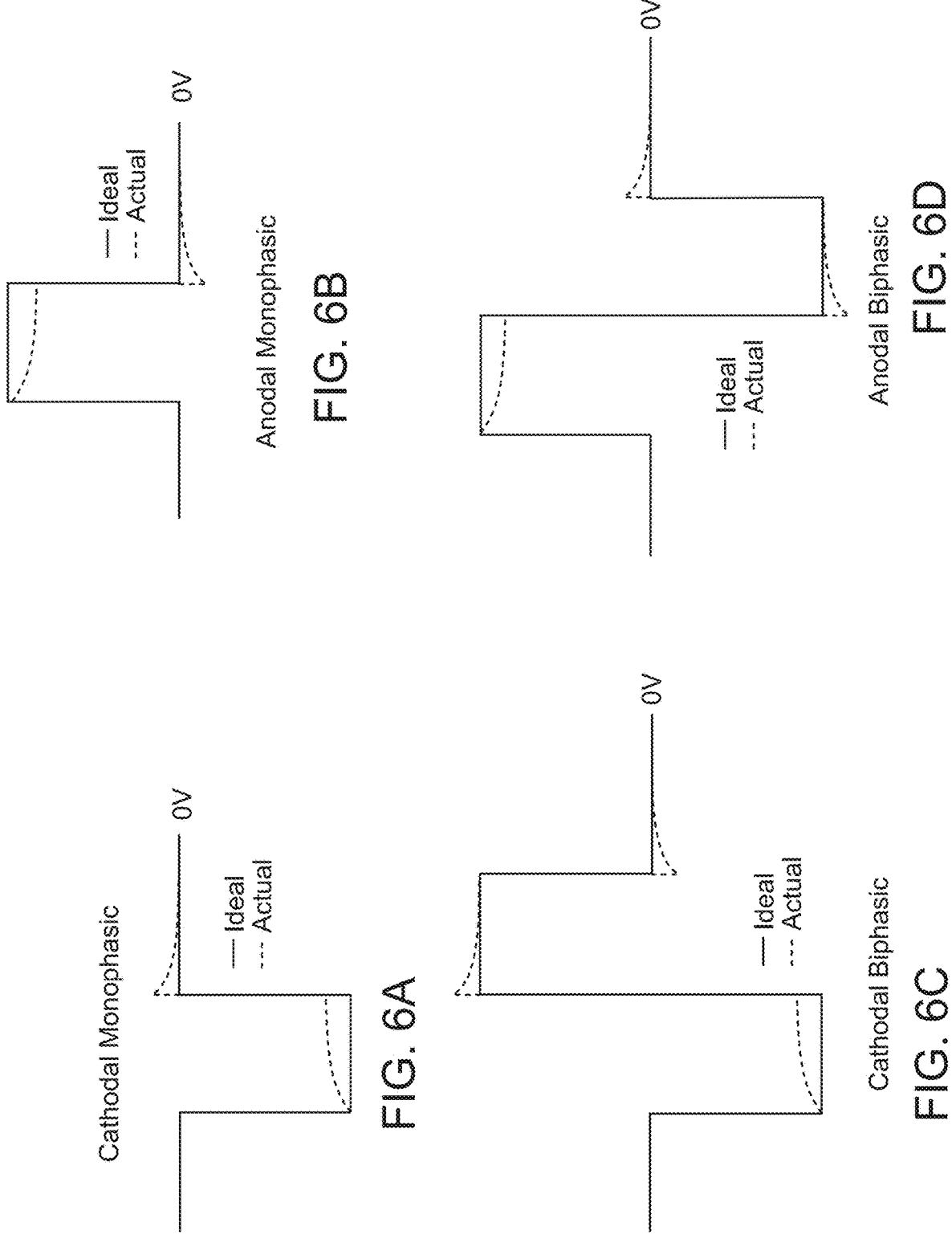

Charge Balanced

Charge imbalanced

Charge Balanced with Delay

Charge Balanced w/
Fast Reversal

Charge Balanced w/
Slow Reversal

Unipolar voltages

Phase trajectories

Phase difference

Sync Index

Threshold crossing

Regular rhythm
Sync Index < Threshold

Irregular rhythm
Sync Index < Threshold

Time (sec)

Method 4000

4010 — Patient with AF

4020 — Contact or non-contact Left Atrial ECG data

4030 — *AF Modeling and Therapy Mapping*

4040 — Determine optimal therapy strategy

Ablation

Pacing Therapy

Ablation & Pacing Therapy

Perform optimal ablation per Guidance

4050

Place Satellite

4060

Perform optimal ablation per Guidance Place Satellite

4070

Method 5000

Reference signal [ECG]    Original Atrial signals ["Sn"]    Atrial Signal with Ventricular Artifact Reduced [L]

FIG. 12D
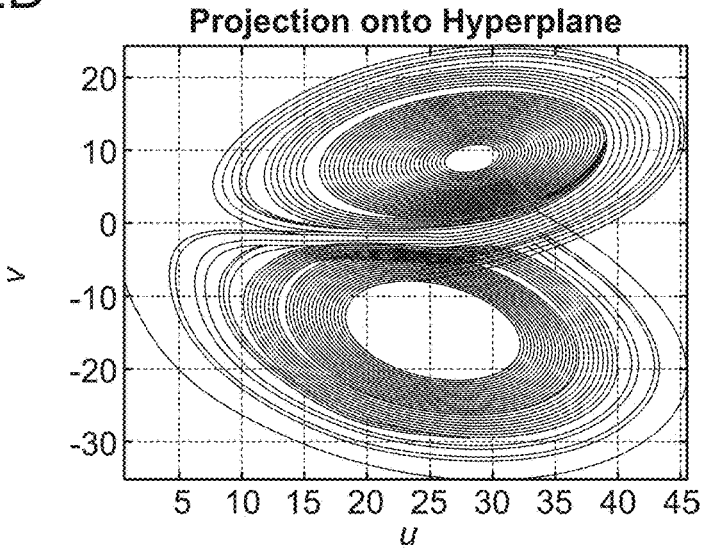
Projection onto Hyperplane
FIG. 12E
Projected Time Series
FIG. 12F
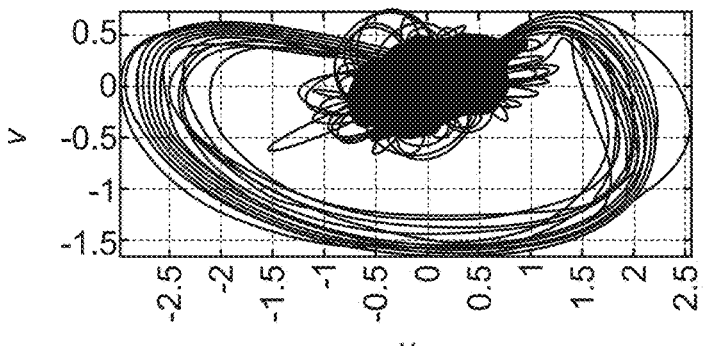
Projection onto Hyperplane (Sinus and AF)

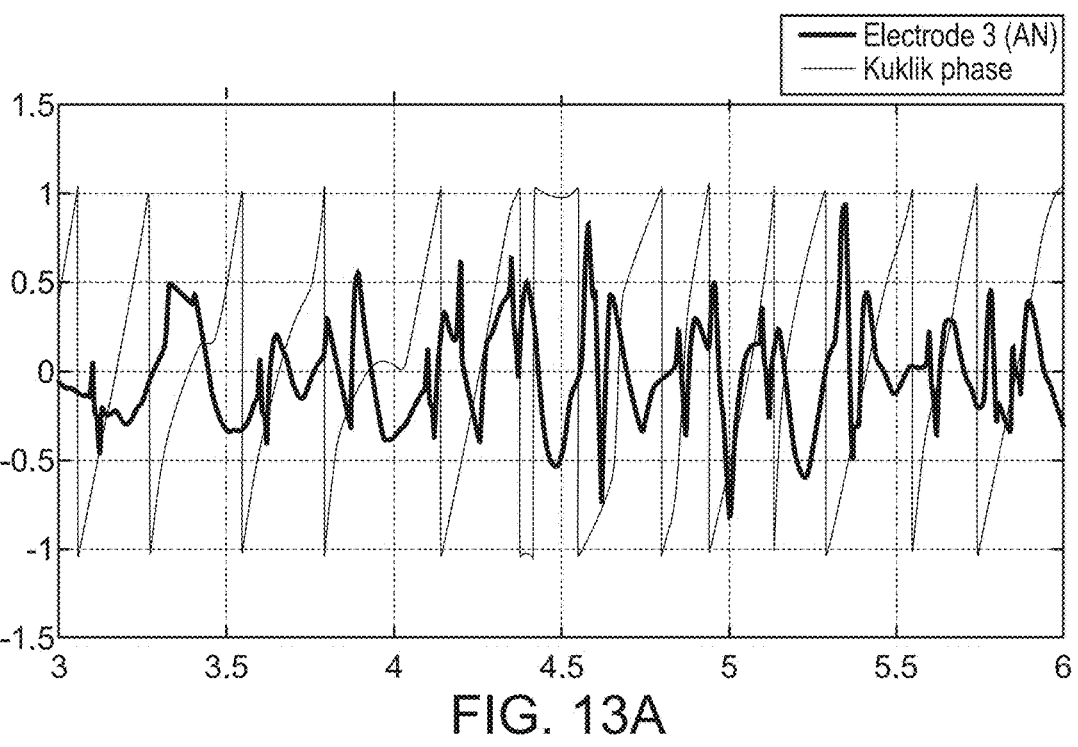
FIG. 13A
FIG. 13B
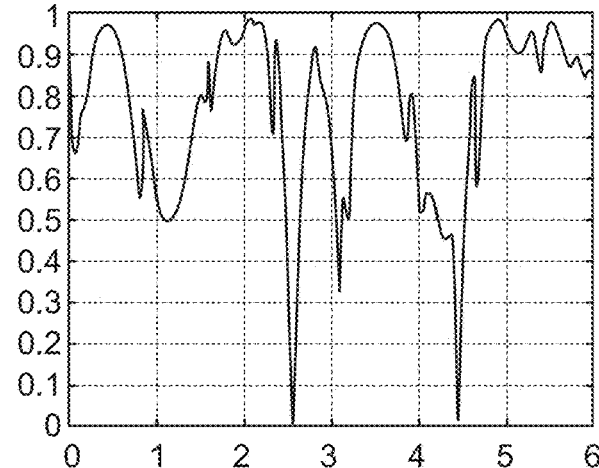
FIG. 13C
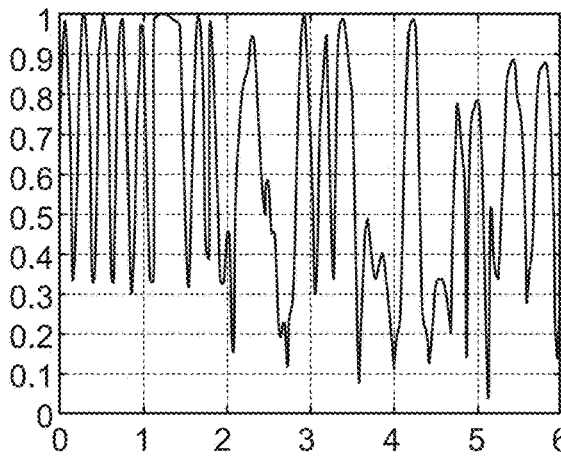

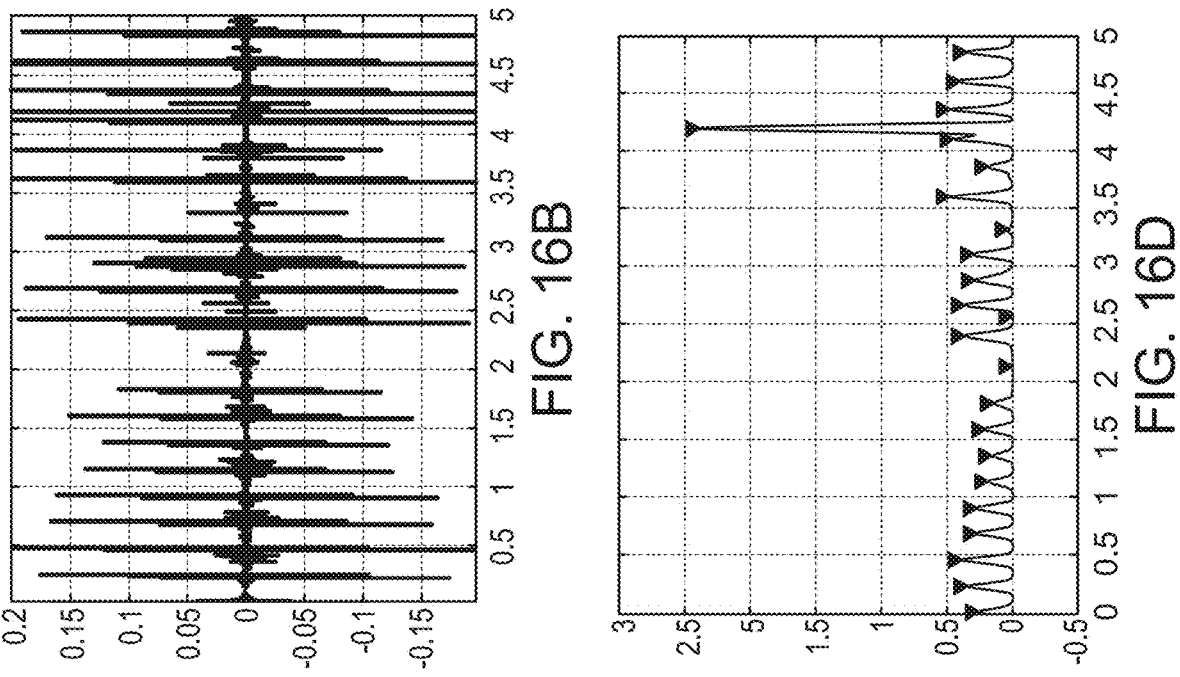
FIG. 16A
FIG. 16B
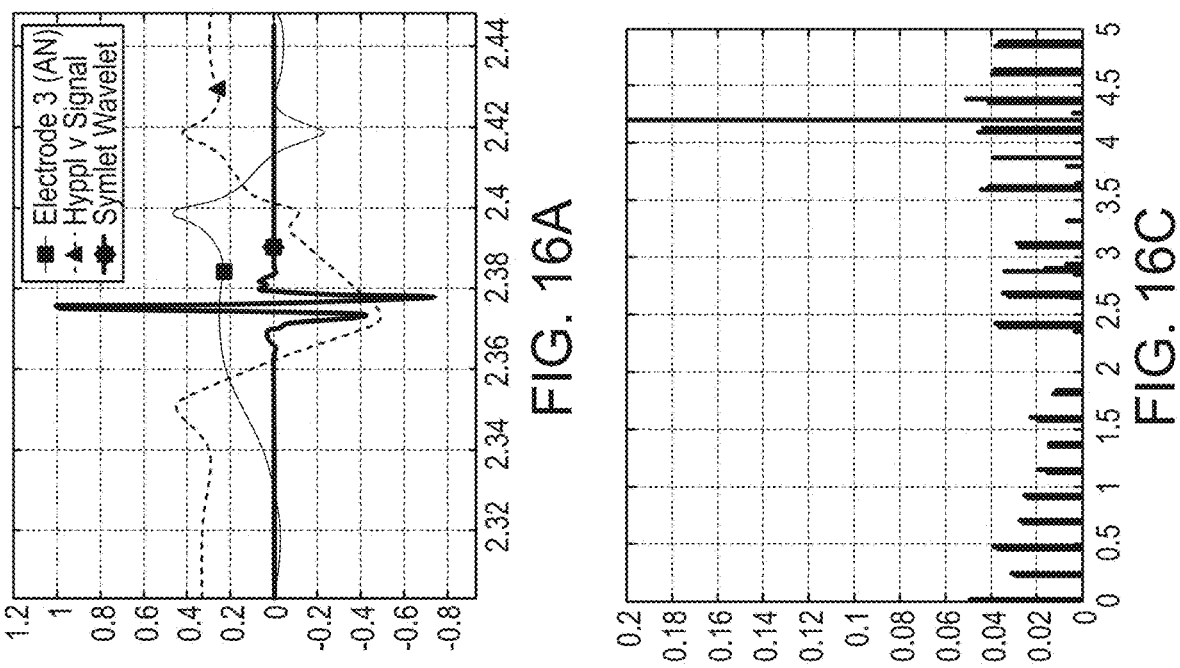
FIG. 16C
FIG. 16D

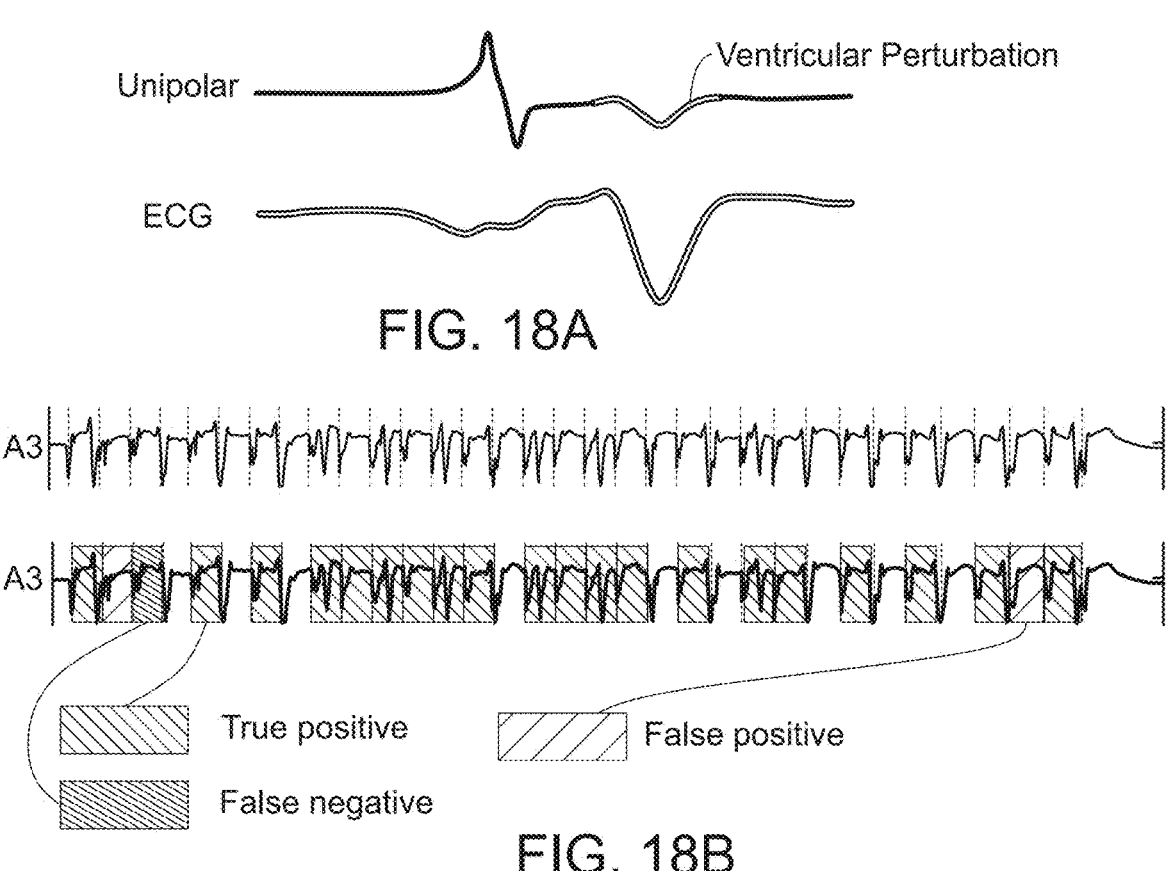
FIG. 18A
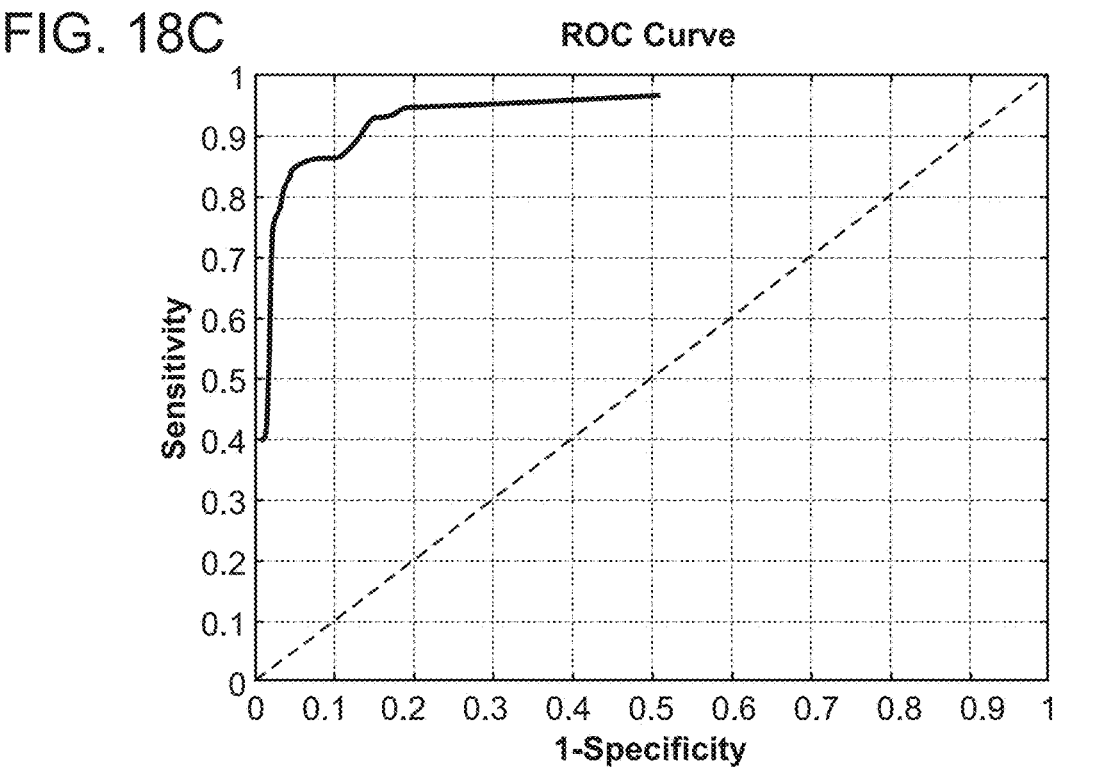
FIG. 18B
FIG. 18C
ROC Curve

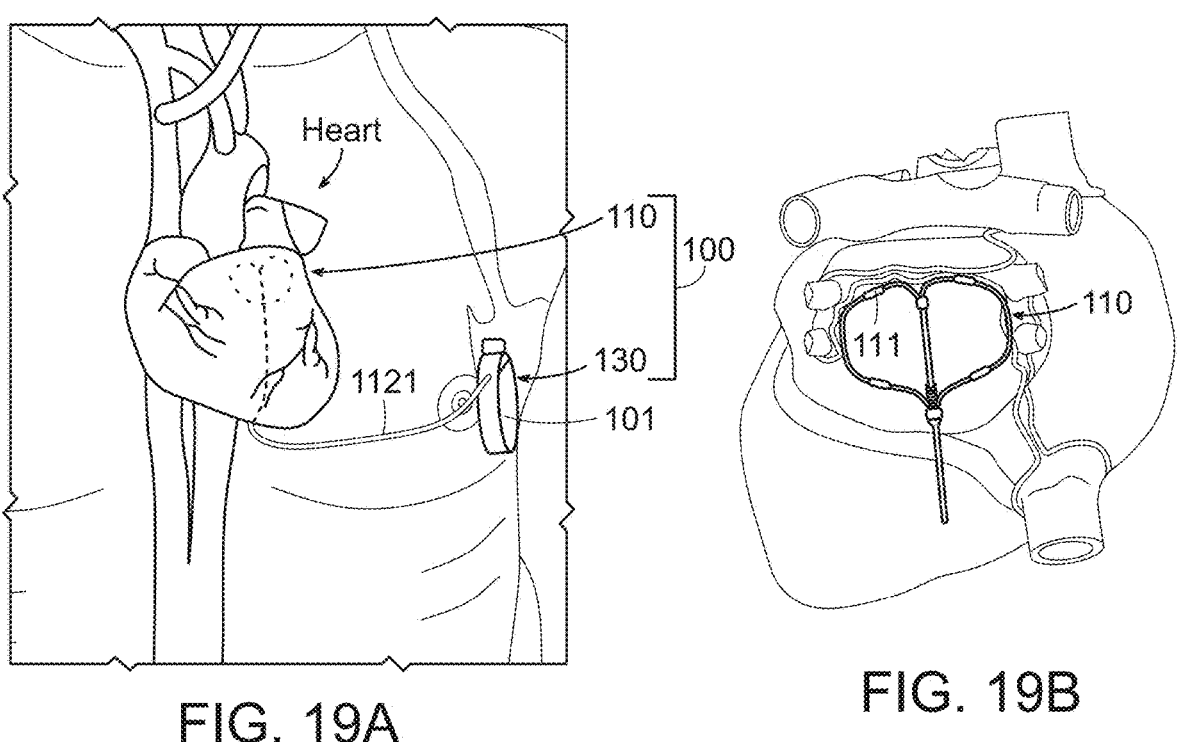
FIG. 19A
FIG. 19B
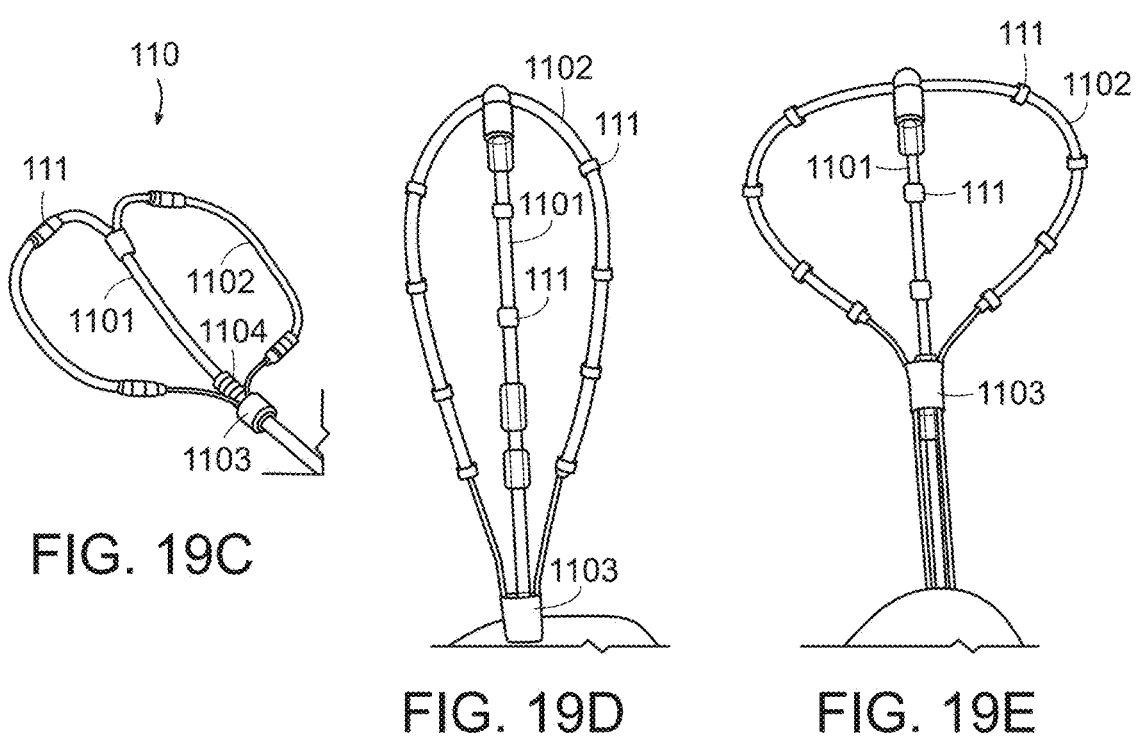
FIG. 19C
FIG. 19D          FIG. 19E

ADVANCED PACING

CROSS REFERENCE TO RELATED APPLICATIONS

The present application is a bypass continuation of International PCT Patent Application Serial Number PCT/US2023/027740, entitled "ADVANCED PACING", filed Jul. 14, 2023, which claims priority to U.S. Provisional Patent Application Ser. No. 63/389,094, filed Jul. 14, 2022, entitled "ADVANCED PACING", which is hereby incorporated by reference, and which also claims priority to U.S. Provisional Patent Application Ser. No. 63/453,570, filed Mar. 21, 2023, entitled "ADVANCED PACING", which is hereby incorporated by reference.

The present application, while not claiming priority to, may be related to International PCT Patent Application Serial Number PCT/US2022/036926, entitled "STIMULA-TION SYSTEM", filed Jul. 13, 2022, which claims priority to U.S. Provisional Patent Application Ser. No. 63/336,517, entitled "STIMULATION SYSTEM", filed Apr. 29, 2022 and U.S. Provisional Patent Application Ser. No. 63/326,190, entitled "STIMULATION SYSTEM", filed Mar. 31, 2022, and U.S. Provisional Patent Application Ser. No. 63/221,117, entitled "STIMULATION SYSTEM", filed Jul. 13, 2021, each of which is hereby incorporated by reference.

The present application, while not claiming priority to, may be related to U.S. application Ser. No. 17/637,877, entitled "Cardiac Stimulation System", filed Feb. 24, 2022, which is a 35 USC 371 national stage filing of International PCT Patent Application Serial Number PCT/US2020/049349, entitled "Cardiac Stimulation System" filed Sep. 4, 2020, Publication Number WO 2021/046313, published Mar. 11, 2021, which claimed priority to U.S. Provisional Application Ser. No. 62/895,655, entitled "Multi-Side Micro Pacing Circuits and Algorithms, Integrated into a Venously Placed Stent Assembly", filed Sep. 4, 2019, each of which is hereby incorporated by reference.

The present application, while not claiming priority to, may be related to U.S. application Ser. No. 17/908,002, entitled "Cardiac Pacing Device", filed Aug. 30, 2022, which is a 35 USC 371 national stage filing of International PCT Patent Application Serial Number PCT/US2021/021467, entitled "Cardiac Pacing Device", filed Mar. 9, 2021, Publication Number WO 2021/183487, published Sep. 16, 2021 which claims priority to U.S. Provisional Patent Application Ser. No. 62/987,238, entitled "Stent, Mounted and Delivered Wireless, Batteryless Micropacing Chip System", filed Mar. 9, 2020, each of which is hereby incorporated by reference.

The present application, while not claiming priority to, may be related to U.S. application Ser. No. 17/925,821, entitled "Pacing and Sensing Devices and Control System", filed Nov. 16, 2022, which is a 35 USC 371 national stage filing of International PCT Patent Application Serial Number PCT/US2021/035132, entitled "Pacing and Sensing Devices and Control System", filed Jun. 1, 2021, Publication Number WO2021/247490, published Dec. 9, 2021, which claims priority to U.S. Provisional Patent Application Ser. No. 63/032,687, entitled "Rechargeable Biomedical Battery Powered Wireless Self-Anchoring Micro-Pacing And Sensing Devices And Control System", each of which is hereby incorporated by reference.

FIELD OF THE INVENTIVE CONCEPTS

The present inventive concepts relate generally to stimulation systems, and in particular systems that stimulate tissue of a patient's heart.

BACKGROUND

The heart is a critical muscle in humans and many other animals that is responsible for circulating blood through the circulatory system. The human heart is made up of four chambers, two upper atria, and two lower ventricles, organized into a left and right pairing of an atrium and a ventricle. In a healthy heart, the chambers contract and relax in a synchronized fashion, referred to as a "beat," in order to force blood through the network of veins and arteries.

Irregular heartbeats can pose a health risk, and in some cases normal beating can be restored via electrical stimulation. Implantable devices called "pacemakers" are devices which can stimulate the muscle tissue, causing it to contract. By methodically and accurately applying stimulation as needed, normal heart rhythm can be restored.

There is a need for improved systems for treating irregular heartbeats.

SUMMARY

According to an aspect of the present inventive concepts, a system for providing therapy to the heart of a patient comprises an implantable device configured to be implanted proximate the heart of the patient. The implantable device comprises at least one sensing electrode configured to sense electrical activity of the heart, at least two pacing electrodes configured to deliver electrical stimulation energy to tissue of the heart, and a controller and a memory storage component coupled to the controller. The memory storage component stores instructions for the controller to perform one or more algorithms. The one or more algorithms are executable to determine a pacing strategy configured to at least terminate atrial fibrillation.

In some embodiments, the implantable device delivers the electrical stimulation based on the pacing strategy.

In some embodiments, the pacing strategy is based on the complexity of the atrial fibrillation.

In some embodiments, the pacing strategy includes providing stimulation energy intended to advance and/or block one or more cardiac activation wavefronts.

In some embodiments, the electrical stimulation is delivered ahead of an approaching cardiac activation wavefront.

In some embodiments, the one or more algorithms are executable to identify the presence of atrial fibrillation.

In some embodiments, the delivery of the electrical stimulation energy is imperceptible to the patient.

In some embodiments, the pacing strategy is configured to synchronize atrial activation.

In some embodiments, the one or more algorithms are executable to identify the restoration of normal rhythm and to terminate the delivery of the electrical stimulation energy.

In some embodiments, the system is configured to deliver a first form of therapy and a second form of therapy, and the implantable device comprises at least one power supply, and the system is configured to provide only the first form of therapy when the energy level of the at least one power supply is below a threshold. The first form of therapy can comprise a life-saving therapy.

In some embodiments, the system is configured to deliver a first form of therapy and a second form of therapy, and the implantable device is configured to sequentially operate in a regular-power mode and a low-power mode, and the system is configured to provide only the first form of therapy when the implantable device is operating in the low-power mode. The first form of therapy can comprise a life-saving therapy.

In some embodiments, the system is configured to provide variable heart rate pacing and/or pacing that is at least 5%, 10%, or 20% faster than normal sinus rhythm. The system can be further configured to deliver spatiotemporal resynchronization therapy. The spatiotemporal resynchronization therapy can comprise delivery of energy that controls a fibrillating substrate by deterministically pacing into the narrowed excitable gap present during AF.

In some embodiments, the implantable device is configured to provide spatiotemporal resynchronization therapy and another pacing therapy. The implantable device can comprise two power supplies, and each supply can be configured to provide power for one of the spatiotemporal resynchronization therapy or the pacing stimulation. The spatiotemporal resynchronization therapy can comprise delivery of energy that controls a fibrillating substrate by deterministically pacing into the narrowed excitable gap present during AF.

In some embodiments, the system is configured to perform bradycardia pacing, heart rate variability pacing, and spatiotemporal resynchronization therapy. The spatiotemporal resynchronization therapy can comprise delivery of energy that controls a fibrillating substrate by deterministically pacing into the narrowed excitable gap present during AF.

In some embodiments, a first algorithm of the one or more algorithms is configured to cause the implantable device to deliver energy to minimize susceptibility to initiation of AF in patients with HFpEF.

In some embodiments, a first algorithm of the one or more algorithms is configured to determine when to pace for prevention of an arrhythmia versus when to pace for termination of an arrhythmia.

In some embodiments, a first algorithm of the one or more algorithms is configured to determine a particular type of pacing to be delivered and when the pacing should be delivered.

In some embodiments, a first algorithm of the one or more algorithms is configured to determine the patient's susceptibility to an arrhythmia, and the first algorithm is further configured to determine whether or not variable rate pacing should be delivered.

In some embodiments, a first algorithm of the one or more algorithms derives the mean and standard deviation of heart rate of the patient for a predetermined period, and the algorithm causes the implantable device to deliver stimuli according to a fractal and/or other nonlinear function that paces the heart at a time that is earlier than the mean-cycle length to impose a variation in heartbeat.

In some embodiments, the system is configured to deliver pacing energy with different durations of earliness corresponding to a heartbeat, and the delivery is configured to impose a desired variability in the heart rate over time. The system can be configured to occasionally inhibit pacing such that the intrinsically-longest cycle length is achieved.

In some embodiments, a first algorithm of the one or more algorithms is configured to cause the implantable device to periodically stop pacing, and to assess the mean and standard deviation of heart rate.

In some embodiments, the system is configured to deliver pacing energy to pace the heart at a rate that is faster than the intrinsic rate.

In some embodiments, a first algorithm of the one or more algorithms is configured to cause the implantable device to perform a first energy delivery configured to restore sinus rhythm, and a second algorithm of the one or more algorithms is configured to cause the implantable device to perform a second energy delivery configured to maintain normal heart rate variability that reduces vulnerability to recurrence of atrial fibrillation or other arrhythmia.

In some embodiments, a first algorithm of the one or more algorithms is configured to cause the implantable device to periodically inhibit pacing, to assess the intrinsic heart rate while the pacing is inhibited, and to cause the pacing to remain inhibited if is determined that the SA-node has recovered.

In some embodiments, the system comprises a clinician device, and the system is configured to send an alert to the clinician device when the system transitions into an alert or other pre-determined state of the system.

In some embodiments, the implantable device is configured to terminate AF, prevent AF, and treat prolonged bradycardia.

In some embodiments, the system is configured to deliver spatiotemporal resynchronization therapy. The spatiotemporal resynchronization therapy can comprise delivery of energy that controls a fibrillating substrate by deterministically pacing into the narrowed excitable gap present during AF.

The technology described herein, along with the attributes and attendant advantages thereof, will best be appreciated and understood in view of the following detailed description taken in conjunction with the accompanying drawings in which representative embodiments are described by way of example.

INCORPORATION BY REFERENCE

All publications, patents, and patent applications mentioned in this specification are herein incorporated by reference to the same extent as if each individual publication, patent, or patent application was specifically and individually indicated to be incorporated by reference. The content of all publications, patents, and patent applications mentioned in this specification are herein incorporated by reference in their entirety for all purposes.

BRIEF DESCRIPTION OF THE DRAWINGS

FIGS. 6A-D and 7A-E illustrate various pacing pulses, consistent with the present inventive concepts.

FIGS. 12A-F illustrate various graphs and plots relating to data analyzed using a hyperplane algorithm, consistent with the present inventive concepts.

FIGS. 13A-C illustrate various graphs of recorded data and processed data, consistent with the present inventive concepts.

FIGS. 16A-D illustrate various graphs of recorded data and processed data, consistent with the present inventive concepts.

FIGS. 18A-C illustrate various graphs of recorded data and processed data, consistent with the present inventive concepts.

FIGS. 19A-E illustrate various perspective views of a portion of an implantable device, consistent with the present inventive concepts.

DETAILED DESCRIPTION OF THE DRAWINGS

Figure 1:
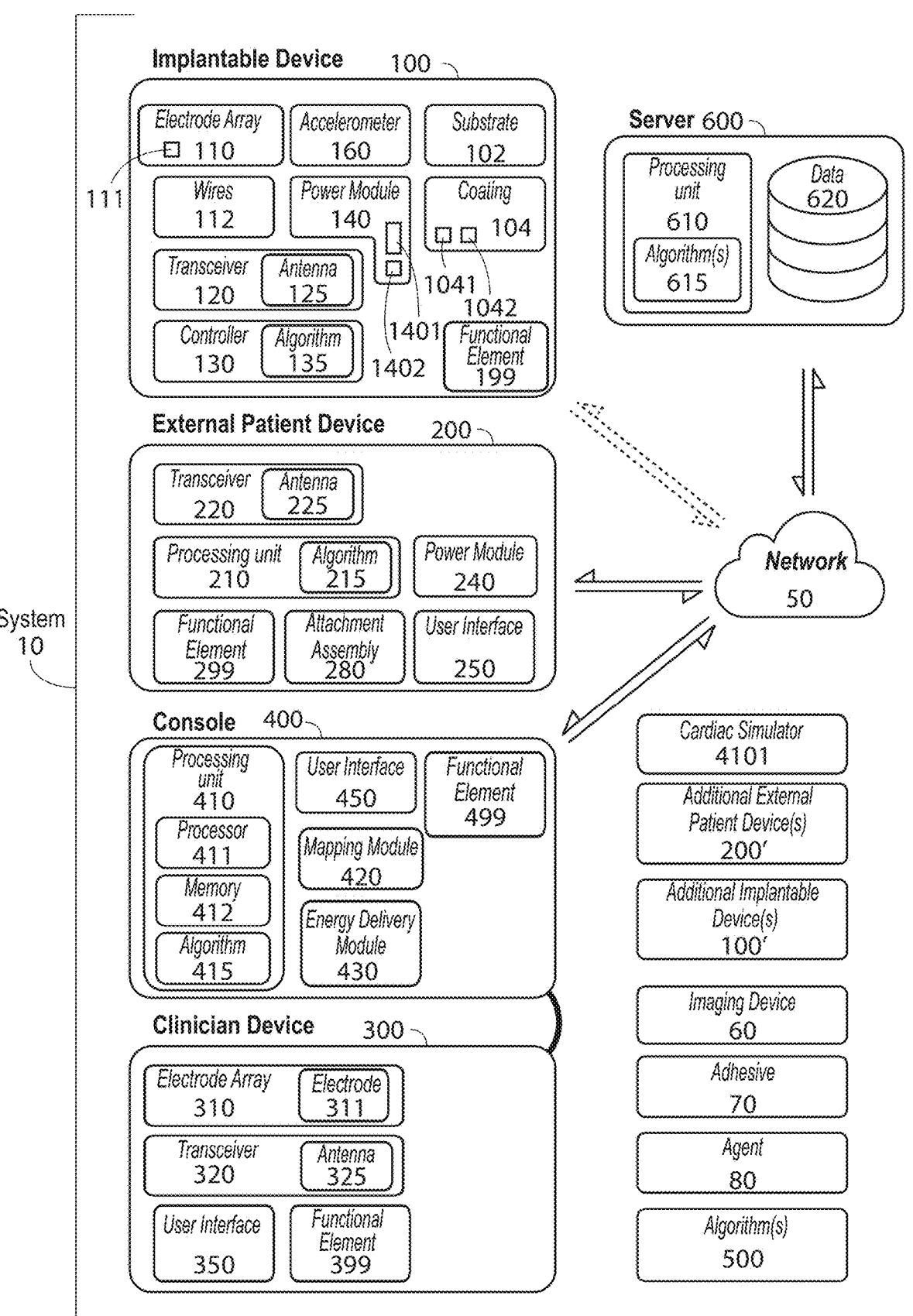
FIG. 1 illustrates a schematic view of a system for diagnosing and/or treating a patient, consistent with the present inventive concepts.

Reference will now be made in detail to the present embodiments of the technology, examples of which are illustrated in the accompanying drawings. Similar reference numbers may be used to refer to similar components. However, the description is not intended to limit the present disclosure to particular embodiments, and it should be construed as including various modifications, equivalents, and/or alternatives of the embodiments described herein.

It will be understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be further understood that, although the terms first, second, third, etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

It will be further understood that when a first element is referred to as being "in", "on" and/or "within" a second element, the first element can be positioned: within an internal space of the second element, within a portion of the second element (e.g., within a wall of the second element); positioned on an external and/or internal surface of the second element; and combinations of one or more of these.

As used herein, the term "proximate", when used to describe proximity of a first component or location to a second component or location, is to be taken to include one or more locations near to the second component or location, as well as locations in, on and/or within the second component or location. For example, a component positioned proximate an anatomical site (e.g., a target tissue location), shall include components positioned near to the anatomical site, as well as components positioned in, on and/or within the anatomical site.

Spatially relative terms, such as "beneath," "below," "lower," "above," "upper" and the like may be used to describe an element and/or feature's relationship to another element(s) and/or feature(s) as, for example, illustrated in the figures. It will be further understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g., rotated 90 degrees or at other orientations) and the spatially relative descriptors used herein interpreted accordingly.

The terms "reduce", "reducing", "reduction" and the like, where used herein, are to include a reduction in a quantity, including a reduction to zero. Reducing the likelihood of an occurrence shall include prevention of the occurrence. Correspondingly, the terms "prevent", "preventing", and "prevention" shall include the acts of "reduce", "reducing", and "reduction", respectively.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

The term "one or more", where used herein can mean one, two, three, four, five, six, seven, eight, nine, ten, or more, up to any number.

The terms "and combinations thereof" and "and combinations of these" can each be used herein after a list of items that are to be included singly or collectively. For example, a component, process, and/or other item selected from the group consisting of: A; B; C; and combinations thereof, shall include a set of one or more components that comprise: one, two, three or more of item A; one, two, three or more of item B; and/or one, two, three, or more of item C.

In this specification, unless explicitly stated otherwise, "and" can mean "or", and "or" can mean "and". For example, if a feature is described as having A, B, or C, the feature can have A, B, and C, or any combination of A, B, and C. Similarly, if a feature is described as having A, B, and C, the feature can have only one or two of A, B, or C.

As used herein, when a quantifiable parameter is described as having a value "between" a first value X and a second value Y, it shall include the parameter having a value of: at least X, no more than Y, and/or at least X and no more than Y. For example, a length of between 1 and 10 shall include a length of at least 1 (including values greater than 10), a length of less than 10 (including values less than 1), and/or values greater than 1 and less than 10.

The expression "configured (or set) to" used in the present disclosure may be used interchangeably with, for example, the expressions "suitable for", "having the capacity to", "designed to", "adapted to", "made to" and "capable of" according to a situation. The expression "configured (or set) to" does not mean only "specifically designed to" in hardware. Alternatively, in some situations, the expression "a device configured to" may mean that the device "can" operate together with another device or component.

As used herein, the term "threshold" refers to a maximum level, a minimum level, and/or range of values correlating to a desired or undesired state. In some embodiments, a system parameter is maintained above a minimum threshold, below a maximum threshold, within a threshold range of values, and/or outside a threshold range of values, such as to cause a desired effect (e.g., efficacious therapy) and/or to prevent or otherwise reduce (hereinafter "prevent") an undesired event (e.g., a device and/or clinical adverse event). In some embodiments, a system parameter is maintained above a first threshold (e.g., above a first temperature threshold to cause a desired therapeutic effect to tissue) and below a second threshold (e.g., below a second temperature threshold to prevent undesired tissue damage). In some embodiments, a threshold value is determined to include a safety margin, such as to account for patient variability, system variability, tolerances, and the like. As used herein, "exceeding a threshold" relates to a parameter going above a maximum threshold, below a minimum threshold, within a range of threshold values and/or outside of a range of threshold values.

As described herein, "room pressure" shall mean pressure of the environment surrounding the systems and devices of the present inventive concepts. Positive pressure includes pressure above room pressure or simply a pressure that is greater than another pressure, such as a positive differential pressure across a fluid pathway component such as a valve. Negative pressure includes pressure below room pressure or a pressure that is less than another pressure, such as a negative differential pressure across a fluid component pathway such as a valve. Negative pressure can include a vacuum but does not imply a pressure below a vacuum. As used herein, the term "vacuum" can be used to refer to a full or partial vacuum, or any negative pressure as described hereabove.

The term "diameter" where used herein to describe a non-circular geometry is to be taken as the diameter of a hypothetical circle approximating the geometry being described. For example, when describing a cross section, such as the cross section of a component, the term "diameter" shall be taken to represent the diameter of a hypothetical circle with the same cross sectional area as the cross section of the component being described.

The terms "major axis" and "minor axis" of a component where used herein are the length and diameter, respectively, of the smallest volume hypothetical cylinder which can completely surround the component.

As used herein, the term "functional element" is to be taken to include one or more elements constructed and arranged to perform a function. A functional element can comprise a sensor and/or a transducer. In some embodiments, a functional element is configured to deliver energy and/or otherwise perform a treatment on tissue (e.g., a functional element configured as a treatment element). Alternatively or additionally, a functional element (e.g., a functional element comprising a sensor) can be configured to record one or more parameters, such as a patient physiologic parameter; a patient anatomical parameter (e.g., a tissue geometry parameter); a patient environment parameter; and/or a system parameter. In some embodiments, a sensor or other functional element is configured to perform a diagnostic function (e.g., to gather data used to perform a diagnosis). In some embodiments, a functional element is configured to perform a therapeutic function (e.g., to deliver therapeutic energy and/or a therapeutic agent). In some embodiments, a functional element comprises one or more elements constructed and arranged to perform a function selected from the group consisting of: deliver energy; extract energy (e.g., to cool a component); deliver a drug or other agent; manipulate a system component or patient tissue; record or otherwise sense a parameter such as a patient physiologic parameter or a system parameter; and combinations of one or more of these. A functional element can comprise a fluid and/or a fluid delivery system. A functional element can comprise a reservoir, such as an expandable balloon or other fluid-maintaining reservoir. A "functional assembly" can comprise an assembly constructed and arranged to perform a function, such as a diagnostic and/or therapeutic function. A functional assembly can comprise an expandable assembly. A functional assembly can comprise one or more functional elements.

The term "transducer" where used herein is to be taken to include any component or combination of components that receives energy or any input, and produces an output. For example, a transducer can include an electrode that receives electrical energy, and distributes the electrical energy to tissue (e.g., based on the size of the electrode). In some configurations, a transducer converts an electrical signal into any output, such as: light (e.g., a transducer comprising a light emitting diode or light bulb), sound (e.g., a transducer comprising a piezo crystal configured to deliver ultrasound energy); pressure (e.g., an applied pressure or force); heat energy; cryogenic energy; chemical energy; mechanical energy (e.g., a transducer comprising a motor or a solenoid); magnetic energy; and/or a different electrical signal (e.g., different than the input signal to the transducer). Alternatively or additionally, a transducer can convert a physical quantity (e.g., variations in a physical quantity) into an electrical signal. A transducer can include any component that delivers energy and/or an agent to tissue, such as a transducer configured to deliver one or more of: electrical energy to tissue (e.g., a transducer comprising one or more electrodes); light energy to tissue (e.g., a transducer comprising a laser, light emitting diode and/or optical component such as a lens or prism); mechanical energy to tissue (e.g., a transducer comprising a tissue manipulating element); sound energy to tissue (e.g., a transducer comprising a piezo crystal); chemical energy; electromagnetic energy; magnetic energy; and combinations of one or more of these.

As used herein, the term "fluid" can refer to a liquid, gas, gel, or any flowable material, such as a material which can be propelled through a lumen and/or opening.

As used herein, the term "material" can refer to a single material, or a combination of two, three, four, or more materials.

It is appreciated that certain features of the inventive concepts, which are, for clarity, described in the context of separate embodiments, may also be provided in combination in a single embodiment. Conversely, various features of the inventive concepts which are, for brevity, described in the context of a single embodiment, may also be provided separately or in any suitable sub-combination. For example, it will be appreciated that all features set out in any of the claims (whether independent or dependent) can be combined in any given way.

It is to be understood that at least some of the figures and descriptions of the inventive concepts have been simplified to focus on elements that are relevant for a clear understanding of the inventive concepts, while eliminating, for purposes of clarity, other elements that those of ordinary skill in the art will appreciate may also comprise a portion of the inventive concepts. However, because such elements are well known in the art, and because they do not necessarily facilitate a better understanding of the inventive concepts, a description of such elements is not provided herein.

Terms defined in the present disclosure are only used for describing specific embodiments of the present disclosure and are not intended to limit the scope of the present disclosure. Terms provided in singular forms are intended to include plural forms as well, unless the context clearly indicates otherwise. All of the terms used herein, including technical or scientific terms, have the same meanings as those generally understood by an ordinary person skilled in the related art, unless otherwise defined herein. Terms defined in a generally used dictionary should be interpreted as having meanings that are the same as or similar to the contextual meanings of the relevant technology and should not be interpreted as having ideal or exaggerated meanings, unless expressly so defined herein. In some cases, terms defined in the present disclosure should not be interpreted to exclude the embodiments of the present disclosure.

Provided herein are systems, devices, and methods for providing therapy to a heart of a patient. The system can comprise one or more implantable devices. In some embodiments, the system includes one or more external devices, such as external devices that deliver power and/or data to one or more implantable devices. An implantable device can comprise: an anchor configured to maintain the position of the implantable device; at least one sensor configured to record electrical activity of the heart; and/or one, two, or more pacing electrodes configured to deliver stimulation energy to tissue of the heart, such as to treat an arrhythmia such as atrial fibrillation (AF). The system can include a controller that comprises one or more algorithms, such as an algorithm that initiates and/or adjusts delivery of energy to treat an arrhythmia of the patient.

Referring now to FIG. 1, a schematic view of a system for diagnosing and/or treating a patient is illustrated, consistent with the present inventive concepts. System 10 can comprise one or more devices (e.g., devices for a clinician to perform a procedure, devices for a patient to position proximate their body, and/or devices for implantation in the patient) which can be configured to monitor one or more patient parameters, diagnose one or more patient conditions, and/or to treat one or more patient conditions, such as to treat a condition based on one or more patient diagnoses determined by system 10. For example, system 10 can be configured to monitor, diagnose, and/or treat ("treat" herein) an arrhythmia such as atrial fibrillation (AF), a category of abnormally fast and/or "highly irregular" rhythm due to improper electrical activity in the atrial chambers of the heart, such as by monitoring the electrical activity of the patient's heart, and by pacing the muscular tissue in either or both the atrial chambers of the heart to restore sinus rhythm when fibrillation is detected. In another example, system 10 can be configured to treat supraventricular tachycardia (SVT), a category of abnormally fast and/or "regular or quasi-regular" rhythms due to improper electrical activity in the atrial chambers of the heart, such as by monitoring the electrical activity of the patient's heart, and by pacing the muscular tissue in either or both the atrial chambers of the heart to restore sinus rhythm when SVT is detected. In another example, system 10 can be configured to treat atrial tachycardia (AT), a common abnormally fast and regular arrythmia in the category of SVT due to improper electrical activity in the atrial chambers of the heart, such as by monitoring the electrical activity of the patient's heart, and by pacing the muscular tissue in either or both the atrial chambers of the heart to restore sinus rhythm when AT is detected. In another example, system 10 can be configured to treat both the typical and atypical forms of atrial flutter (AFL), which are common abnormally fast and regular arrythmias in the category of SVT due to improper electrical activity in the atrial chambers of the heart, such as by monitoring the electrical activity of the patient's heart, and by pacing the muscular tissue in either or both the atrial chambers of the heart to restore sinus rhythm when AFL is detected. System 10 can include one or more devices configured to be implanted, implantable device 100 (also referred to as ID 100 herein), which can be implanted into the patient for an extended period of time (e.g., at least 1 month, at least 3 months, and/or at least 6 months), such as when implanted by a clinician during a clinical procedure. In some embodiments, implantable device 100 comprises a short-term implant, such as when implantable device 100 is configured to be implanted for no more than 6 months, no more than 3 months, and/or no more than 1 month (e.g., implantable device 100 can be implanted for two or three weeks following cardiac surgery). In some embodiments, ID 100 is configured to be implanted during a cardiac surgical procedure (e.g., an open chest procedure), and ID 100 is configured to be placed on the epicardial surface and adhered thereto, such as with suture, compression, and/or surgical glue.

In some embodiments, system 10 comprises one or more externally-placed devices, external patient device 200, which can comprise one or more devices that are configured to monitor, diagnose, and/or treat a patient, such as from one or more locations outside the patient's body. Alternatively or additionally, external patient device 200 (also referred to as EPD 200) can be configured to communicate (e.g., wirelessly communicate) with implantable device 100 (also referred to as ID 100), such as to transfer data between EPD 200 and ID 100, and/or to transfer power from EPD 200 to ID 100. In some embodiments, ID 100 comprises two devices, a first device configured to be implanted proximate the patient's heart, as described herein, and a second device configured to be implanted at another location under the patient's skin (e.g., subcutaneously). In some embodiments, the second ID 100 (implanted subcutaneously) is configured similar to EPD 200 described herein, such as to transmit power and/or data to the first ID 100 (implanted proximate the patient's heart). In these embodiments, system 10 may include, or may not include, EPD 200. Alternatively or additionally, system 10 may include at least two IDs 100 (such as ID 100a and 100b shown in FIG. 1A), where a first ID 100 is configured as EPD 200 and to transmit power and/or data to a second ID 100, and also include an EPD 200, such as when EPD 200 is configured to transmit power to the first ID 100, for example, to recharge a power supply (e.g., a battery and/or a capacitor) of the first ID 100. In some embodiments, one or more IDs 100 and/or EPDs 200 can be operably connected via one or more conduits, not shown, but such as an electrical conduit that is tunneled beneath the skin of the patient (e.g., to connect a subcutaneously implanted ID 100 and/or EPD 200 to an ID 100 implanted proximate the heart).

System 10 can be configured to monitor for and/or to detect irregular or otherwise undesirable ("irregular" or "undesirable" herein) electrical conduction signals or patterns ("patterns" herein) in tissue and/or to deliver energy to the tissue to restore a desirable regular (e.g., healthy) electrical conduction pattern. In some embodiments, system 10 is configured to detect undesirable conduction patterns comprising regular but rapid patterns. System 10 can be configured to monitor the electrical activity of the heart (e.g., conduction patterns proximate the left and/or right atrium of the heart), and to detect the presence of irregular conduction patterns, such as conduction patterns indicative of AF and/or SVT. Additionally or alternatively, system 10 can deliver electrical energy (e.g., pacing pulses) to tissue exhibiting irregular conduction patterns, as well as to tissue surrounding that tissue, to alter the irregular conduction patterns. In some embodiments, system 10 is configured to deliver "multi-site" pacing, where pacing energy is delivered from two, three, four, or more electrodes positioned at different locations, such as different locations proximate the left atrium and/or the right atrium. For example, system 10 can be configured to deliver multi-site left-atrial pacing (i.e. delivery of energy to two left atrial tissue locations) configured to restore sinus rhythm in patients exhibiting irregular conduction patterns. In some embodiments, system 10 is configured to ablate tissue, such as by delivering energy configured to thermally ablate and/or irreversibly electroporate tissue. In these embodiments, system 10 can be further configured to also deliver pacing energy to tissue, such as multi-site pacing energy and/or other pacing energy, such as is described herein.

In some embodiments, system 10 is configured to deliver energy to the patient's heart (e.g., to treat a regular and/or an irregular arrhythmia such as atrial fibrillation, and/or other irregular heartbeat) at a level such that the energy delivery is not perceived by the patient, or at least minimally perceived by the patient (e.g., at a level below a pain threshold, such as a threshold of approximately 0.75 J). For example, system 10 can be configured to deliver energy at a level similar to the energy delivered by a pacemaker, such as between 5 mA and 20 mA, and/or less than 0.1 J. In some embodiments, this energy delivery comprises multiple site energy delivery as described herein (e.g., spatially distanced energy delivery). For example, multiple electrodes (e.g., at least three, four, or five electrodes) can be placed on the epicardium for delivery of the stimulation energy. These multiple electrodes can be spatially distributed to gain sufficient coverage of the heart chamber to achieve effective therapy (e.g., to effectively pace terminate atrial fibrillation and/or other arrhythmia). In some embodiments, less than 6 mJ (e.g., less than 5 mJ or less than 4 mJ) of energy can be delivered at each epicardial site (e.g., over a period of approximately one second), such as to terminate atrial fibrillation in the patient.

System 10 can include one or more devices for use by a clinician during a clinical procedure, clinician device 300. Clinician device 300 (also referred to as CD 300) can comprise one or more delivery devices, such as a kit of devices configured to enable the clinician to perform an implantation procedure for implanting ID 100 into the patient. For example, CD 300 can comprise one or more delivery catheters, such as when ID 100 is configured to be implanted during a minimally invasive procedure, such as an interventional procedure performed in a catheterization laboratory (often referred to as a "cath lab"). For example, CD 300 can comprise one or more tools for percutaneous delivery of ID 100 in the patient's vasculature, and one or more tools for transvascular delivery of ID 100 into locations outside of the patient's vasculature (e.g., into the pericardial space, such as onto the epicardial surface). Alternatively or additionally, CD 300 can comprise one or more surgical tools (e.g., minimally invasive tools) for surgically implanting ID 100 (e.g., a surgical access kit for use in an operating room). For example, CD 300 can comprise one or more surgical tools for percutaneous delivery of ID 100 (e.g., a needle-based tool for insertion of ID 100 into the pericardial space). In some embodiments, ID 100 comprises a first geometry where ID 100 is in an undeployed state, such as a geometry comprising a collapsed, folded, or otherwise undeployed geometry configured to allow ease of insertion into the patient. ID 100 can be configured to transition from the first geometry into a second geometry in which ID 100 is in an expanded or otherwise deployed state. In some embodiments, ID 100 is configured to be deployed from a coronary vessel (e.g., through the tissue wall) and implanted along the epicardial surface (e.g., during an interventional procedure), such as is described in detail herein. For example, ID 100 can be deployed from a vessel (e.g., a coronary vessel) selected from the group consisting of: the coronary sinus; the Great Cardiac Vein; the Vein of Marshall; the Azygos vein; a side-branch that anastomoses the coronary sinus, for example, side branches that lie proximate a desired deployment location such as the epicardial surface of the left atrium; and combinations of these. In some embodiments, ID 100 can be configured to be deployed by a robotic delivery device, such as a magnetically-driven robotic device.

In some embodiments, CD 300 includes one or more tools for providing epicardial access (e.g., subxiphoid percutaneous epicardial access), such as to allow a clinician to implant ID 100 on or otherwise proximate an epicardial surface. CD 300 can be configured to prevent (or at least limit the likelihood) of ventricular puncture. CD 300 can be constructed and arranged to enable the clinician to perform a "dry tap" of the epicardial space (e.g., without allowing the needle to penetrate the ventricular tissue). In some embodiments, CD 300 includes one or more devices for positioning a visualizable device, such as a visualizable portion of guidewire or a lead (e.g., a visualizable lead, such as a lead visualizable under fluoroscopy or ultrasound) proximate the lateral margin of the roof of the right atrium (RA). In some embodiments, CD 300 includes a needle and mechanical or other stopping mechanism configured to prevent the needle from advancing into ventricular tissue. After placement, this visualizable device can assist the clinician by providing a visualizable marker indicating the location of the lateral RA boundary. In some embodiments, CD 300 includes one or more devices for positioning a visualizable device proximate the posterior wall of the left atrium (LA). After placement, this visualizable device can assist the clinician by providing a visualizable marker indicating the location of the posterior LA boundary. In some embodiments, CD 300 includes one or more devices for positioning a visualizable device proximate the interatrial septum between the RA and LA. After placement, this visualizable device can assist the clinician by providing a visualizable marker indicating the location of the interatrial septum. In some embodiments, CD 300 includes one or more devices for positioning a visualizable device proximate the apex of the right ventricle (RV). After placement, this visualizable device can assist the clinician by providing a visualizable marker indicating the location of the RV boundary. In some embodiments, CD 300 includes one or more devices for positioning a lead (e.g., a visualizable lead, such as a lead visualizable under fluoroscopy or ultrasound) proximate the apex of the left ventricle (LV). After placement, this lead can assist the clinician by providing a visualizable marker indicating the location of the LV boundary. In some embodiments, system 10 is configured to image the RV, such as with an angiogram or other visualization method (e.g., as provided by imaging device 60 described herein), such as to assist the clinician by providing one or more images that show the border of the RV and the pericardial space. In some embodiments, system 10 is configured to image the LV, such as with an angiogram or other visualization method (e.g., as provided by imaging device 60 described herein), such as to assist the clinician by providing one or more images that show the border of the LV and the pericardial space.

In some embodiments, CD 300 includes a device (e.g., a needle) configured to provide a signal used to identify the pericardial juncture (e.g., by providing a bioimpedance signal). For example, the needle can include an electrode proximate the distal end of the needle. Alternatively or additionally, the needle can comprise an electrically conductive material, and at least a proximal portion of the needle can be insulated such that the distal tip of the needle comprises the electrode. In some embodiments, CD 300 comprises one or more devices configured to be positioned within the coronary sinus, perforate the coronary sinus, and enter the pericardial space. System 10 can comprise one or more visualizable agents, agent 80 shown. In some embodiments, CD 300 is constructed and arranged to inject agent 80 (e.g., a radiopaque material such as contrast) into the pericardial space. For example, device 300 can be configured to inject approximately 10 mL of a contrast-based agent 80 into the pericardial space.

In some embodiments, clinician device 300 comprises a programmer configured to transfer a set of parameters (e.g., a "program") to one or more of implantable device 100 and/or external patient device 200. In some embodiments, external patient device 200 can transfer programs to implantable device 100. A program can comprise a set of parameters, such as stimulation parameters which implantable device 100 will follow when stimulating the patient, such as described herein. In some embodiments, algorithm 135 is configured to cause implantable device 100 to stimulate the patient based on a program received from EPD 200 and/or clinician device 300.

System 10 can include one or more consoles, console 400 shown. Console 400 can operably connect to CD 300 and can be configured to facilitate one or more processes, energy deliveries, data collections, data analyses, data transfers, signal processing, and/or other functions ("functions" herein) of system 10. In some embodiments, system 10 is constructed and arranged to map electrical activity within the body of a patient (e.g., to map electrical activity of the patient's heart), such as when CD 300 comprises a mapping catheter and console 400 comprises mapping module 420. Mapping module 420 can be configured to record and process mapping signals recorded by CD 300. For example, mapping module 420 can be configured to characterize conduction patterns and/or signal morphologies, such as to classify them (e.g., via algorithm 415 described herein) into arrythmia types, such as AF, AT, AFL, and the like, both typical and atypical. In some embodiments, implantable device 100 and/or EPD 200 are similarly configured to characterize conduction patterns and/or signal morphologies, for example, by processing signals recorded by electrode array 110 (e.g., processing via algorithms 135 and/or 215). In some embodiments, system 10 is constructed and arranged to ablate tissue (e.g., ablate cardiac tissue to treat AF). In these embodiments, console 400 comprises energy delivery module 430. Energy delivery module 430 can be configured to deliver ablative energy to tissue, such as via one or more energy delivery elements (e.g., electrodes, ultrasound transducers, light-emitting elements, and the like) of CD 300. In some embodiments, system 10 is constructed and arranged to stimulate tissue, for example, by delivering stimulation energy via one or more electrodes 311 and/or other energy delivery elements of clinician device 300 (e.g., as described herein). Energy delivery module 430 can be configured to deliver energy in the form of stimulation pulses that stimulate tissue. Energy delivery module 430 can deliver stimulation pulses via any one or more single electrodes 311, and/or via one or more sets (e.g., pairs) of electrodes 311 at any given instant and/or at any frequency. In some embodiments, stimulation pulses are delivered as a sequence of pulses, such as a sequence of pulses that are delivered simultaneously and/or asynchronously, and/or regularly and/or irregularly. The stimulation pulses can be delivered across a plurality of operably connected electrodes 311, where each electrode 311 can be positioned at prescribed (e.g., clinician and/or system 10 determined, as described herein) locations about a chamber and/or chambers of the heart. These sequences of pulses can be controlled either manually and/or by an algorithm (e.g., algorithm 415 described herein), such as an algorithm that determines the location and the instances in time to deliver stimulation, such as a determination that is based on the measured state of a prescribed chamber's conduction pattern. Console 400 can include processing unit 410, which can be configured to perform one or more functions of console 400 (e.g., as described hereabove). Processing unit 410 can include processor 411, memory 412, and/or algorithm 415, each as shown. In some embodiments, memory 412 stores instructions to perform algorithm 415. Processing unit 410 can be constructed and arranged to execute algorithm 415 and to thereby execute one or more functions of console 400. In some embodiments, console 400 includes one or more user interfaces, user interface 450. In some embodiments, console 400 includes one or more functional elements, functional element 499 shown. Functional element 499 can include one or more sensors and/or transducers.

In some embodiments, console 400 is configured to perform a diagnostic interrogation of the morphology of cardiac activity of the patient, such as to provide a diagnostic interrogation of AF and/or SVT. For example, algorithm 415 can analyze electrical activity of the patient's heart to determine a treatment plan including selection and configuration of one or more components of system 10 to optimize treatment of the patient. In some embodiments, algorithm 415 is configured to process one or more electrograms (e.g., electrograms recorded by system 10 and/or imported into system 10) to produce a 3D model of the electrical activity of at least a portion of the heart. For example, algorithm 415 can produce 3D models that can be displayed (e.g., via user interface 450) to show the electrical conduction patterns and/or conduction timing of a portion of the heart (e.g., one or more chambers of the heart).

In some embodiments, algorithm 500 is configured to determine a treatment plan, such as to identify one or more portions of cardiac tissue to be treated by system 10, such as tissue to be ablated by clinician device 300. In some embodiments, one or more treatment locations determined by algorithm 500 are based on future therapy to be delivered by system 10, such as spatiotemporal resynchronization therapy (SRT) that will be delivered by ID 100. In some embodiments, algorithm 500 determines the treatment plan based on signals recorded from ID 100, such as when ID 100 is implanted prior to an ablation step and/or prior to an ablation procedure, for example when ID 100 is implanted in a first clinical procedure, and a second clinical procedure (e.g., an ablation procedure) is performed at a later date, such as at least one month, or at least six months later. In some embodiments, the treatment plan is based on signals recorded between the first procedure and the second procedure.

The implantation locations of each of the electrodes 111 can be: determined automatically by system 10, determined by a clinician, and/or determined in a semi-automated way based on clinician and system 10 input. In some embodiments, a pacing diagnostic procedure is performed in which energy is delivered by an electrode (e.g., an electrode 311 of clinician device 300, an electrode 111 of ID 100, and/or other electrode) that is positioned in a tissue location temporarily, such as to assess the impact (the pacing impact) of the energy delivery at that location (e.g., an epicardial or other cardiac location). In these embodiments, a set of electrode 111 implant locations can be determined. In some embodiments, additional criteria can be used to determine the electrode 111 implant locations, such as clinical criteria, anatomical criteria, geometric criteria, criteria derived in simulations, and/or other criteria. These additional criteria can be used cooperatively with the criteria collected in the pacing diagnostic procedure to determine the implant locations for the electrodes 111.

System 10 can include one or more imaging devices, imaging device 60. Imaging device 60 can comprise an imaging device selected from the group consisting of: an X-ray device such as a fluoroscopy device; a CT scanner device; an MRI device; an ultrasound imaging device; and combinations of these.

ID 100 can comprise one or more arrays of functional elements (e.g., sensors and/or transducers), electrode array 110, comprising one, two or more elements, electrodes 111. Electrode array 110 can comprise multiple configurations. Electrode array 110 can be constructed and arranged to be implanted on the epicardial surface of the heart, for example, on the epicardial wall proximate the left atrium. Alternatively or additionally, at least a portion of electrode array 110 (e.g., at least one electrode 111) can be implanted in a vessel (e.g., a coronary vessel), such as the coronary sinus, the Vein of Marshall, the Azygos vein, and/or another vessel proximate the heart. In some embodiments, at least a portion of electrode array 110 is implanted on the endocardial surface, such as within the left atrium or right atrium of the heart, for example, for example, on the septum between the left and right atrium. In some embodiments, at least a portion of electrode array 110 is positioned within the left atrial appendage (e.g., as part of a left atrial appendage closure device). Electrodes 111 can comprise pacing electrodes configured to deliver electrical stimulation energy to patient tissue (e.g., tissue of the heart). Additionally or alternatively, electrodes 111 can comprise sensing electrodes configured to record electrical activity of tissue (e.g., electrical activity of the heart). Electrodes 111 can be configured to deliver electrical stimulation and/or to sense electrical activity in unipolar and/or multipolar (e.g., bipolar) configurations, such as when two electrodes 111 comprise a pair of electrodes configured to operate in a source and sink arrangement. In some embodiments, electrode array 110 is fixedly attached to one or more flexible membranes, substrate 102. In some embodiments, substrate 102 comprise a single layer membrane. In some embodiments, substrate 102 comprises two or more membrane layers. Substrate 102 can comprise an elastomeric material, for example, a material selected from the group consisting of: poly(lactic-co-glycolic) acid (PLGA); silicone (PDMS); liquid crystal polymers; polyimide; polyurethane (PU); thermoplastic polyurethane (TPU); and combinations of these. In some embodiments, substrate 102 comprises a fabric mesh, such as a polyester mesh. In some embodiments, ID 100 can comprise an anchoring element, such as anchoring element 105 described herein. In some embodiments, substrate 102 comprises a flexible material. In some embodiments, substrate 102 comprises a stretchable material, for example, a material that can stretch at least 5% and/or a material that stretches no more than 200%. In some embodiments, substrate 102 can comprise one or more holes constructed and arranged to cause and/or enhance capillary action of tissue into substrate 102.

In some embodiments, one or more components of ID 100 (e.g., the components on the outer surfaces of ID 100 which will be exposed to the environment within the body when implanted) comprise biocompatible materials. In some embodiments, one or more components of ID 100 are at least partially encapsulated within substrate 102, for example, electrode array 110 can be positioned between two or more layers of substrate 102. In some embodiments, at least a portion of each electrode 111 of electrode array 110 extends through a layer of substrate 102 (e.g., an outer layer) such that at least a surface portion of electrode 111 is exposed to the body when ID 100 is implanted (e.g., such that ID 100 can be positioned with one or more electrodes 111 (e.g., all electrodes 111) in contact with the epicardial wall). In some embodiments, electrode array 110, and/or other electronic components of ID 100 can comprise one or more elastomeric materials. Alternatively or additionally, electrode array 110, and/or other electronic components of ID 100 can comprise one or more non-elastomeric materials. In some embodiments, substrate 102 comprises an elongate tubular geometry, such as when substrate 102 comprises a shaft similar to a catheter shaft with one or more electrodes positioned thereon.

In some embodiments, electrodes 111 comprise a coating and/or a surface treatment (either or both, "coating" herein), such as a coating that is configured to enhance the recording ability of ID 100 via electrodes 111. For example, electrode 11 can comprise one or more coatings that are configured to increase the surface area of electrodes 111, such as to enhance the recording ability of electrodes 111, such as by lowering the source impedance of electrodes 111. Coatings can reduce the impedance and effects of the half-cell potential that occur from large surface areas of noble metals. A balance of low input impedance and reduced capacitive effects are needed here. Consider that small electrodes are noisy due to high source impedance. In some embodiments, electrodes 111 can comprise a coating configured to reduce the electrode-tissue interface impedance, for example to improve recorded signal integrity and/or to improve energy transfer efficiency.

Electrode array 110 can comprise an array surface area (e.g., the surface area defined by the outside boundary of array 110, and/or the convex hull of electrodes 111 of ID 100) of at least 6.5 cm$^2$. In some embodiments, electrode array 110 can comprise a surface area greater than or equal to at least 12% of the epicardial surface of the right atrium of the heart and/or the left atrium of the heart. System 10 can comprise multiple implantable devices 100 in various sizes and shapes (e.g., various array 110 sizes), such as when provided in a kit form such that a clinician can select which implantable device 100 of a kit of implantable devices 100 to implant. The selection made can be based on one or more patient parameters, such as the size of the patient's heart (e.g., the size of an atrium and/or a ventricle of the patient's heart). In some embodiments, the size of array 110 of a particular ID 100 is proportional to the amount of tissue through which ID 100 can manipulate the electrical activity of the heart (e.g., to control and/or direct the propagation of cardiac activation of the tissue). In some embodiments, ID 100 comprises a conformable and/or an adjustable construction, for example when electrode array 110 is configured to transition from a compact geometry to an expanded geometry, such as is described in reference to FIGS. 19A-E and otherwise herein. In some embodiments, one or more ID 100 can be implanted at a location selected to treat a particular disease or ailment. For example, ID 100 can be implanted proximate the left atrium (e.g., on the epicardial surface) to deliver stimulation energy to treat atrial fibrillation. Alternatively or additionally, ID 100 can be implanted proximate a ventricle of the heart (e.g., on the epicardial surface) to deliver stimulation energy to treat ventricular tachycardia and/or ventricular fibrillation. In some embodiments, at least one electrode 111 is implanted in each chamber of the heart (e.g., at least one ID 100 is implanted in each chamber of the heart), such that system 10 can sense and/or pace from within each chamber.

In some embodiments, ID 100 comprises multiple devices, such as at least 5, or at least 10 devices. In these embodiments, multiple implantable devices 100 can be configured to be implanted in a distributed manner, for example, evenly distributed across one or more portions of the epicardial surface. In some embodiments, multiple devices 100 are configured to treat the patient in a coordinated fashion, such as to deliver energy to the cardiac tissue in a pattern based on the location of each individual ID 100 (e.g., relative to each other and/or the cardiac tissue). In some embodiments, ID 100 can comprise multiple devices, such as two, three, or more implantable devices 100. In some embodiments, multiple devices 100 are configured to collectively treat a patient with multiple arrhythmias in a coordinated fashion, such as to deliver energy to the right and/or the left atrium to treat AF and/or SVT, and/or to deliver energy to the right and/or the left ventricle to treat other arrhythmias. For example, the multiple devices 100 can each deliver energy as needed (e.g., as determined by a treatment plan of system 10, described herein), such as when the device 100 closest to the source of an arrhythmia is selected to deliver energy to treat that arrhythmia. In some embodiments, at least one of a set of multiple implantable devices 100 can be configured to be implanted in one or more locations selected from the group consisting of within the right atrium, such as affixed to the endocardial wall of the right atrium; within the left atrium, such as affixed to the endocardial wall of the left atrium; within the left and/or right ventricle; proximate one or more pulmonary veins, such as within and/or partially surrounding a pulmonary vein; on the endocardial surface proximate the left and/or right atrium, the left and/or right ventricle, a pulmonary vein, and/or another anatomic landmark; within a coronary vessel; embedded into cardiac tissue, such as between the endocardial and epicardial surface; and combinations of these.

In some embodiments, one or more conductive portions (e.g., conductive surfaces) of ID 100 (e.g., conductive portions of electrode array 110) are positioned on device 100 to be directed towards tissue to be stimulated when ID 100 is implanted (e.g., directed towards cardiac tissue), and one or more nonconductive portions of ID 100 are positioned on device 100 to be directed toward tissue to be insulated from stimulation energy delivered by ID 100 (e.g., directed toward the pericardium). For example, ID 100 can be configured to be implanted on the epicardial surface with the "bottom" of ID 100 directed towards the epicardial surface, and electrodes 111 can be positioned on the bottom of ID 100 and insulated from the top of ID 100, such as to prevent unintended stimulation of the phrenic nerve, the pericardium, and/or other electrically active thoracic structures. In some embodiments, ID 100 can comprise a cover configured to insulate one or more portions of ID 100 from tissue.

ID 100 can comprise controller 130, which can be configured to perform various functions of ID 100. Controller 130 can comprise a microprocessor, memory, and other components that can be constructed and arranged to control, perform, and/or otherwise enable one or more functions of ID 100. In some embodiments, controller 130 comprises one or more algorithms, algorithm 135 shown. In some embodiments, controller 130 comprises a memory for storing instructions to perform algorithm 135. Controller 130 can be constructed and arranged to execute algorithm 135 and to thereby execute one or more functions of ID 100. In some embodiments, each electrode 111 of electrode array 110 is independently addressable (e.g., electrically connected to at least two wires, such as ground and power or data, between each electrode and controller 130), such that signals (e.g., data and/or power) can be transmitted between controller 130 and each electrode 111 individually or collectively. Alternatively or additionally, controller 130 and/or electrode array 110 can be configured in a multiplexed arrangement, such that each electrode 111 can be individually addressed via a multiplexing component.

In some embodiments, controller 130 is configured to record electrical activity from one or more electrodes 111 (e.g., one or more electrodes 111 configured as sensing electrodes). Additionally or alternatively, controller 130 can be configured to provide stimulation signals to be delivered to the patient via one or more electrodes 111 (e.g., one or more electrodes 111 configured as pacing electrodes). In some embodiments, electrode array 110 comprises a set of electrodes 111 configured as pacing electrodes, and a set of electrodes 111 configured as sensing electrodes. Alternatively or additionally, controller 130 can be configured to alternate between pacing and sensing from an electrode 111 of electrode array 110 (e.g., in a multiplexed arrangement). In some embodiments, controller 130 is configured to simultaneously sense and pace from a given electrode 111. In some embodiments, multiple electrodes 111 can be multiplexed such as to sense (e.g., record signals) from one electrode 111 relative to a plurality of other electrodes 111 that collectively serve as a sensing reference. For example, the collective reference can be formed by the distance-weighted average of each of the electrodes 111 in the collected-reference (the collective "–" signal-reference) relative to the one measurement electrode (the one "+" signal-measurement). Additionally or alternatively, a similar arrangement can be provided for electrodes 111 delivering stimulation energy, such as when stimulation energy is delivered between a set of electrodes 111 (e.g., configured as an anode or a cathode) and a single electrode 111 (e.g., configured as a cathode or anode, respectively).

In some embodiments, ID 100 comprises a membrane or other material, coating 104, which can surround at least a portion of the surface of one or more components positioned on and/or within substrate 102. Coating 104 can comprise a biocompatible material, for example, a coating selected from the group consisting of: a silicone (PDMS) coating; a parylene coating; a water-based coating; a resin coating; a chemical coating; a steroidal coating; and combinations of these. Coating 104 can be configured to prevent irritation of the tissue onto which ID 100 is implanted, for example, to prevent an allergic reaction. In some embodiments, coating 104 comprises a bio-adhesive configured to permanently and/or semi-permanently adhere ID 100 to tissue (e.g., to the epicardial wall). For example, coating 104 can comprise a hydrogel (e.g., a hydrogel adhesive). Alternatively or additionally, system 10 can include adhesive 70, configured to be applied between ID 100 and tissue. In some embodiments, adhesive 70 is electrically conductive. In some embodiments, adhesive 70 comprises a UV activated adhesive. Adhesive 70 can comprise an injectable adhesive, for example, an injectable adhesive comprising a durometer under a threshold (e.g., a sufficiently soft adhesive). Adhesive 70 can comprise a biocompatible adhesive. In some embodiments, coating 104 can comprise a hollow tube, sheath 1041, configured to surround shaft 1021 of ID 100. Sheath 1041 can comprise one or more openings, openings 1042 through which electrodes 111 can contact tissue.

In some embodiments, ID 100 comprises one or more securing and/or stabilizing elements, anchoring element 105. Anchoring element 105 can be configured to secure, affix, stabilize, prevent (or at least limit) migration of, or otherwise prevent or limit unwanted motion of ID 100 ("secure" herein) before, during, and/or after implantation of device 100. In some embodiments, anchoring element 105 comprises a releasable and/or re-securable securing mechanism, such that ID 100 can be repositioned and/or removed (e.g., repositioned by a clinician using clinician device 300). Anchoring element 105 can be configured to interact with an anatomical feature to secure ID 100, such as by pushing against the pericardial sac to force ID 100 onto the epicardial wall. In some embodiments, anchoring element 105 comprises a material configured to promote tissue ingrowth and/or tissue overgrowth, such as to secure ID 100 as tissue growth interacts with anchoring element 105. For example, anchoring element 105 can comprise a fabric mesh.

In some embodiments, the various components of ID 100 are interconnected by one or more conduits, wires 112. In some embodiments, wires 112 comprise conductive routing filaments, for example, one or more conductive traces, such as one or more traces within and/or on a circuit board (e.g., a flexible circuit board). In some embodiments, wires 112 comprise traces within and/or on substrate 102. In some embodiments, electrode array 110 comprises one or more wires 112, for example, when electrodes 111 are electrically interconnected by wires 112. Wires 112 comprising conductive routings can each comprise a liquid metal routing, for example, a routing liquid phase eutectic gallium. In some embodiments, conductive traces are applied to substrate 102 (e.g., during a manufacturing process) with methods that include the manipulation of nanoparticles. For example, conductive traces can be formed such that wires 112 comprise nanowires consisting of graphene and/or silver. In some embodiments, wires 112 (configured as conductive traces of substrate 102) comprises a geometry configured to minimize Van der Waals, tensile, compressive, and/or other undesired forces, such as when wires 112 comprise a wave-like geometry (e.g., a sinusoidal geometry). The geometry of wires 112 can be configured such that wires 112 maintain a high level of conductivity, such when under strain.

ID 100 can include transceiver 120. Transceiver 120 can be configured to communicate (e.g., wirelessly communicate) with one or more other components of system 10, for example, one or more additional implanted devices 100', as well as EPD 200, CD 300, console 400, and/or another component of system 10. Transceiver 120 can comprise a receiving and/or transmitting interface, antenna 125. Antenna 125 can be positioned on and/or embedded within substrate 102. In some embodiments, electrode array 110 comprises antenna 125, for example, when wires 112 of electrode array 110 are constructed and arranged to function as an antenna. Antenna 125 can comprise various shapes, for example, antenna 125 can comprise planar micro coils configured in various shapes. Antenna 125 can be configured as illustrated in FIG. 6B described herein.

ID 100 can include power module 140. Power module 140 can include one or more power-generating, power-harvesting, power-storing, power-transferring (e.g., via wireless power transfer) and/or other power-supplying components configured to deliver energy to ID 100. Power module 140 can be configured to provide power to one or more components of ID 100. In some embodiments, power module 140 comprises one or more batteries, capacitors, and/or other power-storing devices. In some embodiments, power module 140 comprises a solid-state battery, such as a miniature solid-state battery. In some embodiments, power module 140 comprises a rechargeable battery. In some embodiments, power module 140 comprises one or more capacitors. In some embodiments, power module 140 comprises at least one battery and at least one capacitor. In some embodiments, ID 100 does not include a battery (i.e. a source of power that is generated by an electrochemical reaction), a "battery-less design" herein, for example, when power module 140 is configured to harvest power (e.g., configured to harvest power transmitted wirelessly from EPD 200), and power module 140 is configured to store and directly provide the harvested power to power the various components of ID 100. Power module 140 can be constructed and arranged to "harvest" power from kinetic motion, for example, from kinetic motion of heart tissue when at least a portion of ID 100 is positioned on and/or within the heart. In some embodiments, power module 140 comprises one or more piezo electric components configured to convert kinetic energy to electrical energy.

In some embodiments, ID 100 can comprise patient sensor 160 shown. Patient sensor 160 can comprise one, two or more sensors selected from the group consisting of: an electrical sensor, such as a sensor configured to record an electrogram; a temperature sensor; accelerometer; position sensor; gravimetric sensor; pressure sensor; strain gauge; acoustic sensor; and combinations of these. System 10 can be configured to monitor one or more patient parameters based on information recorded by patient sensor 160, such as heartbeat, patient position, and/or patient activity.

In some embodiments, system 10 is configured to monitor for fluid in the lungs of the patient. For example, patient sensor 160 can comprise an impedance sensor and/or an ultrasonic sensor configured to measure the level and/or detect the presence of fluid in the lungs.

ID 100 can include one or more functional elements, functional element 199 shown. Functional element 199 can comprise one, two, or more sensors selected from the group consisting of: pressure sensor such as blood pressure sensor; acoustic sensor; respiration sensor; gas sensor such as blood gas sensor; flow sensor such as blood flow sensor; temperature sensor; pH sensor; optical sensor; impedance sensor; and combinations of these. In some embodiments, functional element 199 comprises one, two, or more transducers, such as an optical transducer (e.g., an LED).

System 10 can be configured to both monitor one or more patient parameters and to treat the patient based on the monitored parameters (e.g., based on an analysis of the monitored parameters). For example, system 10 can be configured to monitor (e.g., via electrode array 110) and analyze (e.g., via controller 130) electrograms recorded by ID 100, (e.g., unipolar and/or multipolar, for example, bipolar, modes of electrogram recording) and to pace and/or otherwise stimulate tissue if atrial fibrillation (AF) is detected, for example as described herein. In some embodiments, system 10 is configured to monitor and/or record one, two, or more of electrophysiological activity, patient temperature, heartbeat information, and/or another patient parameter. In some embodiments, ID 100 is configured to stimulate tissue based on data recorded and/or analyzed by mapping module 420 of console 400. For example, mapping module 420 can be configured to identify irregular conduction patterns within one or more locations of cardiac tissue, as described herein, and to determine a set of stimulation parameters to be delivered by ID 100 to stimulate the tissue to treat (e.g., correct) the irregular conduction patterns.

In some embodiments, electrode array 110 is positioned along (e.g., on and/or within) shaft 1021, such as a shaft 1021 configured in a spiral geometry. Additionally or alternatively, shaft 1021 can comprise a resiliently biased geometry, such as when shaft 1021 is configured in a resiliently biased spiral geometry. In some embodiments, substrate 102 comprises a nickel titanium alloy and/or other shape memory material, such as when substrate 102 comprises a shape memory inner layer surrounded by one or more layers of polymers or other flexible materials. In some embodiments, substrate 102 comprises an elongate geometry (e.g., shaft 1021), and the one or more wires 112 extend along (e.g., on the surface and/or within) substrate 102, for example, connecting each electrode 111 to controller 130 positioned at one end of shaft 1021. In some embodiments, controller 130 comprises various other components of ID 100, such as transceiver 120, power module 140, patient sensor 160, and the like.

In some embodiments, wires 112 and/or a portion of substrate 102 are configured as at least a portion of antenna 125, such as when shaft 1021 is configured in a spiral geometry (such as a spiral geometry described herein). For example, substrate 102 can comprise a conductive portion (e.g., an inner core of shaft 1021), such as a portion with a gold conductive core with a nickel titanium cladding, or a nickel titanium core with a platinum iridium cladding. In these embodiments, this conductive core of shaft 1021 can be electrically insulated, such as when the core is surrounded by an insulative material, such as an insulative polymer.

In some embodiments, one or more portions of ID 100 (e.g., one, two, or more components of ID 100) can be bioabsorbable and/or bioresorbable ("bioabsorbable" herein). For example, ID 100 can comprise a device including two or more electrodes 111 operably attached to antenna 125, that is configured to harvest RF energy (e.g., RF energy transmitted from EPD 200) and directly stimulate tissue by providing the harvested energy to electrodes 111 and electrodes 111, antenna 125 and/or the associated electrical traces of ID 100 can comprise a bioabsorbable conductive material, such as tungsten-coated magnesium (W/Mg). ID 100 can comprise one or more other components that comprise bioabsorbable magnesium. In some embodiments, electrodes 111, antenna 125, and/or the associated electrical traces of ID 100 are positioned on and/or within a bioabsorbable patch, such as a bioabsorbable patch configured to be attached to the epicardial surface with bioabsorbable suture.

External patient device 200 (EPD 200) can be constructed and arranged to be worn by the patient, such as when positioned on the skin of the patient (e.g., when EPD 200 is temporarily adhered or otherwise temporarily attached to the patient's skin), and/or when inserted in and/or otherwise attached to the patients clothing. Alternatively or additionally, EPD 200 can be held against the patient, such as when held against the patient's skin and/or clothing (e.g., by the patient and/or by a patient attachment device). For example, EPD 200 can be configured to be held against the patient, proximate ID 100, while EPD 200 communicates with ID 100 (e.g., for a brief period of time, such as less than 60 seconds). In some embodiments, EPD 200 includes attachment assembly 280. Attachment assembly 280 can include an adhesive, such as an adhesive patch, configured to adhere EPD 200 to the patient's skin for at least 6 hours, such as at least 12 hours, or at least 24 hours (e.g., before the adhesive patch must be replaced). Alternatively or additionally, attachment assembly 280 can comprise a harness, clip, specialized garment, or other non-adhesive based tool for positioning EPD 200 proximate the patient (e.g., proximate the location where ID 100 is implanted in the patient). For example, attachment assembly 280 can comprise a chest strap constructed and arranged to hold EPD 200 over the patient's heart, for example, when ID 100 is implanted onto the epicardial surface of the patient's left atrium. In some embodiments, EPD 200 comprises a device that is implanted subcutaneously or at another internal body location. Alternatively, one or more portions of EPD 200 are implanted in the patient and one or more portions are positioned external to the patient.

EPD 200 can include transceiver 220. Transceiver 220 can be configured to communicate (e.g., wirelessly communicate) with one or more components of system 10, for example, one or more implanted devices 100, and/or one or more additional external patient devices 200', as well as CD 300, console 400, and/or other components of system 10. Transceiver 220 can comprise a receiving and/or transmitting interface, antenna 225. EPD 200 can be constructed and arranged to transmit power and/or data to one or more implantable devices 100, such as by transmitting a radio frequency (RF) energy from antenna 225, through the skin of the patient, towards ID 100, and ID 100 can be constructed and arranged to harvest the RF energy and/or receive the RF data via antenna 125 (e.g., a power-harvesting antenna). In some embodiments, EPD 200 is constructed and arranged to receive data from one or more implantable devices 100, such as when transceiver 120 is constructed and arranged to transmit RF data to EPD 200.

EPD 200 can include one or more user interfaces, user interface 250 shown. User interface 250 can include one or more user input and/or user output components, for example, one or more: displays, indicators (e.g., LEDs), speakers, buttons, microphones, and/or other user interface components. In some embodiments, EPD 200 includes one or more functional elements, functional element 299 shown. Functional element 299 can include one or more sensors and/or transducers. User interface 250 can display a visual representation of the heart chambers (e.g., a digital model) including one or more electrical conduction patterns (e.g., AF conduction patterns and/or sinus rhythm conduction patterns) that are displayed relative to the representation of the heart anatomy. In some embodiments, user interface 250 can display a representation of one or more portions of ID 100 (e.g., one or more electrodes 111) relative to the representation of the heart. In some embodiments, the conduction patterns displayed include pre-treatment and/or post-treatment (e.g., post pacing) conduction patterns. In some embodiments, the conduction patterns are displayed relative to each electrode 111 that is displayed on the representation of the heart. In some embodiments, user interface 250 can display various simulations of conduction patterns resulting from a proposed therapy to be delivered to treat the arrhythmia (e.g., AF) of the patient.

In some embodiments, functional element 299 of EPD 200 comprises one or more sensors that are used to record a patient parameter, such as a patient EEG. For example, functional elements 299 can comprise one, two, or more sensors (e.g., electrodes) that are positioned on EPD 200 such that the patient can place their thumbs or other fingers to contact the sensors, to provide an ECG recording (e.g., an additional ECG recording collected by system 10). For example, system 10 can perform diagnostic monitoring (e.g., ECG recording) on a predetermined schedule, but also allow for additional diagnostic monitoring (e.g., ECG recording) as determined by the patient (e.g., at any time). In some embodiments, the patient may choose to perform additional monitoring based on a physiologic condition, such as feeling dizzy, feeling faint, having palpitations, having shortness of breath, feeling tired, and the like. In some embodiments, the monitoring of the one or more patient parameters can be initiated by the patient. For example, the one or more patient parameters to be monitored (as initiated by the patient) can comprise at least an ECG, and the system can be configured to adjust the therapy provided (e.g., initiate stimulation energy delivery) based on detection of an arrhythmia via the monitored ECG. In some embodiments, the patient, clinician, and/or other user of system 10 can adjust the monitoring of one or more patient physiologic parameters, such as to establish a time-interval for monitoring of these parameters.

In some embodiments, functional element 299 of EPD 200, and/or another functional element of system 10, comprises one or more sensors that are configured to record EMG, EEG, and/or ECG, and system 10 is configured to analyze the recorded signals in order to perform a diagnosis and/or prognosis ("diagnosis" herein) of sleep apnea of the patient. EPD 200 can be configured to monitor one or more parameters related to the detection of sleep apnea selected from the group consisting of: movement, such as chest movement; snoring; body position; heart rate; O2 saturation; and combinations of these. In some embodiments, system 10 is configured to provide a sleep analysis. Analysis performed by system 10 (e.g., sleep apnea and/or other patient diagnosis such as a diagnosis of atrial fibrillation) can be accessible via an online portal (e.g., a patient portal hosted by server 600), and/or automated reports can be provided to the patient's managing physician.

EPD 200 can include processing unit 210 which can be configured to perform one or more functions of EPD 200. Processing unit 210 can include one or more algorithms, algorithm 215 shown. In some embodiments, processing unit 210 comprises a memory for storing instructions to perform algorithm 215. Processing unit 210 can be constructed and arranged to execute algorithm 215 and to thereby execute one or more functions of EPD 200. In some embodiments, processing unit 210 analyzes data (e.g., via algorithm 215) received from ID 100. For example, EPD 200 can receive data from ID 100, process (e.g., mathematically process) the information received via algorithm 215 (e.g., to determine if pacing should be performed, and to determine the parameters of stimulation energy to be delivered), and send information and/or power to ID 100 based on the processed information.

EPD 200 can include power module 240. Power module 240 can include one or more power-generating, power-harvesting, power-storing, and/or other power-supplying components configured to deliver energy to EPD 200, and/or to deliver power to ID 100 via wireless power transfer. Power module 140 can be configured to provide power to one or more components of EPD 200. In some embodiments, power module 240 comprises one or more batteries, capacitors, and/or other power-storing devices. Power module 240 can be constructed and arranged to "harvest" power from kinetic motion. In some embodiments, power module 140 comprises one or more piezo electric components configured to convert kinetic energy to electrical energy.

CD 300 can include one or more catheters and/or or one or more surgical tools for delivering ID 100 into the patient. Additionally, CD 300 can include one or more devices configured to diagnose and/or treat the patient, such as to perform a diagnosis and/or a treatment during a clinical procedure in which ID 100 is implanted into the patient. For example, CD 300 can comprise a cardiac mapping catheter which can be used to collect data (e.g., data to be processed by console 400) such as to map the cardiac electrical activity of the heart. Additionally or alternatively, CD 300 can comprise an ablation catheter which can be used to ablate tissue (e.g., cardiac tissue). In some embodiments, system 10 can include one or more clinician devices 300 that are constructed and arranged to enable the clinician to perform: a mapping procedure, a tissue treatment procedure (e.g., an ablation procedure or other tissue treatment procedure), and/or an ID 100 implantation procedure (e.g., for continued, post procedural treatment of the patient).

In some embodiments, CD 300 comprises electrode array 310 shown, which can comprise one or more arrays of electrodes that can be inserted into the patient. Electrode array 310 can comprise one or more electrodes 311. CD 300 can include user interface 350 shown. User interface 350 can include one or more user input and/or user output components, for example, one or more: displays, indicators (e.g., LEDs), speakers, buttons, levers, microphones, and/or other user interface devices. In some embodiments, user interface 350 comprises a handle (e.g., a catheter handle) including one or more controls, such as a steering control.

In some embodiments, CD 300 includes transceiver 320. Transceiver 320 can comprise an assembly configured to communicate (e.g., wirelessly communicate) with one or more components of system 10, for example, one or more implanted devices 100, one or more external patient devices 200, console 400, and/or other components of system 10. Transceiver 320 can comprise a receiving and/or transmitting interface, antenna 325. In some embodiments, CD 300 includes one or more functional elements, functional element 399 shown. Functional element 399 can include one or more sensors and/or transducers.

In some embodiments, system 10 is configured to perform an acute assessment and/or treatment of the cardiac substrate, such as when one or more recordings of cardiac signals are recorded by clinician device 300, such as when electrode array 310 is positioned within a chamber of the heart and/or positioned intravascularly within a cardiac vessel, and/or when clinician device 300 is used to treat the cardiac substrate (e.g., when pacing energy is delivered via electrode array 310). Additionally or alternatively, ID 100 can be configured to monitor and/or treat the cardiac substrate temporarily (e.g., acutely) or chronically. For example, ID 100 can be temporarily implanted (e.g., as described herein), such as to temporarily provide substrate monitoring and/or SRT. In some embodiments, ID 100 can be removed and/or otherwise stop monitoring and/or providing therapy (e.g., when ID 100 is configured to remain implanted after a temporary battery has been exhausted). In some embodiments, ID 100 is chronically implanted, such as to provide substrate monitoring and/or SRT chronically.

In some embodiments, clinician device 300 is configured for percutaneous access and/or transvascular access to a location proximate the heart, such as a cardiac vessel, a cardiac chamber, and/or the pericardial space. Clinician device 300 can be configured to access various cardiac locations using various methods, such as percutaneous to transvascular, transvascular to a location outside the heart (e.g., when clinician device 300 is configured to exit the vessel into the pericardial space), and/or transvascular to a location within the heart.

In some embodiments, system 10 includes a data storage and processing device, server 600. Server 600 can comprise an "off-site" server (e.g., outside of the operating room or other clinical site in which ID 100 is implanted), such as a server maintained by the manufacturer of system 10. Alternatively or additionally, server 600 can comprise a cloud-based server. Server 600 can include processing unit 610 shown, which can be configured to perform one or more functions of server 600. Processing unit 610 can include one or more algorithms, algorithm 615. In some embodiments, processing unit 610 includes a memory for storing instructions to perform algorithm 615. Processing unit 610 can be constructed and arranged to execute algorithm 615 and to thereby execute one or more functions of server 600. Server 600 can be configured to receive and store various forms of data, such as: patient, procedural, device, and/or other information, data 620. Data 620 can comprise data collected from multiple patients (e.g., multiple patients treated with system 10), such as data collected during and/or after clinical procedures where ID 100 was implanted into the patient. For example, data can be collected from ID 100, transmitted to EPD 200, and sent to server 600 for analysis. In some embodiments, one or more devices of system 10, such as EPD 200 and server 600, can communicate over a network, network 50, for example, a wide area network such as the Internet. In some embodiments, system 10 includes a virtual private network (VPN) through which various devices of system 10 transfer data.

Algorithm 615 can be configured to analyze data 620. For example, algorithm 615 can be configured to analyze data 620 collected from multiple patients to identify similarities and/or differences in treatment parameters and patient results. In some embodiments, algorithm 615 comprises a machine learning and/or other artificial intelligence algorithm ("AI algorithm" herein) that can be configured to identify patterns in the correlations between treatment parameters and results based on data collected from multiple patients. In some embodiments, algorithm 615 analyzes patterns to determine better treatment parameters for one or more patients to be treated using system 10. For example, algorithm 615 can identify one or more patterns in the data (e.g., one or more patterns associated with efficacy of the treatment being delivered to the patient) by analyzing data 620 collected from many patients (e.g., tens of thousands of patients). Algorithm 615 can be further configured to use these patterns to determine whether a patient (e.g., in the set of patients from which the data was collected and/or in a new patient) is receiving sub-optimal treatment (e.g., the parameters associated with pacing and/or other energy being delivered could be modified to improve efficacy). System 10 (e.g., via algorithm 615) can be configured to alert the clinician of a patient receiving sub-optimal treatment, and to recommend (e.g., via CD 300, such as the clinician's phone or computer) the parameters to be adjusted. In some embodiments, the clinician may schedule an appointment to adjust the parameters (e.g., in person), or the parameters can be adjusted remotely, for example, when CD 300 is configured to adjust the parameters remotely via network 50. Alternatively or additionally, server 600 can adjust the parameter automatically (e.g., via network 50). In some embodiments, one or more parameters are automatically adjustable (e.g., within certain thresholds), while other parameters require clinician approval.

As described herein, system 10 can comprise one or more algorithms, such as algorithms 135, 215, 415 and/or 615 shown in FIG. 1. Various algorithms of system 10 can be referred to singly or collectively herein as algorithm 500. In some embodiments, algorithm 500 comprises a machine learning and/or other artificial intelligence algorithm ("AI algorithm" herein). Any algorithmic process described herein may be performed by any algorithm of system 10 (e.g., algorithms 135, 215, 415, and/or 615). The various processors and/or controllers of system 10 can each comprise memory configured to store instructions for performing the algorithms described herein.

In some embodiments, algorithm 500 can comprise a set of algorithms configured to identify the presence of atrial fibrillation and deliver (e.g., automatically deliver via ID 100) pacing stimuli across a spatially distributed array of electrodes placed on the left atrium (e.g., electrodes 111 of electrode array 110). The pacing stimuli delivered by ID 100 can be imperceptible to the patient. The pacing stimuli can be precisely timed at each electrode 111 to advance and/or block fibrillation wavefronts, for example as described in reference to FIG. 2 and otherwise herein. Delivery of pacing stimuli by ID 100 can be configured to synchronize atrial activation to the pattern of stimulation and can be configured to automatically stop upon restoration of normal rhythm, for example as described herein.

System 10 can be configured to record electrical activity, such as cardiac electrical activity, and algorithm 500 can be configured to analyze the recorded electrical activity. For example, electrical activity can be recorded via one or more electrodes 111 of electrode array 110. The recorded electrical activity can be transmitted, via transceiver 120, to EPD 200. Algorithm 215 of EPD 200 can be configured to analyze the received data, and to determine if stimulation is required to treat the patient. Algorithm 215 can determine a set of stimulation parameters to be delivered by ID 100 based on the received electrical data (e.g., based on a recorded pattern of conduction within the cardiac tissue). For example, algorithm 215 can determine the location and instances in time to deliver stimulation energy (e.g., via electrodes 111). Alternatively or additionally, the recorded electrical data can be transmitted to console 400 and/or server 600, such that algorithms 415 and/or 615 can analyze the data and determine stimulation parameters. The stimulation parameters determined by algorithm 500 can be transmitted back to implantable device 100, via transceiver 220, to ID 100. In some embodiments, the stimulation parameters prescribe stimulation pulses to be delivered as a sequence of pulses to be delivered simultaneously and/or asynchronously, and/or regularly and/or irregularly. The stimulation pulses can be delivered from one or more electrodes 111. In some embodiments, algorithm 135 is configured to process stimulation parameters received from EPD 200 and stimulate via electrodes 111 based on the processed parameters. Alternatively or additionally, ID 100 does not comprise an algorithm, and is configured to stimulate based on power and/or data received from EPD 200 (e.g., stimulation power is received by transceiver 120 and provided to an electrode 111 based on data received with the transmitted power).

In some embodiments, system 10 is configured to stimulate cardiac tissue by providing electrical stimulation such that any pain and/or discomfort caused by the delivery of the electrical stimulation is below a threshold, such as below a perception threshold (e.g., provide "shock-free" stimulation where patient doesn't feel any pain or discomfort caused by the delivery of the electrical stimulation).

As described herein, system 10 can be configured to perform multisite pacing, such as to terminate AF and/or SVT of the patient. AF can be caused by a stretch-induced infiltration of fibrosis that is progressively and broadly distributed across the left atrium. Global, simultaneous mapping of AF has revealed patient-specific confined zones of conduction that are distributed primarily across three anatomical regions of the left atrium: (1) posterior wall; (2) anterior-roof; and (3) anterior-septum. In the early phase of AF, categorized as "paroxysmal", the progression of fibrosis is more confined to the muscular sleeves surrounding the pulmonary veins and the posterior wall of the left atrium. As the disease of AF progresses into the "persistent" stage, fibrosis spreads beyond the posterior wall, predominantly emerging at patient-specific locations across the roof and septum, anteriorly.

The feasibility of low-voltage shocks and multisite pacing for terminating AF can be limited by: (1) the number, size, and/or distribution of electrodes placed about the left atrium; and (2) the pattern of stimulation energy delivered. The progressive nature of the disease requires matching the spatiotemporal characteristics of pacing with the patient-specific distribution of fibrosis.

In the early, paroxysmal phase of AF, pacing can be delivered from multiple (e.g., 3 or 4) electrodes distributed within the Vein of Marshall and the adjacent coronary sinus. These locations are close to the lateral border of the posterior wall and the left pulmonary veins, where stimulation is required for effective interruption of fibrillatory conduction in the region of the left atrium that is relevant for paroxysmal AF.

In the later persistent and long-standing phases of AF, pacing can be delivered from more electrodes (e.g., 5 or 6 electrodes) that are distributed epicardially on the posterior wall, the anterior roof, and/or superior septum. These locations are close to the critical, "confined zones" of conduction that maintain AF. Stimulation is required to be delivered near these zones for effective interruption of fibrillatory conduction in the regions of the left atrium that are relevant for persistent AF.

In some embodiments, one or more sensors (e.g., functional element 199 comprising one or more sensors and/or one or more electrodes 111 configured as a sensor) of ID 100 (e.g., an ID 100 comprising one or more implantable devices) are positioned at one or more locations proximate heart tissue and are configured to produce signals from which a calculation of pressure within a chamber (e.g., pressure of the blood within the left atrium) can be determined (e.g., by one or more of algorithms 500), such as is described in reference to FIG. 1 herein. In some embodiments, the signals are recorded from (e.g., ID 100 and the associated sensors are implanted at) a location outside of the chamber of the heart for which the chamber pressure is determined (e.g., outside of the left atrium when left atrial pressure is determined). For example, one, two or more electrodes 111 of ID 100 (e.g., an ID 100 comprising one, two, or more implantable devices) can be configured to record signals to determine a chamber pressure, such as when an impedance measurement is performed to identify impedance characteristics of tissue surrounding a heart chamber (e.g., the left atrium) that can be correlated (e.g., by an algorithm 500) to the chamber pressure (e.g., left atrial pressure). Alternatively or additionally, functional element 199 of ID 100 (e.g., an ID 100 comprising one, two, or more implantable devices) can comprise one, two, or more sensors configured to produce a signal (e.g., record a physiologic parameter) that can be used to determine the pressure of a heart chamber. In some embodiments, at least one, two, or more of these sensors are positioned within the chamber for which the chamber pressure is determined. In some embodiments, at least one, two, or more of these sensors are positioned on tissue that is proximate, but outside the chamber for which the chamber pressure is determined (e.g., on the epicardial wall), such as when no sensors are present within that chamber. Applicable sensors for producing a signal used by system 10 (e.g., an algorithm 500) to determine a chamber pressure include but are not limited to: a pressure sensor; a strain gauge (e.g., to measure strain in tissue that can be correlated to the chamber pressure proximate the tissue on which the sensor is positioned); an accelerometer (e.g., to measure tissue motion that can be correlated to chamber pressure proximate the tissue on which the sensor is positioned); an ultrasound sensor and/or other acoustic sensor, such as a doppler ultrasound sensor (e.g., configured to measure one or more blood flow parameters which can be correlated to the chamber pressure); an optical sensor (e.g., configured to measure one or more tissue and/or blood properties which can be correlated to the chamber pressure); and combinations of these.

In some embodiments, system 10 is configured to deliver pacing stimulation during sinus rhythm, such that the stimulation is configured to synchronize activation of the left ventricle. This stimulation can improve the timing and volume filling of the left ventricle and can increase cardiac output. Since the 1990's, it has been shown that a natural variability in heart-rate reduces vulnerability of the cardiac substrate to initiation and/or re-initiation of arrythmia. Non-linear pacing can be defined as delivery of pacing energy that is irregular, aperiodic, and/or otherwise varying (e.g., in level, frequency, modulation, and the like). System 10 can be configured to deliver nonlinear pacing. Alternatively or additionally, system 10 can be configured to deliver spa-tiotemporal resynchronization therapy, SRT. SRT shall include the ability to control a fibrillating substrate by deterministically pacing into the narrowed excitable gap present during AF, such as from a well distributed set of electrodes. Once each electrode has gained control of the adjacent substrate, system 10 selectively advances the pac-ing to achieve alignment across electrodes, prolonged, and inhibited to allow normal sinus rhythm to return. Accord-ingly, after delivery of SRT via system 10 has terminated AF, another algorithm (e.g., algorithm 135) can be applied to device 100 in which the baseline sinus rhythm is nonlinearly (e.g., deterministically) varied with "irregularly-early" pac-ing pulses that impose said deterministic variation in heart rate. In another embodiment, this can be achieved by first deriving the mean and standard deviation (or median and IQR) of heart rate for a predetermined period. Based on these parameters, stimuli can then be delivered according to a "fractal" or other appropriate nonlinear function that paces the heart at a time that is "earlier" than the mean cycle-length (e.g., inverse of heart-rate) to deterministically impose a variation in said beat, as compared to the previous beat. Similarly, subsequent beats can be at differing dura-tions of "earliness" to impose a desired variability in the heart rate over time. Such a configuration can also include occasional inhibition of pacing to achieve the "intrinsically-longest" cycle-length, as a part of the overall range of variation that occurs over time. Such a configuration can also include periodic cessation of pacing to re-assess the mean and standard deviation (or median and IQR) of heart rate. In such a configuration, the algorithm (e.g., algorithm 135) can follow the natural variation in heart rate and enhance the natural variation (or lack thereof) with "vari-ably-early stimulation". The overall goal of such a pacing algorithm (e.g., algorithm 135) is to achieve a level of variation that optimizes the probability of reducing vulner-ability to initiation and/or re-initiation of arrhythmia. In some embodiments, system 10 can deliver multiple different forms of energy delivery, such as to treat different medical conditions of the patient (e.g., at least AF), for example as described herebelow in reference to FIG. 10.

During AF ablation procedures, AF is terminated into sinus rhythm during the delivery of ablation in approxi-mately 35% of procedures. In approximately 10% of these 35% of procedures, the SA-node fails to automatically re-initiate a baseline ("normal") sinus rhythm. In such cases, the SA-node appears to have been electrically remodeled into a quiescent state that is presumably due to the rapid impingement of activation upon it during the ongoing AF. It has also been observed that such instances of cessation are temporary, with SA-node activation gradually "waking-up" and resuming the maintenance of baseline sinus rhythm. Such wake-up periods generally range from a few minutes to about 30 minutes. At this point in the procedure, the laboratory stimulator is applied to address the bradycardia and maintain a normal baseline heart rate, while the SA-node is recovering its ability to maintain sinus rhythm. This is performed by the support staff (e.g., laboratory) at the request of the clinician (e.g., physician), by pacing through existing catheter-electrodes that are already placed in the heart. Accordingly, after nonlinear pacing (e.g., spatiotem-poral resynchronization therapy, SRT, as defined herein) via system 10 has terminated AF, another algorithm (e.g., algo-rithm 135) can be applied by ID 100 in which the baseline sinus rhythm is temporarily maintained at a "typically normal" rate. In another embodiment, this can be achieved by first deriving the mean heart rate over a short period (e.g., several beats). In accordance with a maximum threshold of cycle-length, stimulation can be delivered (including "immediately") in the "AAI" pacing mode (Atrial sensing/ Atrial pacing/Inhibited). Such a configuration can comprise periodically inhibiting pacing, while pacing is inhibited re-assessing the intrinsic heart rate and determining if the SA-node has recovered; if recovery is determined, pacing can remain inhibited. Additionally, such a configuration can also include variation in the pacing rate, as disclosed here-inabove, with the goal of reducing the vulnerability of the cardiac substrate to initiation and/or re-initiation arrhythmia. Another embodiment can consider application of the VVI pacing mode (Ventricular sensing/Ventricular pacing/Inhib-ited). This mode can be considered less desirable than atrial pacing for aiding in the recovery of the SA-node, as it depends on adequate retrograde conduction through the AV-node. Conversely, atrial pacing is directly "in-line" with the SA-node, and such conduction characteristics may play a positive role in recovery of the SA-node. Ventricular pacing, on the other hand, directly addresses the undesired slow heart rate (e.g., bradycardia) without any consideration on the "health" of AV-node conduction. Regardless, ven-tricular pacing is inherently less desirable than atrial pacing, as an additional device (e.g., ID 100) must be applied upon the ventricle to fulfill this embodiment. In the rare instance where the SA-node remains quiescent for a prolonged period, then the clinician (e.g., physician) can be notified through the device upload. In such rare cases, the patient enters a separate category that requires another type of therapy. In that case, there would likely be implantation of a pacemaker to address bradycardia caused by a "sick sinus node". In the less-rare instance of AV-node conduction disease, the patient may have been identified as having various levels of AV-block at a much earlier time in their treatment history. In that case, implantation of a pacemaker may likely have already been performed to address brady-cardia caused by abnormal AV-node conduction. In either case, as described hereinabove, implantation of a pacemaker can be symbiotic with implantation with ID 100.

In some embodiments, system 10 is configured to provide treatment for left atrial pre-conditioning (e.g., pre-condition-ing for a patient with atrial fibrillation prior to an ablation procedure). Pre-ablation pacing therapy, implanting the device 3 months prior to ablation to maximize the likelihood of maintaining sinus rhythm after the ablation procedure. Delivered over some months, pre-ablation pacing can result in enough reverse-remodeling to regain some level of orga-nization that reveals demarcated, putative ablation targets in a future ablation procedure. In some embodiments, system 10 is configured to provide treatment for left atrial re-conditioning, for example by providing a "blanking period" post ablation. Early recurrence of atrial fibrillation (AF) or atrial tachycardia (AT) after catheter ablation (CA) in AF patients is known to be a transient phenomenon. An expert consensus group recommends to measure the success of an ablation therapy from 3 months after the procedure onward. This period is termed the "blinding or blanking period" and is now widely adopted in both clinical routine and clinical trials. The 3-month period is often thought of as a time for the lesions to maturate and heel.

The underlying pathophysiological processes responsible for early recurrence and the delayed cure are unknown. Early recurrence is considered the consequence of ablation-induced proarrhythmic factors that are limited to the time frame of the blanking period. Whereas a delayed cure may also be the cause of an antiarrhythmic effect that develops in the course of the blanking period and that is not necessarily related to electrical isolation of the PV. A potential confounding influence is played by the use of AADs during the blinding period, as they may paradoxically act as a possible proarrhythmic factor. AADs are usually discontinued after the 3-month period, and this may unmask the antiarrhythmic effect of the ablation procedure. The theoretical basis of the blanking period is based on such observations. However, the clinical implications of early recurrence may be avoided. The incidence of early AF recurrence during the 3-month blinding period following PVI ranges from 9 to 65%. It has been shown that 54% of patients have early recurrence within week 1 to 2 following ablation therapy, after which the percentage drops to 38% in weeks 2 to 4 and to 24% in weeks 4 to 6. The first episode of early recurrence occurs within month 1 of the blinding period in 81% to 91% of patients with early recurrence. This emphasizes the dynamic nature of the blinding period.

AF is a complex arrhythmia with multiple possible mechanisms underlying initiation and maintenance. Ablation is successful in 60% of paroxysmal AF patients. AF can recur during the 3-month blanking period after ablation. No therapy or interaction takes place during this 3-month blanking period.

Recent retrospective studies indicate that right atrial pacing decreases the incidence of AF They demonstrated significant benefit for atrial pacing with improved survival and a decreased incidence of thromboembolic events, AF, and congestive heart failure, especially after longer follow-up. The hypothesis: if during the so-called blanking period, where no therapy or patient management is occurring, change this 3-month period into a left Atrial "Re-Conditioning" period. System 10 can be configured to perform continuous (7/24) sinus rhythm pacing. This not only keeps the post ablation patient in sinus rhythm but reverse remodels the left atrium (AF remodels the left atrium to AF), reconditioning reverses this AF remodeling back to normal. Post the 3-month LA re-conditioning, the ID 100 can perform normal monitoring and deliver therapy only when the patient has an AF episode.

In some embodiments, system 10 is configured to deliver multisite pacing for termination of atrial fibrillation, such as is described herein. AF is caused by a stretch-induced infiltration of fibrosis that is progressively and broadly distributed across the left atrium. Global, simultaneous mapping of AF has revealed patient-specific confined zones of conduction that are distributed primarily across three anatomical regions of the left atrium: (1) posterior wall; (2) anterior-roof; and (2) anterior-septum. In the early phase of AF, categorized as "paroxysmal", the progression of fibrosis is more confined to the muscular sleeves surrounding the pulmonary veins and the posterior wall of the left atrium. As the disease of AF progresses into the "persistent" stage, fibrosis spreads from the posterior wall predominantly across the roof and septum, anteriorly, toward the mitral valve annulus. The feasibility of low-voltage shocks and multisite pacing for terminating AF has been demonstrated and is primarily limited by: (1) the number and distribution of electrodes placed about the left atrium; and (2) the algorithm (e.g., algorithm 135) governing the pattern of stimulation. The progressive nature of the disease can require matching the spatiotemporal characteristics of pacing with the patient-specific distribution of fibrosis. For example, in the early, paroxysmal phase of AF, pacing can be delivered from 3 or 4 electrodes, such as 3 or 4 electrodes distributed within the Vein of Marshall and the adjacent coronary sinus. These locations are close to the lateral border of the posterior wall and the left pulmonary veins, and from these locations stimulation can be delivered for effective interruption of fibrillatory conduction in the region of the left atrium that is relevant for paroxysmal AF. Additionally or alternatively, in the later, persistent and long-standing phases of AF, pacing can be delivered from 5 or 6 electrodes distributed epicardially on the posterior wall and/or the anterior roof. These locations are close to the critically, "confined zones" of conduction that maintain AF. Stimulation can be delivered near these zones for effective interruption of fibrillatory conduction in the regions of the left atrium that are relevant for persistent AF.

In some embodiments, system 10 is configured to provide left atrial pacing therapy to improve hemodynamic function. Extensive ablation of the left atrium for treatment of AF can lead to a decrease in overall hemodynamic function. This occurs when significant delay of conduction to the left-atrial appendage is imposed by ablation lesions that are delivered between the insertion of Bachmann's Bundle, in the high septum and roof, and the appendage. Normally, the appendage is a significant contributor to the mass transport of blood from the left atrium to the left ventricle. If activation of the appendage is delayed by intervening ablation-lesions, then the timing of active pumping by the appendage is also delayed. It is possible for this delay to be long enough to be working against the closure of the mitral valve during the beginning of left ventricular contraction. In this case, filling of the left ventricle is incomplete and overall hemodynamic performance is compromised. In the long term, this effect, in combination with other factors, can lead to the gradual decline of heart failure.

System 10 can be configured to enable the placement of one or more pacing electrodes in the distal-reach of the Vein of Marshall. This region of the vein is in relatively close apposition to the posteromedial aspect of the left atrial appendage. Specifically, this is the same general location where the left-lateral branch of Bachmann's Bundle terminates and which enables timely activation of the left atrial appendage. Accordingly, after pace termination of AF by system 10, the most distal electrode in the Vein of Marshall can then be used to ensure timely activation of the left atrial appendage. This concept is analogous to ventricular resynchronization therapy, whereby the right and left ventricles are paced in specific locations and with relative timing of stimulation that are intended to synchronize activation of both ventricles for the purpose of improving and optimizing overall hemodynamic performance. In the case of delayed conduction in the left atrial appendage, the effectiveness of ventricular resynchronization therapy can be compromised or severely limited. Accordingly, left atrial appendage resynchronization pacing can improve overall hemodynamic performance, either with or without ventricular resynchronization therapy. One embodiment can include sensing the timing of activation from one or more implanted electrodes 111 and/or one or more surface ECG leads. These signals would be used to algorithmically (e.g., via algorithm 135) sense the relative timing between the beginning of left atrial activation and the time of activation of the left atrial appendage. The algorithm (e.g., algorithm 135) can command an electrode 111 to pace at an optimal time in the attempt to promote optimal left-ventricular filling.

In some embodiments, system 10 is configured to deliver median and/or ulnar nerve stimulation for the purpose of shifting the operating-point of afferent autonomic tone toward inhibition of AF across the left-atrial substrate. Additionally or alternatively, system 10 can be configured to deliver stimulation to nerve bundles in the feet or in the ear. The autonomic nervous system plays a significant role in modulating the overall state of syncytial-conduction throughout the left-atrial myocardial substrate. It is challenging to access both the efferent nerve fibers, from the gangliated plexi, as well as the distribution of afferent fibers that insert throughout the left-atrial chamber. Consequently, the objective of either ablating (e.g., destroying) these nerves or modulating (e.g., stimulating) these nerves has not been adequately effective. It has been shown acupuncture therapy that targets the Median Nerve promotes cessation of arrhythmias, notably AF. Recent clinical studies have validated this observation from the practice of acupuncture. System 10 can be extended and/or coordinated, algorithmically (via algorithm 135), together with sensing of intracardiac and/or surface ECG signals to stimulate pacing electrodes that are located on the arm, for example, within a wrist-band, that is positioned to stimulate the Median and/or Ulnar nerves and thereby mediate modulation of autonomic vagal tone in the direction of at least partial inhibition of AF.

In some embodiments, system 10 includes one or more computer applications (e.g., software applications performed by a processor of system 10, where the instructions for performing the applications are stored in memory of system 10), such as cardiac simulator 4101, comprising a cardiac tissue simulator application. Cardiac simulator 4101 can include an interactive, physiologically realistic, and accurate computer simulation that allows multiple scenarios to be tested in a "live" environment (e.g., during a clinical procedure). In some embodiments, cardiac simulator 4101 is performed by processing unit 410 of console 400. Cardiac simulator 4101 can be used for the rapid development and testing of treatment strategies for atrial fibrillation (AF). Cardiac simulator 4101 can include a model of cardiac tissue that allows the user to define the regions and zones of anisotropic conduction to test the effectiveness of a variety of AF treatment strategies.

The model was developed using standard electrophysiologic (EP) parameters established in the literature. An advanced implementation of the Fitzhugh-Nagumo model reproduces the action potential morphology of the human atrium enabling live simulations. To reproduce the complex conduction patterns (CCP) of AF identified in the EP lab, a bi-layer model was implemented to represent epi- and endocardial dissociation. The model allows the user to define regions of fibrosis, zones of slow conduction, and action potential duration (APD). The user can graphically draw these regions and zones, including gradients assigned by maximum and minimum values of conduction velocity (CV) and APD. The EP lab experience and workflow is reproduced, with CCP visualized on a 3D anatomy and signal traces of calculated potentials displayed. To test the CCPs and performance of the model, isolated, geometrically, symmetric zones of conduction were defined on a 3D left atrial model.

Figure 1A:
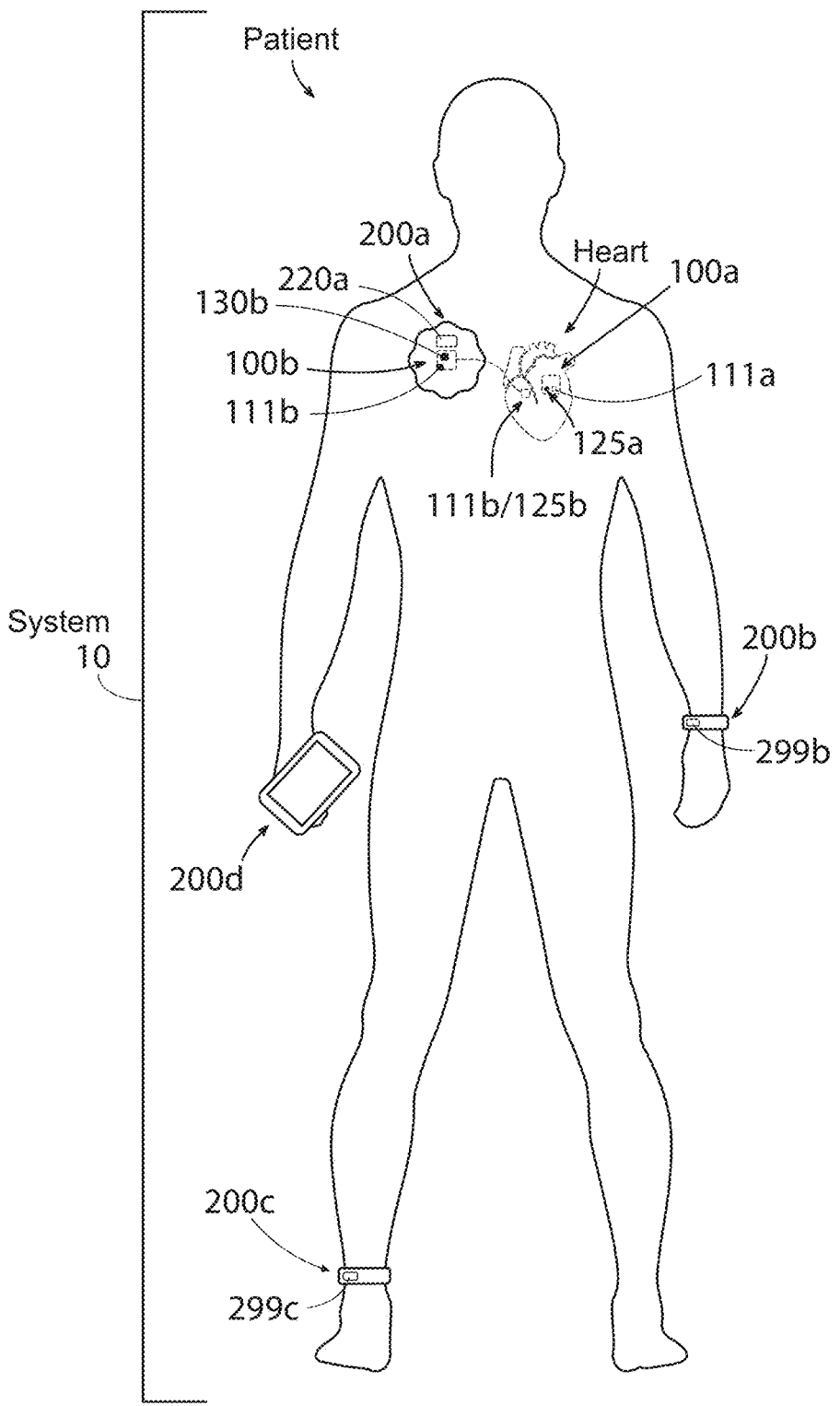
FIG. 1A illustrates a partial anatomic, partial schematic view of a system of devices, consistent with the present inventive concepts.

Referring additionally to FIG. 1A, a partial anatomic, partial schematic view of a system of devices is illustrated, consistent with the present inventive concepts. In some embodiments, system 10 includes one, two, three, or more implantable devices, such as the two implantable devices 100a and 100b shown. For example, system 10 can include ID 100a, including an implantable device positioned proximate the left atrium of the heart, for example on the epicardial surface of the left atrium or within a cardiac vessel proximate the left atrium. System 10 can also include ID 100b, including an implantable device with at least a portion positioned away from the heart, for example comprising an implantable pulse generator (IPG) that is implanted in a subcutaneous pocket. In some embodiments, ID 100b includes a lead operably connecting controller 130b to electrode 111b and/or antenna 125b implanted proximate the heart, for example implanted within the right atrium on the septal wall. Antenna 125b can be positioned proximate antenna 125a of ID 100a to minimize the transmission distance between ID 100a and ID 100b (e.g., the distance over which power is transmitted from ID 100b to ID 100a).

In addition to one, two, three, or more internal devices, system 10 can include one, two, three, or more external patient devices, such as the four external devices 200a-d shown. For example, system 10 can include EPD 200a, including a patient worn device configured to be positioned (e.g., temporarily positioned by the patient) proximate an implantable device, such as proximate ID 100b as shown, and/or proximate ID 100a (e.g., when system 10 does not include a subcutaneous implant, such as ID 100b). EPD 200a can be positioned to minimize the transmission distance between transceiver 220a and the intended ID (e.g., ID 100a and/or ID 100b). System 10 can also include one or more additional patient worn and/or handheld devices, such as EPD 200b comprising a wrist worn device (e.g., a smart watch), EPD 200c comprising an ankle worn device (e.g., a "smart" sock, and/or a fitness tracker), and/or EPD 200d comprising a computing device (e.g., a smartphone). In some embodiments, EPD 200 *a,b,c,d* are configured to communicate with each other, for example when one EPD 200 (e.g., EPD 200d) is configured to gather data collected by each EPD 200 and/or ID 100 and to analyze the aggregated data (e.g., via algorithm 215). In some embodiments, and EPD 200 is configured to collect data and send the aggregated data to server 600 (e.g., when EPD 200d comprising a smart phone is configured to collect all patient data recorded by system 10 and transmit the data via the internet to server 600 for analysis). In some embodiments, one or more of EPD 200 can include one or more functional elements, such as functional elements 299b and 299c shown.

In some embodiments, one or more of the devices of system 10 comprises two or more batteries, such as when a device includes a primary power supply (e.g., one or more batteries and/or one or more capacitors) and a backup power supply (e.g., one or more batteries and/or one or more capacitors). For example, power module 140 of ID 100 can comprise a first battery and/or capacitor, battery 1401, and a second battery and/or capacitor, battery 1402 (as shown in FIG. 1). Battery 1401 can be configured as a main power source for ID 100, and battery 1402 can be configured as a backup power source, for example to be used if battery 1401 is depleted. In some embodiments, battery 1401 and/or 1402 are rechargeable. In some embodiments, battery 1402 is configured to maintain operation of ID 100 if the patient is unable to charge battery 1401 for a period of time (e.g., the patient is away from the charger when battery 1401 runs low on power). Batteries 1401 and 1402 can comprise batteries with similar or dissimilar battery chemistry, for example lithium-ion batteries and/or lithium thionyl chloride batteries. In some embodiments, ID 100 comprises a single battery 1401, and system 10 (e.g., algorithm 135 of system 10) is configured to virtually partition the single battery into two virtual batteries, such that ID 100 functions as if battery 1401 comprised a main battery and a backup battery. In some embodiments, batteries 1401, 1402 comprise different size batteries (e.g., batteries with different amp-hour capacity). In some embodiments, ID 100 can operate in two or more power modes, for example a first, "normal-power" mode, and a second, "low-power" mode. In some embodiments, when the main power supply of ID 100, battery 1401, is depleted, ID 100 transitions into the low power mode and operates using energy from battery 1402, for example until battery 1401 can be recharged. In some embodiments, if battery 1402 is used for a period of time, for example at least 1 hour, at least 6 hours, at least 12 hours, at least 1 day, and/or at least 1 week, ID 100 and/or battery 1402 (e.g., when battery 1402 is replaceable), are replaced (e.g., in a follow-up procedure) to ensure ID 100 maintains adequate backup power supply (e.g., backup battery supply and/or backup capacitor supply) at all times. In some embodiments, power module 140 is configured to periodically test battery 1401 and/or 1402, for example to confirm battery 1402 is charged and available to provide backup power. In some embodiments, system 10 can be configured to enter an alert mode (e.g., provide an alert to the user as described herein) if a power supply level (e.g., battery level and/or capacitor charge level) is below a threshold, and/or if ID 100 transitions to a low power mode.

In some embodiments, ID 100 is configured to deliver both life-saving therapy (or life-sustaining therapy, either or both "life-saving therapy" herein) as well as quality-of-life therapy. In these embodiments, ID 100 can be configured to provide multiple forms of therapy, such as a first form of therapy (e.g., a life-saving therapy) and/or a second form of therapy (e.g., a quality-of-life therapy), and ID 100 can be configured to deliver (e.g., only deliver) a particular type of therapy based on the amount of energy stored in ID 100 (e.g., the energy stored in battery 1401 and/or battery 1402). In these embodiments, ID 100 can be configured to provide only life-saving therapy when the energy stored in battery 1401 and/or battery 1402 is below a threshold (e.g., below a pre-determined amount of energy). In some embodiments, ID 100 can be configured to provide life-saving therapy comprising cardiac pacing (e.g., pacing of the ventricle, such as when complete AV node block is present), and ID 100 can be further configured to provide quality-of-life therapy comprising providing stimulation energy to treat AF. In some embodiments, ID 100 is configured to deliver atrial pacing that is configured to: address bradycardia due to sinus node dysfunction; maintain normal heart rate variability; and/or to reduce the vulnerability to re-initiation of AF. ID 100 can also be configured to perform non-therapy-related tasks, as described herein, such as communicate with external devices (e.g., EPD 200), perform self-diagnostics, monitor patient parameters, and/or other non-life-saving tasks. In some embodiments, where ID 100 is configured to operate (e.g., sequentially operate) in a regular-power mode and a low-power mode, when ID 100 enters a low-power mode, only life-saving therapy is provided to the patient, such as to allow ID 100 to continue to operate (e.g., as long as possible) until a normal or otherwise improved power mode can be re-initiated (e.g., when battery 1401 is charged). Alternatively or additionally, ID 100 can comprise a first battery and/or capacitor, battery 1401, that is used to power a first set of operations, and a second battery and/or capacitor, battery 1402, that is used to power a second set of operations. For example, battery 1401 can be used to power life-saving operations, such as cardiac pacing (e.g., when ID 100 is configured as a pacemaker), and battery 1402 can be used to power quality-of-life therapy operations, for example operations of ID 100 which monitor for and treat AF.

In some embodiments, one or more algorithms 500 are configured to assess the cardiac electrical activity of one or more regions of a patient's heart, such as by analyzing one or more signals recorded by system 10, as described herein. In some embodiments, a region comprises a single chamber of the heart, for example when algorithm 500 is configured to assess the electrical activity of the left atrium or the left ventricle (e.g., to assess the recorded electrical activity from a chamber collectively). In some embodiments, a region comprises a portion of a chamber, such as when algorithm 500 is configured to assess a portion of the tissue of an atrium or ventricle (e.g., to assess the recorded electrical activity of only a portion of the chamber). In some embodiments, algorithm 500 is configured to automatically and/or semi-automatically (e.g., semi-automatically with input from the user of system 10) divide a chamber into two or more regions, such as by assigning a first set of electrodes 111 to a first region, and a second set of electrodes 111 to a second region. In some embodiments, algorithm 500 is configured to define one or more sets of electrodes 111 by assessing the signals recorded from the electrodes and grouping the electrodes based on the recorded signals (e.g., grouping the electrodes 111 based on common frequencies in the recorded signals).

In some embodiments, ID 100 is configured to deliver stimulation energy configured to defibrillate cardiac tissue. In some embodiments, one or more defibrillation pulses are delivered via two or more groups of electrodes 111 of ID 100. In some embodiments, one or more defibrillation pulses are delivered prior to pacing, such as SRT pacing described herein. In some embodiments, defibrillation pulses delivered via electrodes 111 of ID 100 comprise a lower energy than similar pulses configured to be delivered via one or more external electrodes. Additionally or alternatively, defibrillation pulses delivered via electrodes 111 of ID 100 can comprise pulses that are imperceptible to the patient.

Figure 2:
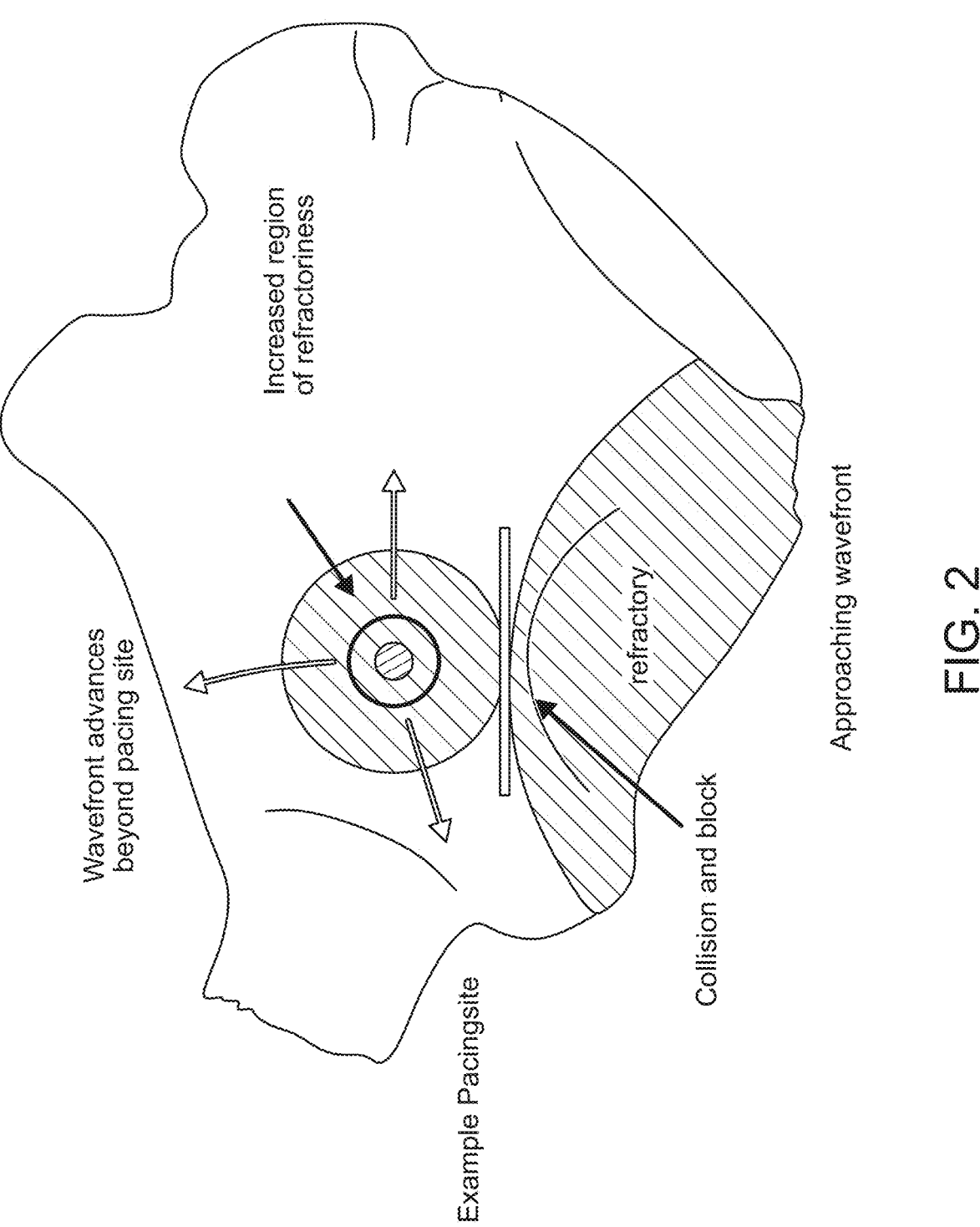
FIG. 2 illustrates an anatomic view of an atria showing electrical activity, consistent with the present inventive concepts.

Referring now to FIG. 2, an anatomic view of an atria showing electrical activity is illustrated, consistent with the present inventive concepts. In some embodiments, algorithm 500 of system 10 described herein is configured to determine a pacing strategy to terminate AF. In some embodiments, the pacing strategy includes providing stimulation energy intended to advance and/or block one or more wavefronts (e.g., cardiac activation wavefronts) to increase the region of refractoriness. In some embodiments, pacing is initiated ahead of an approaching wavefront which can both advance the wavefront beyond the pacing site and block the wavefront behind the pacing site, as shown.

Figure 2A:
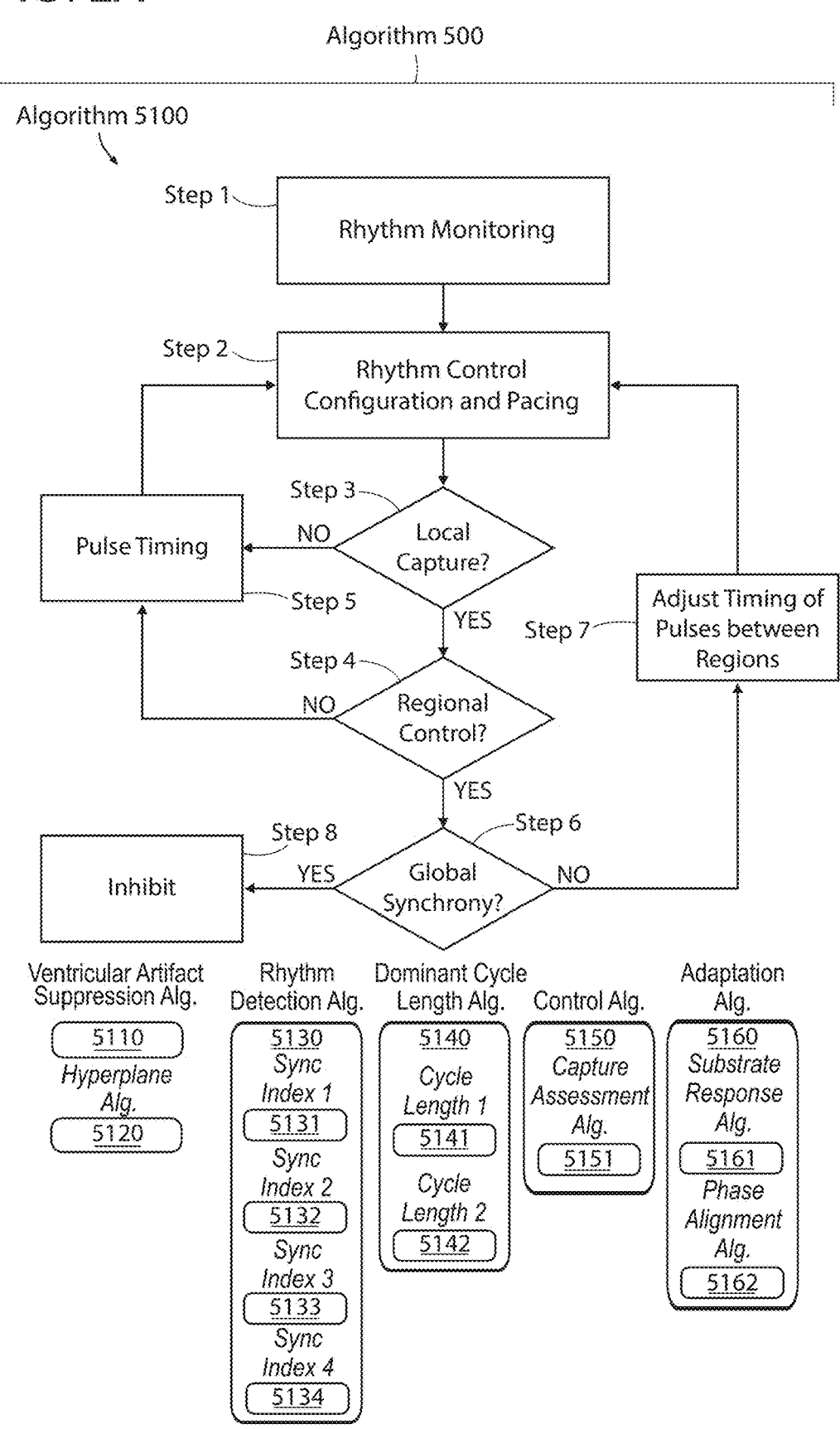
FIG. 2A illustrates a method of monitoring and treating atrial fibrillation, consistent with the present inventive concepts.

Referring now to FIG. 2A, a flow chart of an algorithm for monitoring and treating atrial fibrillation is illustrated, consistent with the present inventive concepts. As described herein, system 10 can comprise various algorithms, referred to singly and/or collectively as algorithm 500. In some embodiments, algorithm 500 comprises one or more routines for the operation and performance of various functions of ID 100 and/or other devices of system 10. Algorithm 500 can include one or more "operating algorithms" that are configured to execute one or more routines (e.g., one or more other algorithms) of various components of system 10. Additionally or alternatively, algorithm 500 can include one or more "functional algorithms", where each functional algorithm can comprise one or more routines for performing various processes or other functions to be executed by system 10 (e.g., processes or functions of ID 100). For example, algorithm 500 can include algorithm 5100 shown, comprising an operating algorithm which executes various functional algorithms as shown and described herein. Algorithm 5100 of FIG. 2A can be executed by one or more components of system 10 described herein (e.g., algorithm 5100 can be executed by a processing unit of a device described herein, which thereby executes one or more functions as determined by the algorithm). FIG. 2A shows the architecture of algorithm 5100, where during each step of the algorithm, one or more functional algorithms are executed. Algorithm 5100 can cause the various hardware components of system 10 (e.g., the hardware of ID 100) to perform one or more actions, such as to record electrical data and/or provide stimulation energy. Additionally or alternatively, algorithm 5100 can perform various analysis of data, such as analysis of electrical activity data recorded by ID 100. Algorithm 5100 can comprise one or more functional algorithms, for example, "Ventricular Artifact Suppression" algorithm 5110, "Hyperplane" algorithm 5120, "Rhythm Detection" algorithm 5130, "Dominant Cycle Length" algorithm 5140, "Control" algorithm 5150, and/or "Adaptation" algorithm 5160, each described herein. The various functional algorithms of algorithm 5100 can be executed in conjunction with each other to cause data to be recorded, and to analyze that data to evaluate the intrinsic rhythm, to measure the cycle length, to configure pacing parameters (e.g., configuring pacing energy delivery parameters and/or other pacing parameters), to verify the effect of pacing (e.g., the effect of delivery of pacing energy performed by ID 100), to adapt to the response of the substrate (e.g., the response to pacing performed by ID 100), and/or to initiate or inhibit pacing.

In some embodiments, algorithm 5100 includes "Ventricular Artifact Suppression" algorithm 5110. Algorithm 5110 can process recorded signals (e.g., unipolar signals) to remove the ventricular artifact. Processed signals can then be analyzed by other algorithms of algorithm 5100, for example to determine cycle length measurements and/or perform synchronization assessments as described herein. Ventricular artifact suppression algorithm 5110 can be configured as described in reference to FIG. 11 and otherwise herein.

In some embodiments, algorithm 5100 includes "Hyperplane" algorithm 5120. In some embodiments, hyperplane algorithm 5120 provides foundational processing of recorded signals to subsequently perform various other algorithms of algorithm 5100, such as various algorithms of rhythm detection algorithm 5130, described herein, and/or dominant cycle length algorithm 5140, also described herein. Hyperplane algorithm 5120 can be configured as described in reference to FIGS. 12A-F and otherwise herein.

In some embodiments, algorithm 5100 includes "Rhythm Detection" algorithm 5130. Rhythm detection algorithm 5130 can include various algorithms that provide various methods of determining the degree of irregularity of cardiac activation patterns. For example, rhythm detection algorithm 5130 can include various "Sync Index" algorithms, such as Sync Index algorithm 5131, Sync Index algorithm 5132, Sync Index algorithm 5133, and/or Sync Index algorithm 5134, each described herein. Sync index algorithm 5131 is described in reference to FIGS. 8A-8E and otherwise herein. Sync index algorithm 5133 is described in reference to FIGS. 13A-C and otherwise herein. Sync index algorithm 5134 is described in reference to FIGS. 14A-F and otherwise herein.

Sync index algorithm 5132 can be configured to process recorded signals that have been projected onto a hyperplane, for example by hyperplane algorithm 5120 described herein. After the signals have been projected, sync index algorithm 5132 can define an axis for the projected set of signals with coordinates [u,v]. The axis should bisect the projected attractor (PA) with an equal distribution of data about the axis. Algorithm 5132 can create the axis by determining the optimal circle that encloses the PA, for example by using the algorithm published by John D'Errico (2023). Algorithm 5132 can determine the center of the PA using a suite of minimal bounding objects, such as a suite from MATLAB Central File Exchange. Algorithm 5132 can translate the origin of all the coordinates to the center of the PA. Algorithm 5132 can rotate the PA in such a way that the sections corresponding to baseline values are aligned on the positive u axis (horizontal axis). This can be performed by calculating the average value of u and v, which is called p=[u0,v0]. Algorithm 5132 can then compute the angle φ of p with respect to the u axis. Algorithm 5132 can then perform a two-dimensional rotation of the PA by −φ. This results in the signal baseline being aligned on the positive u axis. The translation and rotation of the PA improves the accuracy of rhythm detection because the critical features of the signals are repositioned and constrained about the negative u axis and the positive and negative v (vertical) axis. The position of the PA can be incrementally rotated by an amount θ, resulting in a new set of points that are repositioned around the positive u axis, or equivalently, in the region around v=0. Algorithm 5132 can then determine the position at which the [u, v] trajectory crosses the positive u axis, and record the u and v values each time the signal trajectory crosses the u or v axis. These recorded values can be numbered r1=[u1,v1], r2=[u2,v2], . . . $r_n$=[$u_n$,$v_n$]. Once all the crossing pairs are collected for a particular angle θ, algorithm 5132 can apply the equation below, and repeat this procedure over a range of angles.

$$\lambda = \frac{1}{t_f - t_i}\sum\nolimits_{i=1}^{S} \log_2 \frac{\|r_{i+1} - r_i\|}{\|r_i - r_{i-1}\|}$$

Lambda (λ) is an approximation of the Lyapunov exponent. If the standard deviation of the values of λ calculated for each θ is low, the rhythm is considered regular. If the standard deviation is high, the rhythm is considered chaotic.

In some embodiments, algorithm 5100 includes "Dominant Cycle Length" algorithm 5140. Dominant cycle length algorithm 5140 can include various algorithms that provide various methods of determining the cycle length of recorded cardiac signals. For example, dominant cycle length algorithm 5140 can include various "Cycle Length" algorithms, such as Cycle Length algorithm 5141 and Cycle Length algorithm 5142, each described herein. Cycle length algorithm 5141 is described in reference to FIGS. 15A-C and otherwise herein. Cycle length algorithm 5142 is described in reference to FIGS. 16A-D and otherwise herein.

In some embodiments, algorithm 5100 includes Control algorithm 5150 that is configured to determine if the timing of stimulation aligns with the excitable gap of the cardiac cycle, and/or if the pacing has otherwise captured the substrate. Control algorithm 5150 can include "Capture Assessment" algorithm 5151, for example as described in detail herebelow in reference to FIGS. 18A-C.

In some embodiments, Adaptation algorithm 5160 of algorithm 5100 is configured to determine if and/or how the pacing parameters should be adjusted. Adaptation algorithm 5160 can include "Substrate Response" algorithm 5161 configured to analyze recorded electrical data and to determine the response of the cardiac substrate to pacing pulses that are delivered (e.g., the electrical response of that delivery). In some embodiments, adaptation algorithm 5160 can include "Phase Alignment" algorithm 5162 configured to adjust the phase of delivered pacing, for example as described in reference to FIGS. 17A-B and otherwise herein.

During each step of algorithm 5100, one or more functional algorithms (e.g., one or more algorithms of algorithm 500 described herein) are performed. In Step 1, ID 100 (e.g., via algorithm 500) monitors the rhythm of the cardiac substrate, for example using rhythm detection algorithm 5130. ID 100 can evaluate the state of the cardiac substrate, determine the dominate cycle length, evaluate synchronization across the substrate, and/or determine whether the substrate is regular or chaotic. ID 100 can determine the dynamic state of the recorded rhythm, for example to determine if the rhythm is regular or chaotic. ID 100 can also determine the appropriate pacing cycle length (e.g., if atrial fibrillation is detected).

In Step 1, algorithm 5100 and associated algorithms are responsible for determining system state and measuring cycle length. For example, Rhythm Detection algorithm 5130 can determine whether activation is regular or chaotic, and/or can determine whether the activation is arrhythmogenic or not. This determination can be achieved by using one or more of the sync index algorithms described herein. Additionally or alternatively, a coarse determination can be made as to whether AF is present or not, for example by utilizing signals acquired from one or more body surface electrode signals, such as by looking for a singular 'p' wave and/or rapid, variable QRS complexes. In some embodiments, once the rhythm state is determined and established as normal or arrhythmogenic, cycle length measurements can be made by algorithm 5130, such as measurements made for a single electrode and/or for a group of electrodes within a region. Cycle length can be measured by the various cycle length algorithms described herein.

In Step 2, ID 100 configures pacing parameters (e.g., algorithm 5100 determines one or more parameters of pacing energy to be delivered) based on recorded and determined cardiac substrate conditions, for example based on the determined dominant cycle length and/or the state of the substrate. ID 100 provides pacing to the cardiac substrate using these pacing parameters. For example, in Step 2, algorithm 5100 measures the cycle length, assigns one or more groups of electrodes (e.g., electrodes 111 from which to provide pacing energy), determines the cycle length of the pacing to be delivered, and/or initiates the delivery of pacing based on the pacing parameters.

Once pacing is initiated in Step 2, the substrate is monitored for capture and control, as described herein. Capture and control can be both locally and regionally assessed, for example using a sync index algorithm described herein, and/or by otherwise evaluating the signals from the sensing electrodes. Lack of local capture can result in an adjustment to cycle length and/or an adjustment to the timing of the pacing (e.g., "phase alignment" performed by adaptation algorithm 5160). Successful local capture on all electrodes within a given region can be evaluated by capture assessment algorithm 5151 described herein. Failure to achieve regional control can result in a timing adjustment (e.g., a phase alignment) to one or more sites within a given region. In some embodiments, regional control can be exhibited by all assigned regions with a timing offset between one or more regions. In Step 3, ID 100, using control algorithm 5150, determines if local capture has been achieved (e.g., if capture has been achieved within a local "zone" of the cardiac tissue). For example, control algorithm 5150 can determine if the pacing electrodes (or groups of electrodes) are capturing the substrate, such as via capture assessment algorithm 5151, described herein. In Step 4, if local capture has been achieved, ID 100, using Control algorithm 5150, determines if regional control has been achieved. In some embodiments, regional control is achieved with the successful capture of all (or at least a majority) of the pacing electrodes within a group of electrodes (e.g., a group of electrodes determined by algorithm 5100 to deliver pacing to a portion of the cardiac substrate). For example, regional control of the posterior wall can be achieved when the activity on the posterior wall is being controlled by the pacing delivered via the electrode group on the posterior wall. In either Step 3 or Step 4, if local capture or regional control, respectively, have not been achieved, Algorithm 5100 continues to Step 5. In Step 5, ID 100, using Adaptation algorithm 5160, modifies one or more of the pacing parameters, such as to better achieve the local capture and/or regional control. For example, Adaptation algorithm 5160 can be configured to adjust the amplitude, frequency, and/or phase of the of the pacing pulses delivered. For example, adaptation algorithm 5160 can be configured to advance or delay the onset of the pacing pulse to align (e.g., temporally align) with and "fall within" the excitable gap.

Following Step 4, if regional control has been achieved, algorithm 5100 continues to Step 6. In Step 6, ID 100, using Control algorithm 5150, determines if global synchrony has been achieved. In some embodiments, global synchrony is achieved with the successful capture of all (or at least a majority) of the pacing electrodes within each group of electrodes (e.g., each group of electrodes determined by algorithm 5100 to deliver pacing to a portion, or "zone", of the cardiac substrate), and the alignment between the various regions (or "zones") of the capture. If global synchrony has not been achieved, algorithm 5100 continues to Step 7. In Step 7, ID 100, using Adaptation algorithm 5160, modifies one or more of the pacing parameters to better achieve global synchrony. For example, Adaptation algorithm 5160 can adjust the timing of pulses delivered between various regions of the cardiac substrate to achieve global synchrony. For example, when regional control has been achieved across all regions, but the control is not aligned across regions, pacing can be adjusted by advancing or delaying the onset of pacing in various regions to align the pacing prior to inhibition. After Step 5 and/or Step 7, algorithm 5100 returns to Step 2, where pacing is delivered, and Steps 3, 4, and 6 are repeated to check for local capture, regional control, and global synchrony, respectively. After Step 6, if global synchrony has been achieved, algorithm 5100 continues to Step 8, where ID 100 continues the pacing delivery to inhibit the atrial fibrillation. In some embodiments, after atrial fibrillation has been inhibited, pacing can be discontinued, and algorithm 5100 can return to Step 1, where ID 100 monitors the rhythm of the cardiac substrate.

Figure 3:
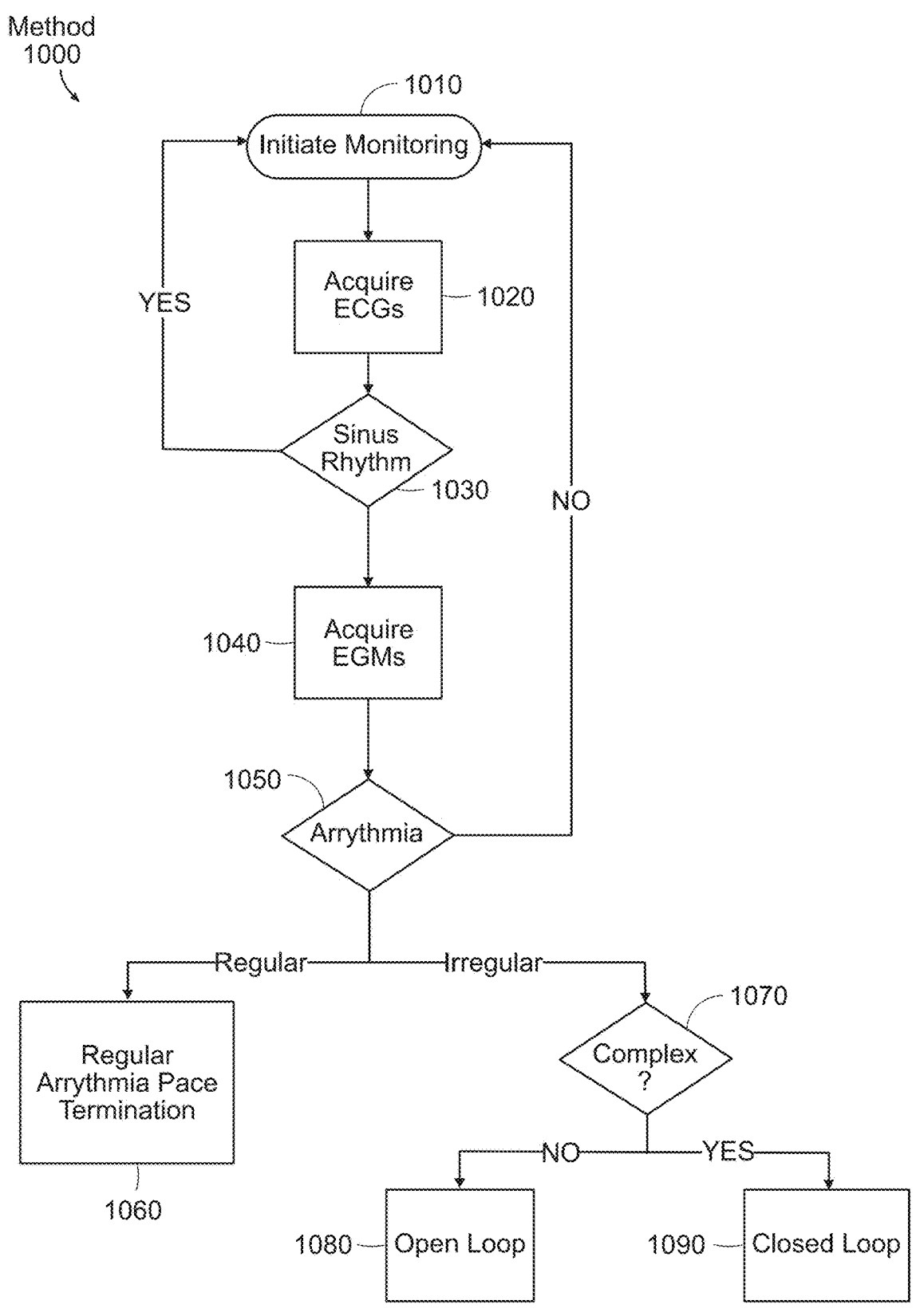
FIG. 3 illustrates a method of monitoring for and/or treating an arrythmia, consistent with the present inventive concepts.

Referring now to FIG. 3, a method of monitoring for and/or treating an arrythmia is illustrated, consistent with the present inventive concepts. Method 1000 of FIG. 3 can be performed by one or more components of system 10 described herein. In Step 1010 patient monitoring is initiated (or continues), for example where one or more patient signals (e.g., ECG signals) are recorded and analyzed by system 10 in Step 1020. In Step 1020, a first set of patient signals are recorded. In some embodiments, the first set of signals are recorded from a location removed from the heart, for example from or near the skin of the patient, such as from ID 100*b* and/or EPD 200*a*. In some embodiments, ID 100*b* comprises a housing such as a "can" similar to an IPG, and one or more electrodes 111*b* can be integral to the can, in contact with the surrounding tissue. In Step 1030, a first level of analysis is performed (e.g., analysis performed by algorithm 500 of ID 100) on the first set of patient signals recorded in Step 1020. In some embodiments, the first level of analysis comprises an analysis with a first level of complexity (e.g., a "simple" analysis), such as an analysis to determine if the patient is in sinus rhythm. In some embodiments, this simple analysis requires less computational power, such as when the analysis requires less energy to perform, than more complex analyses performed later in method 1000, described herein. For example, the simple analysis may require less peak computational power at any point during its execution, and/or may require less total power to execute than more complex analyses of method 1000. In Step 1030, if sinus rhythm has been detected, method 1000 returns to Step 1010 and monitoring continues. If sinus rhythm is not detected, method 1000 continues to Step 1040, and a second set of patient signals (e.g., EGMs) are recorded. In some embodiments, the second set of signals are recorded from a location proximate the heart, for example from electrodes 111*a* of ID 100*a* positioned on the epicardial wall. In some embodiments, the second set of signals comprise a higher resolution than the first set of signals recorded in Step 1020. In some embodiments, the second set of signals are recorded via a greater number of electrodes than the first set of signals recorded in Step 1020, such as when the second set of signals are recorded via the same electrodes as the first set of signals as well as one, two, or more additional electrodes, or when the second set of signals is recorded via a unique set of electrodes comprising at least one, two, or three more electrodes than the set of electrodes used to record the first set of signals. In some embodiments, the second set of signals are recorded via a set of electrodes that are more spatially distributed than the electrodes used to record the first set of signals In Step 1050, a second level of analysis is performed (e.g., analysis performed by algorithm 500 of ID 100). The analysis of Step 1050 can be performed on the first and/or the second set of signals recorded in Steps 1020 and 1040, respectively. In some embodiments, the first set of recorded signals comprises a shorter recording than the second set (e.g., recorded over a shorter period of time), and/or comprises a dataset comprising less information, such as a dataset recorded at a lower sample rate (or lower resolution), and/or from less recording devices (e.g., electrodes 111 and/or other sensors of ID 100 and/or other devices of system 10). The analysis of Step 1050 can determine if the detected arrythmia is regular or irregular. If the arrythmia is determined to be regular, method 1000 continues to step 1060, and if the arrythmia is determined to be irregular, method 1000 continues to step 1070. In Step 1060, system 10 delivers therapy (e.g., pacing energy via one or more electrodes 111) to pace terminate the regular arrythmia. Once the arrythmia has been pace terminated, method 1000 can return to Step 1010. If an irregular arrythmia is detected in step 1050, additional analysis can be performed in Step 1070 to determine the complexity of the arrythmia (e.g., if the complexity is above a threshold level). In some embodiments, complexity can be categorized by average cycle length and/or cycle length variability. For example, shorter average cycle lengths with more variability are more complex than longer cycle lengths with minimal variability. If the arrythmia is determined to be non-complex, method 1000 continues to Step 1080, where open-loop stimulation is applied to treat the arrythmia. Alternatively, if the arrythmia is determined to be complex, method 1000 continues to Step 1090, where closed-loop stimulation is applied to treat the arrythmia. After treatment is provided in Steps 1080 and/or 1090 (e.g., after the patient has been restored to sinus rhythm), method 1000 can return to Step 1010.

In some embodiments, "open-loop" stimulation refers to a method for applying stimulation to a heart in either an irregular and/or regular pattern calculated from a deterministic formula that is imposed upon the cardiac substrate to globally entrain and drive atrial fibrillation from irregular to regular. Similar to "phase locking", the stimulation pattern can be gradually varied to draw the operating point of the substrate from greater complexity to lower complexity and terminate atrial fibrillation into sinus rhythm. Pacing can be delivered in this method simultaneously to all atrial contacting electrodes (e.g., electrodes 111) on ID 100. Once the substrate has been synchronized to stimulate from all electrodes 111, a transition to regular pacing with gradually prolonged cycle lengths occurs.

In some embodiments, "closed-loop" stimulation refers to a method based on the detection of specific signal features characterizing the conduction pattern to apply an irregular stimulation pattern to a heart that is concordant with the underlying fibrillatory substrate. Detection of approaching wavefronts and/or characterization of cardiac state (e.g., conduction velocity, relative activation time between electrodes, and/or activation sequence) initiate independent application of irregular stimuli through a well-distributed array of electrodes (e.g., array 110 of electrodes 111). For example, each electrode can operate independently to insert pacing pluses within sensed excitable gaps. Stimulation results in the expansion of local activation which enlarges the regions of refractoriness. Activation can converge (e.g., gradually converge) with stimulation from each electrode until all electrodes are pacing in unison, resulting in global coalescence of refractoriness and ultimately termination of atrial fibrillation. In some embodiments, each electrode 111 operates independently to insert pacing pulses within sensed excitable gaps. Activation can gradually converge with stimulation from each electrode 111 until all electrodes are acting in unison.

In some embodiments, method 1000 executes (e.g., an algorithm 500, such as algorithm 135 of ID 100 initiates Step 1010 of method 1000) periodically, such as at least once per minute, at least once every 15 minutes, at least once per hour, at least once per every four hours, at least four times per day, at least twice per day, and/or at least once per day. Alternatively or additionally, method 1000 can run continuously and/or semi-continuously, such as when Step 1010 automatically starts after the completion of Steps 1030, 1050, 1060, 1080, and/or 1090. In some embodiments, a user of system 10 (e.g., the patient and/or a clinician of the patient) can initiate method 1000 and/or can determine the frequency of initiation and/or the duration of continuous monitoring by method 1000. For example, the patient can initiate method 1000 under circumstances in which an arrythmia is expected, for example when the patient is experiencing angina or other potential perceptible symptoms. In some embodiments, algorithm 500 is configured to determine the frequency of execution of method 1000, such as when algorithm 500 is configured to determine the frequency based on recordings of one or more patient parameters. For example, when algorithm 500 identifies arrhythmic events occurring at an average frequency (e.g., a high average frequency), algorithm 500 can specify the execution of method 1000 at a frequency based on the average frequency of the arrhythmic events, for example at least as frequent, twice as frequent, or other frequency selected to increase the likelihood of identifying any future arrhythmic event. In some embodiments, algorithm 500 is configured to adjust the frequency of execution of method 1000 over time, for example as a history of arrhythmia prevalence is established. For example, the frequency of execution of method 1000 can be high initially (e.g., when ID 100 is implanted into the patient), and can be decreased by algorithm 500 over time, such as when the prevalence of arrhythmia is decreased as the cardiac substrate remodels.

Patient signals recorded in Steps 1020, 1040, and/or 1070 can be recorded from one or more externally placed and/or implanted sensors of system 10. For example, patient signals, such as ECG signals, can be recorded from one or more externally positioned electrodes or other sensors, such as one or more functional element 299 of EPD 200 of FIG. 1. Additionally or alternatively, patient signals can be recorded from one or more electrodes 111 of ID 100 of FIG. 1 implanted subcutaneously, implanted on the epicardial wall of the heart (e.g., on the epicardial wall of the left atrium), and/or implanted inside the heart, such as on the septal wall of the right atrium and/or in the left atrial appendage (e.g., when at least a portion of an ID 100 of system 10 is implanted within the left atrial appendage, such as when an ID 100 comprises a left atrial appendage closure device).

In some embodiments, ID 100 comprises one or more electrodes 111 configured to deliver energy to pace the heart, such as in Steps 1060, 1080, and/or 1090. Electrodes 111 can be positioned on or near the atrial wall, for example on the epicardial wall, on the endocardial wall, and/or within a vessel proximate the atria, such as described herein. System 10 can be configured to perform open-loop pace-termination of atrial fibrillation to return the patient to sinus rhythm, for example in Step 1080 of method 1000. Additionally or alternatively, system 10 can be configured to perform closed-loop pace-termination of atrial fibrillation to return the patient to sinus rhythm, for example in Step 1090 of method 1000. For example, during closed-loop pacing, system 10 can be configured to record patient data, and algorithm 500 can be configured to analyze the data to identify regularization of atrial rhythm (e.g., a return to sinus rhythm) and discontinue pacing.

In some embodiments, system 10 is configured to identify one or more types of events that may occur, such as events that occur during the execution of method 1000. For example, an event can comprise the detection of an arrhythmia, the initiation or termination of pacing, the termination of an arrhythmia, and/or other system 10 or patient related event. In some embodiments, system 10 is configured to record the occurrence of an event identified by system 10 (e.g., to create a log of identified events). Additionally or alternatively, system 10 can be configured to provide an alert to a user, such as the patient and/or a clinician of the patient, based on the occurrence of an event (e.g., an event identified during the execution of method 1000). In some embodiments, the repeated occurrence of a particular event may trigger an alert, for example when an event occurs multiple times within a particular time period (e.g., if an arrhythmia is detected and treated more than twice in a one-hour period). In some embodiments, a recorded event may trigger one or more functions of system 10, for example if an adverse cardiac event is detected (e.g., tissue ischemia and/or heart failure is detected), system 10 can be configured to alert a clinician of the patient (e.g., via network 50, such as a cellular network) and/or to deliver cardioversion via ID 100.

In some embodiments, in Steps 1050 and/or 1070, further analysis of the signals recorded in Steps 1020 and/or 1040 is performed by algorithm 500. For example, algorithm 500 can analyze one or more signal characteristics selected from the group consisting of: cycle length; variability; timing between electrodes of known locations; conduction time; relative time of activation among electrodes; sequence of activation that differentiates normal cardiac tissue from that which is fibrotic; and combinations of these. Algorithm 500 can analyze these characteristics to rank the complexity of the detected arrythmia (e.g., to rank the AF). In some embodiments, as shown, open-loop pacing is used by system 10 to treat coarse AF (e.g., in Step 1080) and closed-loop pacing is used by system 10 to treat complex AF (e.g., in Step 1090). Alternatively or additionally, open-loop stimulation can be used to treat complex AF, and/or closed-loop stimulation can be used to treat coarse AF. In some embodiments, system 10 can be configured to transition between open and closed-loop pacing based on the response of the tissue (e.g., to switch from closed-loop pacing to open-loop pacing after the atria responds as expected to closed-loop pacing). In some embodiments, algorithm 500 can analyze the timing between electrodes of known locations to assess stretching of the cardiac tissue, which may indicate progressive heart failure. For example, ID 100 can comprise two or more electrodes 111 positioned on the left ventricle such that algorithm 500 can assess stretch of the left ventricle by analyzing changes in signal timing between the two electrodes.

In some embodiments, in Step 1020, signals are recorded from one or more body surface electrodes (e.g., one or more functional elements 299 of EPD 200), and/or from one or more subcutaneous electrodes (e.g., one or more electrodes 111 of an ID 100 implanted subcutaneously). In Step 1030, if normal sinus rhythm is not and/or cannot be detected (e.g., sinus rhythm cannot be definitively detected) using the signals recorded in Step 1020, additional signals can be recorded in Step 1040 comprising intracardiac signals recorded from one or more electrodes positioned proximate the heart (e.g., one or more electrodes 111 of an ID 100 implanted proximate the left atrium). These intracardiac signals can be analyzed in Step 1050 to determine if sinus rhythm can be detected. In some embodiments, signals (e.g., EGMS) are only recorded from electrodes 111 of ID 100 positioned proximate the heart if sinus rhythm cannot be detected from signals recorded from other devices of system 10, such as require less power from ID 100 (e.g., less power stored on and/or transferred to ID 100). For example, ID 100 is only powered (e.g., wirelessly supplied power from a separate device of system 10, such as a second ID 100 implanted subcutaneously, and/or an EPD 200 positioned outside the body) when signals are required to be recorded from proximate the heart (e.g., EGMs). Alternatively, method 1000 skips Steps 1020 and 1030, and the recording of signals (e.g., EGMs) and/or the processing of signals is performed initially by ID 100, for example when ID 100 is wired to a source of power, such as to a subcutaneously implanted second ID 100 comprising a battery and/or capacitor.

As described herein, algorithm 500 can identify normal sinus rhythm, regular arrythmias, and/or irregular arrythmias. In some embodiments, normal sinus rhythm (e.g., as measured from body surface and/or subcutaneous electrodes) can be defined as having a mean R-R interval greater than 550 ms and a cycle length variability of less than 20%. Regular arrythmias (e.g., flutter or automatic focal tachycardia), for example as measured by one or more intracardiac electrodes of ID 100, can be defined as having a mean atrial cycle length that range from 250-450 ms, an atrial cycle length variability of less than 5%, and/or ventricular R-R variability less than 5% during one-to-one atrioventricular conduction (e.g., when every atrial beat conducts to and activates the ventricle). Irregular arrythmias, for example as measured by one or more intracardiac electrodes of ID 100, can be defined as having a mean atrial cycle length shorter than 250 ms, a cycle length variability greater than 10%, and/or ventricular R-R variability greater than 15%.

Figure 4:
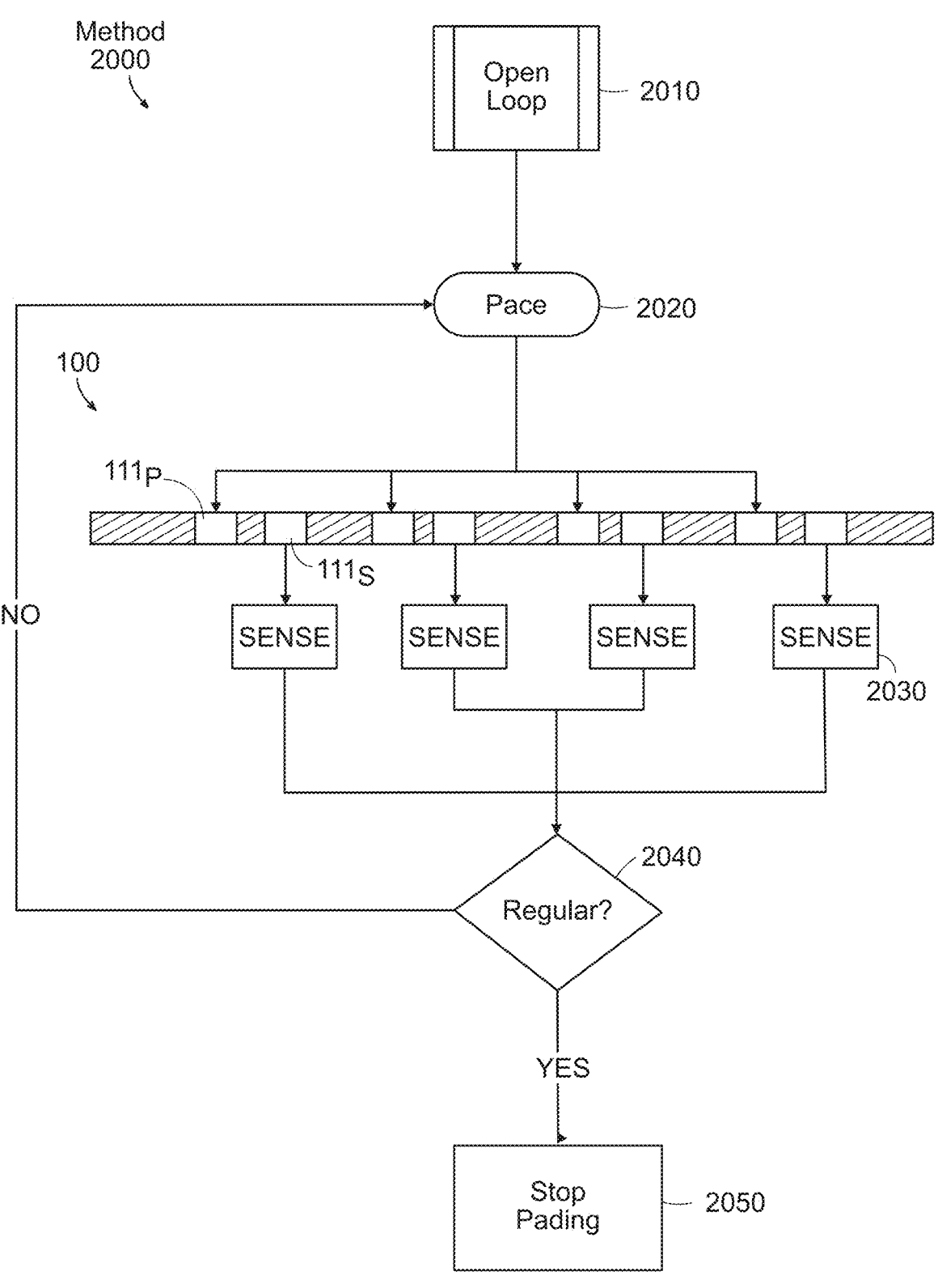
FIG. 4 illustrates a flow chart including a partial schematic, consistent with the present inventive concepts.

Referring now to FIG. 4, a flow chart including a partial schematic is illustrated, consistent with the present inventive concepts. Method 2000 is a method for applying stimulation energy to pace the heart in an open-loop manner. Method 2000 can be performed using the devices of system 10 described herein. In Step 2010, system 10 has identified an arrythmia, and open-loop pacing has been identified (e.g., by algorithm 500) to treat the arrythmia. Open-loop stimulation energy can be delivered in an irregular or a regular pattern, such as a pattern that has been determined by system 10 to globally entrain AF and/or to drive AF from irregular to regular. In some embodiments, the stimulation pattern is calculated by system 10 by applying a deterministic formula that is imposed upon the cardiac substrate.

In Step 2020, stimulation energy is delivered in the determined pattern (e.g., a stimulation sequence is delivered) via electrodes 111 of ID 100, as shown. In some embodiments, ID 100 comprises two sets of electrodes 111, electrodes 111P from which stimulation energy is delivered, and electrodes 111s configured to sense cardiac signals (e.g., EGMs) in Step 2030 after the stimulation sequence has been delivered. In some embodiments, electrodes 111s comprise pairs of electrodes configured for bipolar sensing of cardiac signals. Alternatively or additionally, two, three, or more electrodes 111s can be configured for bipolar sensing when paired with a shared reference electrode 111s. In Step 2040, system 10 analyzes the signals recorded in Step 2030 to determine if sinus rhythm has been restored. If sinus rhythm is detected, open-loop pacing is ceased in Step 2050. In Step 2040, if an arrythmia is still present, an additional stimulation sequence is delivered in Step 2020. Pacing and sensing can continue until sinus rhythm is detected in Step 2040. In some embodiments, stimulation energy can be delivered from one or more electrodes 111 simultaneously or in a multiplexed arrangement to individual electrodes 111 sequentially, such as in a random pattern or in a predetermined pattern. In some embodiments, neighboring electrodes 111 can be configured such that each of the neighboring electrodes are used to both deliver pacing energy and to sense cardiac activity, or such that one electrode is configured to deliver pacing energy (an electrode 111) and one electrode is configured to sense (an electrode 111s), as shown.

In some embodiments, the pattern of the stimulation sequence delivered in Step 2020 is gradually varied (e.g., each time Step 2020 is executed) to draw the operating point of the cardiac substrate from greater complexity to lower complexity and terminate AF into sinus rhythm. In some embodiments, the deterministic formula applied by algorithm 500 to determine the pattern of the stimulation sequence to be delivered is fractal in nature. For example, the formula can comprise a 2nd order non-linear population growth formula which predicts the irregular, sequential behavior of natural phenomena, such as fibrillation. In some embodiments, the formula is similar to the Hurst Formula which predicts non-linear, irregular trends in the stock market. Alternatively or additionally, the formula can be similar to the formula for Brownian Noise ($1/f^2$) which describes non-linear, irregular perturbations in electronic devices. Method 2000 can be executed by system 10 during AF to entrain fibrillatory conduction. This can be achieved by setting the average initial pacing cycle length (the cycle length of the stimulation sequence) to one of the following conditions: match the average fibrillatory cycle length; incrementally exceed the average fibrillatory cycle length up to 20%; decrementally lag the average fibrillatory cycle length up to 20%; vary the pacing cycle length by a percentage but to not exceed the average intrinsic cycle length; and combinations of these. In some embodiments, control of a substrate's operating point (e.g., control of the cardiac substrate) manifests as prolongation of the fibrillatory cycle length, and can be achieved by adjusting the initial pacing cycle length by: gradually prolonging the pacing cycle length by a fixed increment, such as by 10 ms, 20 ms, or 100 ms, for an integer number of time periods, such as 2, 5, or up to 30 time periods; or by gradually prolonging the pacing cycle length as a percentage of the initial pacing cycle length, such as by 20%, 70%, or up to 500%. Additionally or alternatively, control of a substrate's operating point can manifest as advancement of the fibrillatory cycle. Advancement can comprise the electrical stimulation of a wave of activation imposed at an instant of time that is earlier than the instant when "natural", baseline activation would have occurred (referred to herein as "premature" stimulation). Premature stimulation can be denoted "S2" and can be referred to as the "S1-S2 coupling interval". In some embodiments, S2 advances the physiologic "phase" of action potentials "forward" to an earlier instant of time, relative to the time of natural, baseline activation. A sequence of premature stimulation pulses can be denoted "(S2, S3, . . . Sn)". The coupling intervals can be equal or unequal. Advancement of activation can be imposed indefinitely, as long as the coupling intervals do not encroach upon the end of the refractory period for the previous cycle (e.g., the present wavefront must not coincide with or overlay upon the previous waveback).

In some embodiments, the deterministic formula applied by algorithm 500 to determine the pattern of the stimulation sequence can comprise a fractal pattern determined by system 10 by analyzing the cardiac substrate (e.g., and extracting a fractal pattern). For example, system 10 can be configured to monitor the atrial fibrillation and to characterize the pattern of cycle-to-cycle intervals. System 10 can be further configured (e.g., via an algorithm of system 10, such as algorithm 135 and/or 215) to determine a fractal pattern based on the characterized atrial fibrillation, such as by identifying an existing fractal that best matches the pattern of the cycle-to-cycle interval variation, and/or by using the exact characterized atrial fibrillation pattern itself. System 10 can then apply stimulation in this pattern.

Figure 4A:
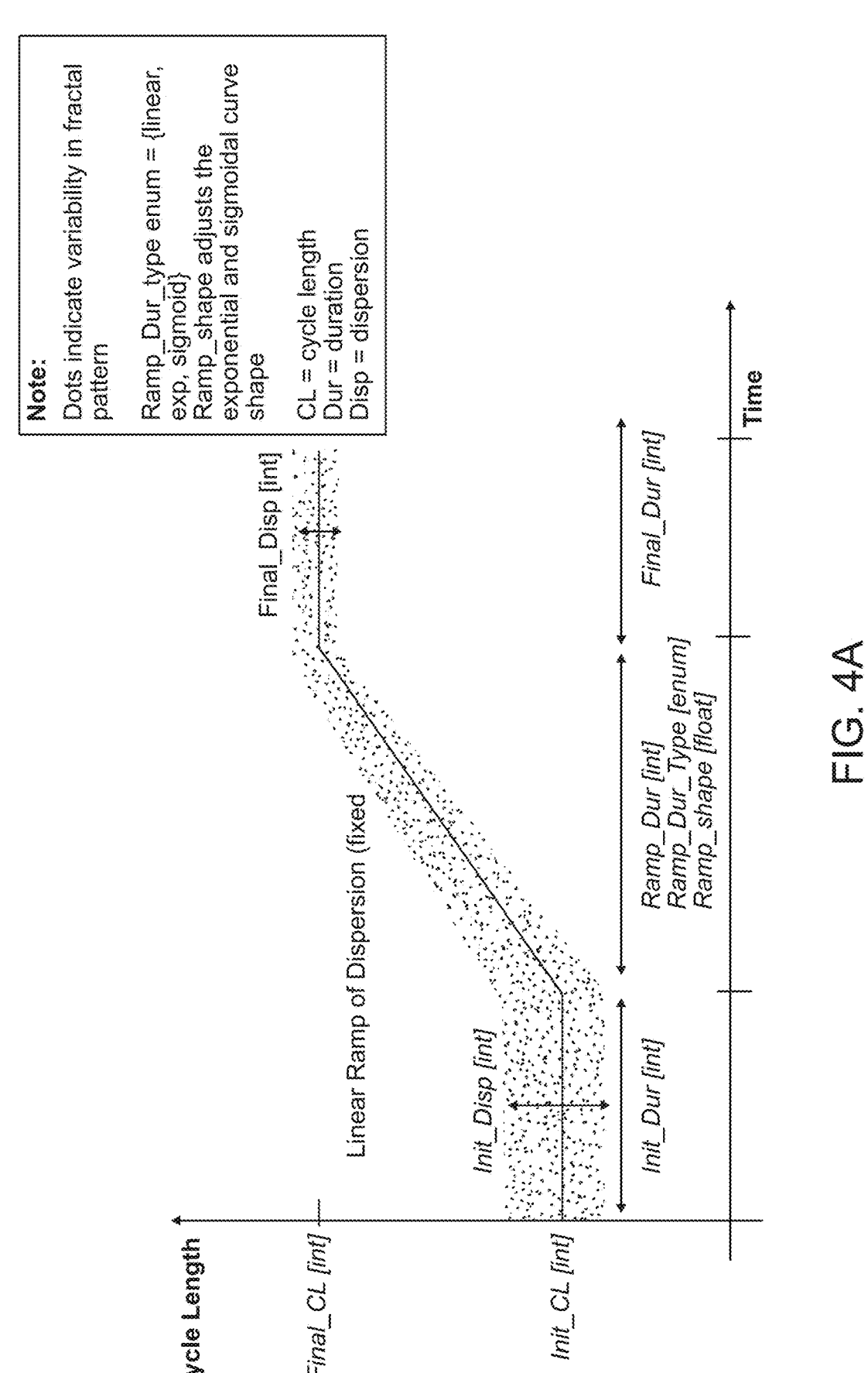
FIG. 4A illustrates a diagram of configurable pacing parameters, consistent with the present inventive concepts.

Referring additionally to FIG. 4A, a diagram of configurable pacing parameters is illustrated, consistent with the present inventive concepts. In some embodiments, the parameters of the stimulation energy delivered during open-loop pacing in Step 2020 of method 2000 are configurable and/or adaptable by system 10 (e.g., as determined by algorithm 500). In some embodiments, these parameters can be uniquely configured for one or more groups of one or more electrodes 111. The configurable parameters of the stimulation energy can be selected from the group consisting of: initial cycle length; final cycle length; initial duration; ramp duration; ramp duration type; ramp shape; final duration; initial dispersion; final dispersion; and combinations of these. In some embodiments, the initial cycle length (Init_CL) is determined (e.g., by algorithm 500) to match the mean or the median cycle length of the intrinsic rhythm. In some embodiments, the final cycle length (Final_CL) is the target cycle length to regularize the cardiac rhythm. The initial duration (Init_Dur) is the determined time interval in which the initial pacing cycle is applied. The ramp duration (Ramp_Dur) is the determined time interval in which the pacing cycle length is progressively increased. The ramp duration type (Ramp_Dur_Type) is the type of ramp that connects the initial cycle length to the final cycle length, for example a linear, exponential, or a sigmoidal ramp. The ramp shape (Ramp shape) can comprise the specific parameters that define the shape of each ramp type. The final duration (Final_Dur) is the time interval in which the final pacing cycle is applied. The initial dispersion (Init Disp) is the degree of variation in pacing cycle length as a percentage of the mean or median intrinsic cycle length (e.g., 5%, 20%, or 50%). The final dispersion (Final_Disp) is the degree of variation in the final pacing cycle length. In some embodiments, the final dispersion is calculated based on the initial dispersion, or as a percentage of the mean or median target length (e.g., 5%, 20%, or 50%). In some embodiments, the maximum dispersion is no greater than the average intrinsic cycle length.

Figure 4B:
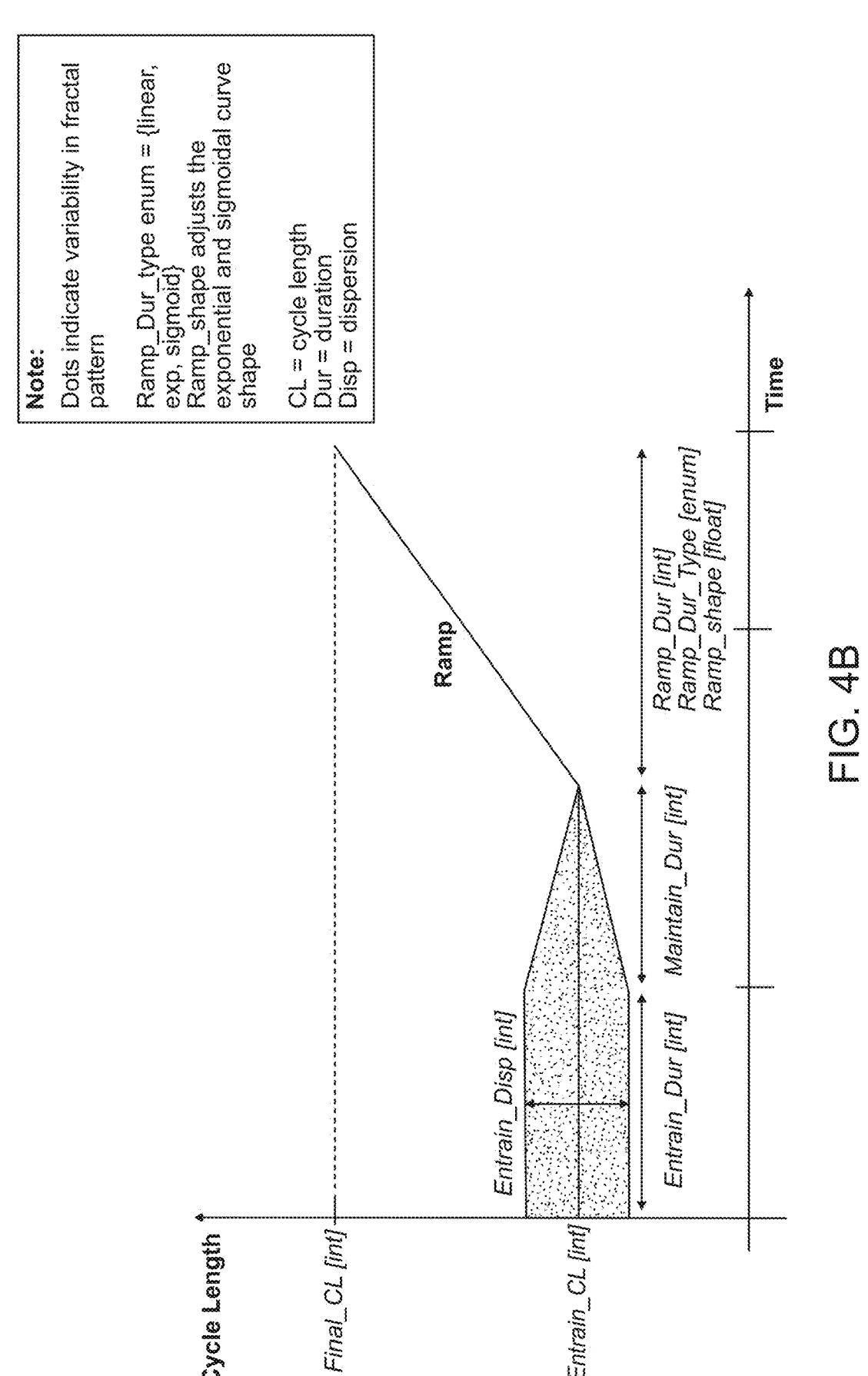
FIGS. 4B and 4C illustrate alternate diagrams of configurable pacing parameters, consistent with the present inventive concepts.
Figure 4C:
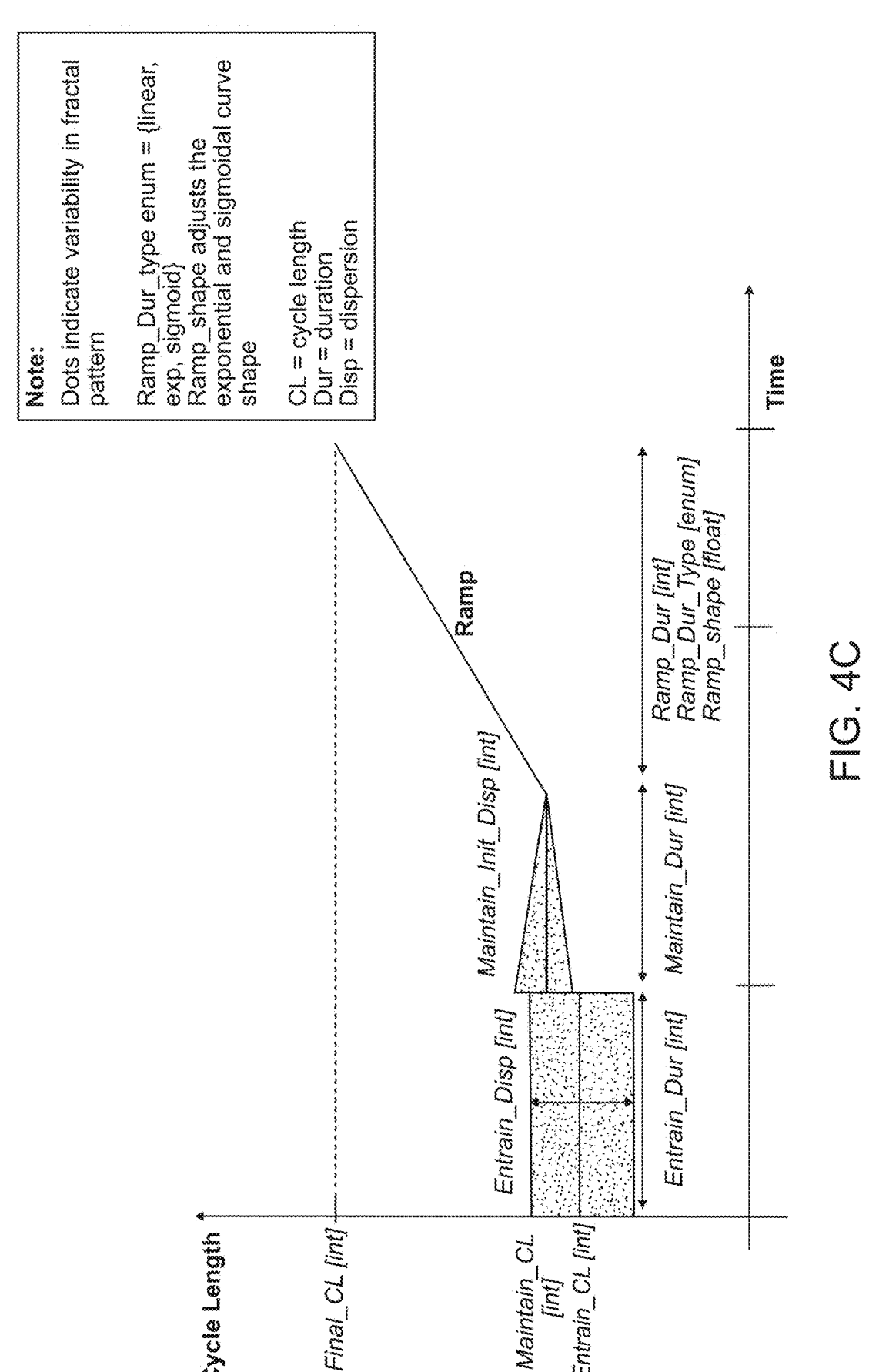

Referring additionally to FIGS. 4B and 4C, alternate diagrams of configurable pacing parameters are illustrated, consistent with the present inventive concepts. In some embodiments, transitions between the pacing modes shown can be triggered algorithmically and/or manually.

Figure 5:
FIG. 5 illustrates a flow chart including a partial schematic, consistent with the present inventive concepts.

Referring now to FIG. 5, a flow chart including a partial schematic is illustrated, consistent with the present inventive concepts. Method 3000 is a method for applying stimulation energy to pace the heart in a closed-loop manner. Method 3000 can be performed using the devices of system 10 described herein. In Step 3010, system 10 has identified an arrythmia, and closed-loop pacing has been identified (e.g., by algorithm 500) to treat the arrythmia. Closed-loop stimulation can be delivered based on the detection of specific signal features that characterize the conduction pattern. The stimulation can comprise an irregular stimulation pattern that is concordant with the underlying fibrillatory substrate. In some embodiments, the detection of approaching wavefronts (e.g., wavefronts approaching an electrode 111 of ID 100) and/or the characterization of system state (e.g., conduction velocity, relative activation between electrodes 111, and/or activation sequence) initiate independent application of irregular stimuli through a well-distributed array of electrodes (e.g., array 110 of electrodes 111). Closed-loop pacing provided by system 10 can be implemented to result in the independent expansion of local activation, which enlarges the regions of refractoriness resulting in global coalescence of refractoriness, and ultimately the termination of atrial fibrillation. In some embodiments, system 10 is configured to analyze one or more recorded signals to characterize the cardiac substrate, such as to differentiate normal cardiac tissue from fibrotic cardiac tissue. This characterization can be referenced by algorithm 500 when determining the pattern of stimulation to be applied (e.g., from which electrodes 111 pacing pulses should be delivered, and when).

In Step 3020, signals are recorded from one or more of electrodes 111 of ID 100. In Step 3030, the signals recorded from each electrode 111 are analyzed (e.g., by algorithm 500). If algorithm 500 determines that pacing energy should be delivered from an electrode 111, energy is delivered from the designated electrode in Step 3040. For example, if the analysis indicates the cardiac substrate is in an excitable state (e.g., an excitable gap is present), stimulation energy can be delivered. In some embodiments, stimulation energy can be delivered using an anodal biphasic methodology, which may accelerate the excitable gap allowing the pacing pulse to stimulate surrounding substrate. Otherwise, sensing continues in Step 3020 from that electrode 111. After Step 3040, cardiac signals are again recorded and analyzed in Step 3050, and if regular sinus rhythm is not detected, pacing can continue by returning to Step 3030. If regular sinus rhythm is detected, method 3000 continues to Step 3060 and pacing discontinues. Multiple loops of steps 3020 through 3050 can execute simultaneously for each electrode 111 of ID 100, as shown.

In some embodiments, closed-loop pacing algorithms (e.g., algorithm 500) conform to fibrillatory conduction, which can be fractal by nature and can be predicted by the $2^{nd}$ order population growth model. For example, event-based detection can leverage a set of fiducial features that correlate to clinically relevant phases of the fibrillatory conduction pattern (e.g., cycle length, peak negative derivative, peak positive derivative, maximum amplitude, or minimum amplitude). Each feature can be logically analyzed both individually and/or globally to initiate stimulation. In some embodiments, "system theory" based characterization of fibrillatory conduction establishes the primary parameters responsible for the operating point of the substrate (e.g., unipolar electrogram and multiple derivatives of the unipolar electrogram at spatially distributed locations). Each variable can be mathematically analyzed to determine the compensatory feedback required to shift the operating point of the substrate and terminate atrial fibrillation.

In some embodiments, in Step 3050, pacing is precisely inhibited when one or more of the following conditions are identified (e.g., identified by algorithm 500): global prolongation of cycle length by at least 20%; signal diminishes to baseline for a period of at least 20% longer than average fibrillatory cycle length; and/or refractory loss of capture. Once pacing is inhibited by one or more of these conditions, pacing is discontinued in Step 3060.

Referring now to FIGS. 6A-D and 7A-E, various pacing pulses are illustrated, consistent with the present inventive concepts. The pulses shown can be delivered via an electrode 111 of system 10, for example during open-loop and/or closed-loop pacing, such as during methods 2000 or method 3000 described herein. Applied pulses can comprise varying phase and/or polarity parameters. For example, FIGS. 6A and 6B show monophasic cathodal and anodal pulses, respectively. FIGS. 6C and 6D show biphasic cathodal and anodal pulses, respectively. Negative pulses (e.g., cathodal pulses) depolarize the tissue, while positive pulses (e.g., anodal pulses) hyperpolarize the tissue. In some embodiments, the goal of pacing applied by system 10 (e.g., as determined by algorithm 500) is to control the cardiac substrate, which can be achieved by using the stimuli (e.g., the stimulation energy) to depolarize as much substrate as possible. While this would imply that a cathodal monophasic pulse would be ideal, the use of an anodal biphasic pulse can potentially be used to accelerate cellular recovery (e.g., the refractory period) with the initial positive part of the pulse just before the subsequent negative pulse which increases the opportunity to depolarize and more-globally control a larger volume of tissue at any given instant. In some embodiments, cathodal biphasic pulses activate tissue at a lower threshold (e.g., a lower threshold than a monophasic pulse), and can comprise charge balanced pulses.

Figures 7A, 7B, 7C, 7D, 7E:
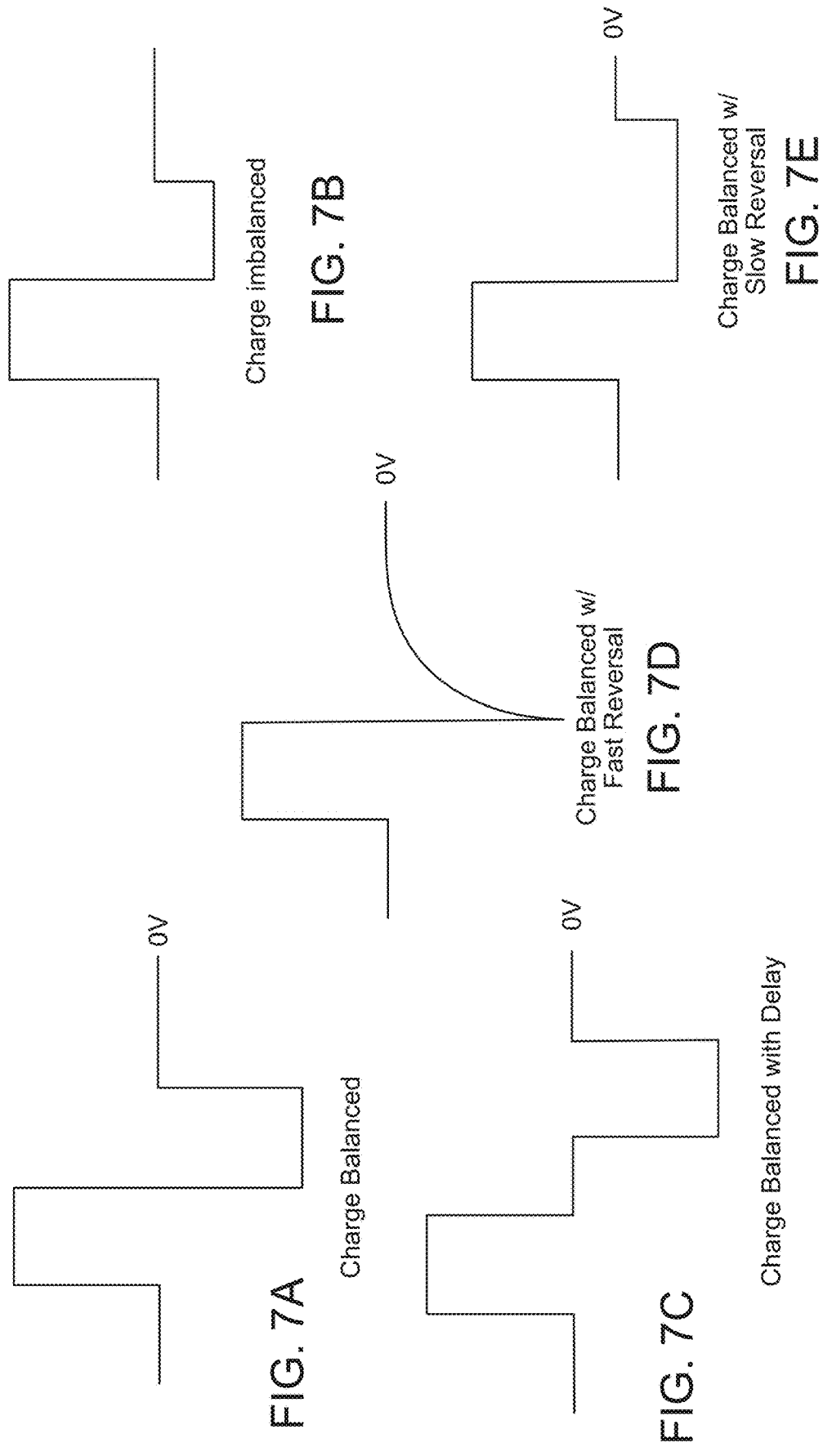

In some embodiments, combinations of the pulses shown in FIGS. 6A-6D can be used with various balancing schemes to optimally minimize the amount of residual charge left on an electrode 111 that may otherwise result in an artifact (e.g., an artifact in the recording performed after stimulation energy has been delivered). FIGS. 7A and 7B show balanced and imbalanced biphasic pulses, respectively. FIGS. 7C-E show balanced pulses with a delay, a fast reversal, and a slow reversal, respectively.

Referring now to FIGS. 8A-8E, a pair of anatomic views and various graphs of recorded electrical activity data are illustrated, consistent with the present inventive concepts. In some embodiments, algorithm 500 and/or algorithm 5100 of system 10 comprises an algorithm configured to evaluate the degree of irregularity of atrial activation patterns, a "Sync Index" algorithm, Sync Index algorithm 5131. Sync Index algorithm 5131 can evaluate unipolar and/or bipolar voltages measured with a limited number of distributed sensing electrodes (e.g., e.g., as few as one electrode), such as electrodes 111 distributed about the left atrium shown in FIG. 8A.

Figures 8A, 8B, 8C, 8D, 8E:
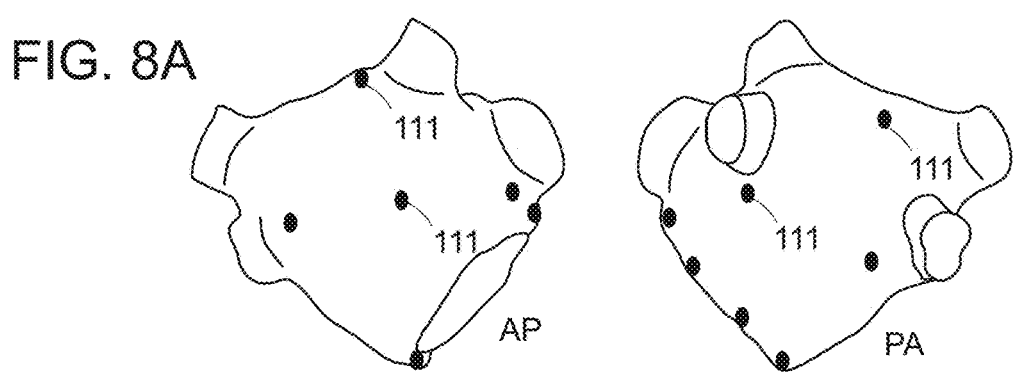
FIGS. 8A-E illustrate a pair of anatomic views and various graphs of recorded electrical activity data, consistent with the present inventive concepts.

In some embodiments, sync index algorithm 5131 is configured to apply signal conditioning to signals recorded from the limited number of distributed electrodes, as shown in FIG. 8B, such as to allow a reliable extraction of the phases, shown in FIG. 8C, from which the phase differences can be computed, as shown in FIG. 8D. Sync index algorithm 5131 can be configured to compute the time derivative of the phase differences to obtain the Sync Index shown in FIG. 8E. In some embodiments, the Sync Index is the mean and/or median of the time derivation of the phase differences shown in FIG. 8D, for example calculated using a moving median filter applied to minimize the effect of noise. In sinus rhythm, $\phi_i-\phi_j$ is constant, and the sync index is zero, as $$\frac{d\text{constant}}{dt} = 0.$$

The magnitude of the sync index increases with the irregularity of the rhythm. System 10 can be configured to apply a threshold to the magnitude of the sync index to categorize sinus rhythm, irregular atrial flutter, and atrial fibrillation. In some embodiments, sync index can be computed using cycle length data by recognizing that cycle length and phases are related by the equation $$\frac{d\phi}{dt} = \omega,$$

where $$\omega = \frac{2\pi}{CL}.$$

Figure 9:
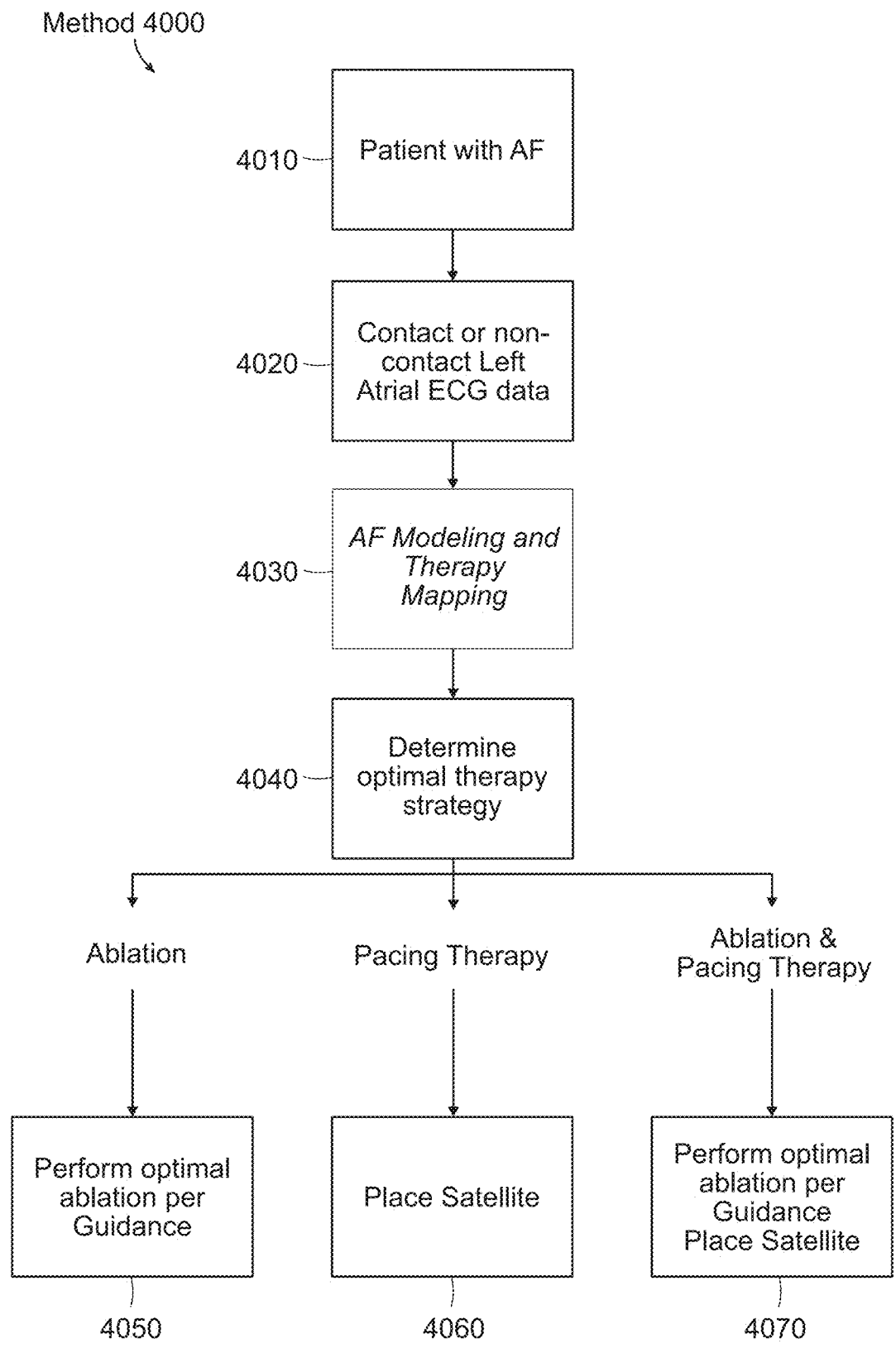
FIG. 9 illustrates a method of determining a treatment strategy for a patient suffering an arrythmia, consistent with the present inventive concepts.

Referring now to FIG. 9, a method of determining a treatment strategy for a patient suffering an arrythmia is illustrated, consistent with the present inventive concepts. Method 4000 can be executed using the devices of System 10 described herein. In Step 4010 a patient with an irregular heartbeat (e.g., AF) is selected for diagnosis and treatment. In Step 4020 cardiac data is recorded by system 10. For example, contact and/or non-contact ECG data (e.g., data recorded from and/or pertaining to the cardiac activity of the left atrium) is recorded by system 10, such as clinician device 300. In some embodiments, clinician device 300 comprises a mapping catheter configured to be inserted into the left atrium to map the cardiac activity of the atrium.

In Step 4030 algorithm 500 of system 10 analyzes the recorded cardiac data. The analysis can include AF modeling and/or therapy mapping. In Step 4040, based on the analysis performed in Step 4030, algorithm 500 identifies a therapy strategy. In some embodiments, the therapy strategy can be selected from: performing a cardiac ablation; performing pacing therapy, such as therapy delivered via an ID 100; and/or both performing an ablation and performing continued pacing therapy. If ablation is determined as the appropriate treatment by system 10 in Step 4040, ablation is performed in Step 4050. If pacing is determined to be the appropriate treatment, in Step 4060 ID 100 can be implanted into the patient. If both treatments are selected, in Step 4070, ablation treatment can be performed, and ID 100 can be implanted. In some embodiments, ID 100 is configured to perform spatiotemporal resynchronization therapy ("SRT"), as described herein.

Figure 10:
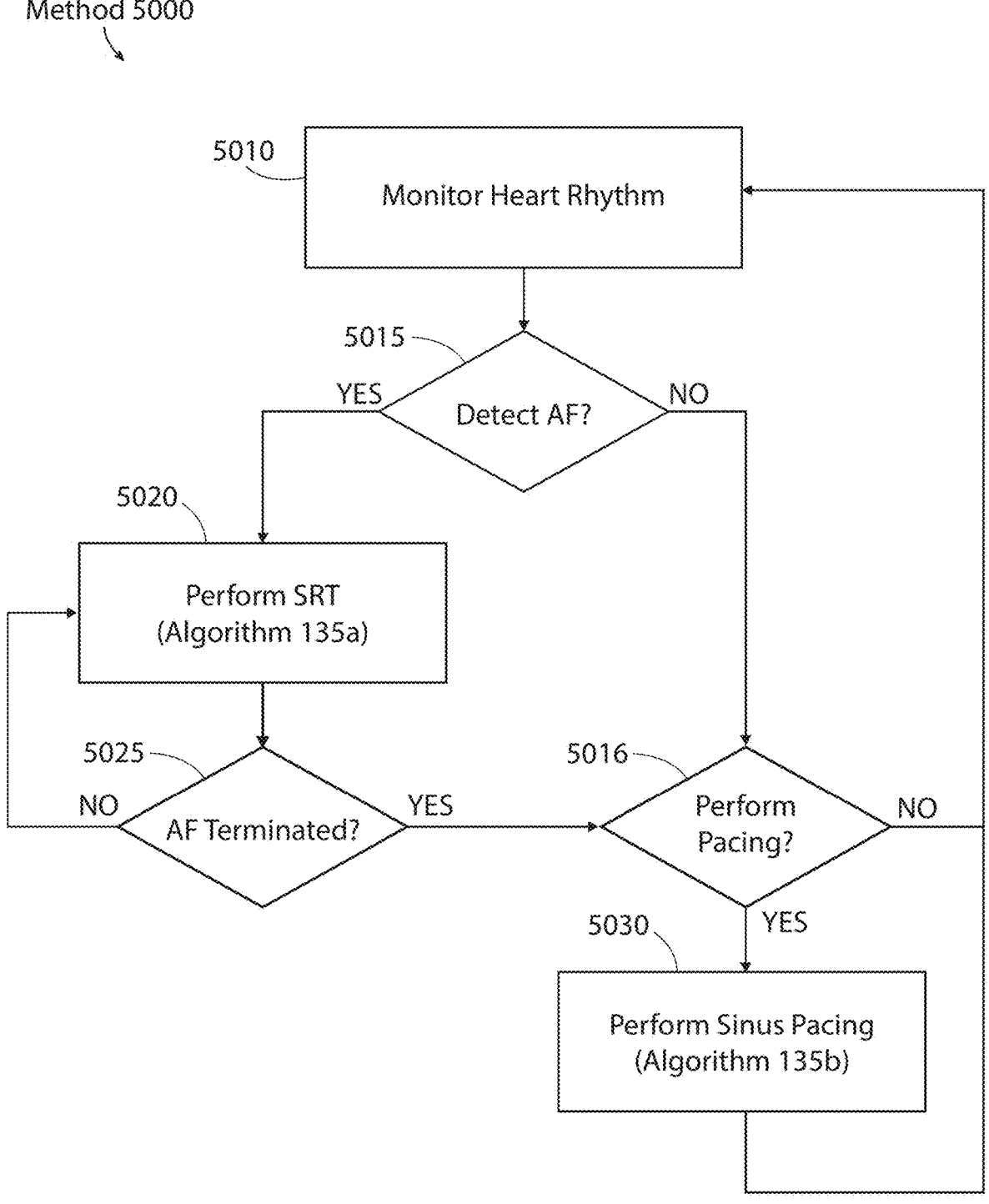
FIG. 10 illustrates a method of treating a patient with AF and limiting the likelihood of recurrence of AF, consistent with the present inventive concepts.

Referring now to FIG. 10, a method of treating a patient with AF and limiting the likelihood of recurrence of AF is illustrated, consistent with the present inventive concepts. Method 5000 of FIG. 10 can be executed using one or more of the devices or other components of system 10 described herein. In some embodiments, system 10 comprises a first algorithm, algorithm 135a, comprising instructions that cause implantable device 100 to deliver non-linear SRT pulses (e.g., to terminate AF). System 10 can further comprise a second algorithm, algorithm 135b, comprising instructions for implantable device 100 to deliver pacing energy to pace the heart during sinus rhythm (e.g., when AF is not present). In some embodiments, algorithm 135b is configured to pace the heart with a variable rate, such as to decrease the likelihood of initiation and/or re-initiation of an arrythmia. In some embodiments, implantable device 100 (e.g., ID 100 and one or more other components of system 10) can be configured to provide variable heart rate pacing, and/or pacing that is slightly faster (e.g., at least 5%, 10%, or 20% faster) than normal sinus rhythm (e.g., to reduce vulnerability of re-initiation of AF). In these embodiments, either or both of these pacing configurations can be combined with SRT pacing.

In some embodiments, for example as described herein in reference to FIG. 1A, system 10 can comprise a first implantable device, implantable device 100a, and a second implantable device, implantable device 100b. Implantable device 100a can include an implantable device positioned proximate the left atrium of the heart, for example when at least a portion of device 100a is positioned on the epicardial surface of the left atrium. Implantable device 100a can be configured to deliver stimulation energy as instructed by algorithm 135a (e.g., to terminate AF). Implantable device 100b can include an implantable device with at least a portion positioned away from the heart, for example at least a pulse-generation portion that is implanted in a subcutaneous pocket. Implantable device 100b can be configured to deliver stimulation energy as instructed by algorithm 135b (e.g., to pace the heart during sinus rhythm), such as via a lead implanted in the cardiac tissue (e.g., a lead including electrode 111b). In some embodiments, implantable device 100a comprises a rechargeable battery (e.g., a battery of power module 140, not shown but described in reference to FIG. 1 and otherwise herein), and implantable device 100b comprises a non-rechargeable battery (e.g., a battery of power module 140b). In some embodiments, system 10 comprises a single implantable device 100 configured to perform algorithms 135a and 135b, and to provide both SRT and pacing treatments. In some embodiments, implantable device 100 comprises two power supplies (e.g., two batteries), each supply configured to provide power for one of SRT stimulation or pacing stimulation (e.g., one supply for each), also as described herein.

Natural variability in heart rate reduces vulnerability of the cardiac substrate to initiation and/or re-initiation of arrhythmia. Bradycardia pacing has shown that increasing the pacing rate to 80-85 bpm, which is approximately 20% faster than a typical baseline rate of 70 bpm, reduces the incidence of AF episodes in patients diagnosed with AF. Additionally, pacing at such an increased rate can both reduce the incidence of AF, and can improve the quality-of-life in heart failure patients with preserved ejection fraction (HFpEF). In some embodiments, implantable device 100 (e.g., ID 100 and one or more other components of system 10) can be configured to perform bradycardia pacing, as well as heart rate variability pacing and SRT pacing.

Patients with a history of AF have substrates that are predisposed to the initiation and maintenance of AF. Currently, these patients are administered drugs (e.g., beta blockers or calcium channel blockers), and/or undergo ablative procedures, each as preventative measures. These options have proven to be less than adequate for reduction of AF burden and improvement in quality-of-life. Additionally, patients afflicted with both heart failure and AF have a particularly poor prognosis, as known AF preventative measures (e.g., medications that can interfere with their heart failure medical management) result in diminished effectiveness (e.g., a 5-year life expectancy for 50% of this patient population). In some embodiments, algorithm 135b is configured to cause ID 100 to deliver energy to minimize susceptibility to initiation of AF in patients with HFpEF.

In some embodiments, implantable device 100 (e.g., ID 100 and one or more other components of system 10) can be configured (e.g., via an algorithm of system 10 as described herein) to determine when to pace for prevention of an arrhythmia (e.g., AF) versus when to pace for termination of an arrhythmia, such as AF. System 10 can be configured to determine which type of pacing should be delivered, and when that pacing should be initiated. Method 5000 can be performed by one or more implantable devices 100, such as one or more devices that have been implanted as described herein, and configured to monitor for and/or to treat atrial fibrillation. In Step 5010, system 10 records and analyzes cardiac signals to detect the presence of AF. In Step 5015, if AF is detected, method 5000 continues to Step 5020. If AF is not detected, method 5000 continues to Step 5016.

In Step 5020, system 10 performs SRT pacing to treat the detected AF, restoring sinus rhythm (e.g., as described herein), such as via commands from algorithm 135a. In Step 5025, if AF has not been terminated, method 5000 returns to Step 5020, and SRT pacing continues. In some embodiments, Step 5020 includes performing method 2000 and/or method 3000, each as described herein. In Step 5025, if AF has been terminated, and sinus rhythm restored, method 5000 continues to Step 5016.

In Step 5016, system 10 determines if variable rate pacing should be performed. If irregular pacing is prescribed, method 5000 continues to Step 5030. Otherwise, method 5000 returns to Step 5010. In some embodiments, method 5000 performs Step 5030 continuously and/or semi-continuously, for example while performing Step 5010 to monitor for AF. Method 5000 can be configured to stop pacing performed in Step 5030 if AF is detected and to perform Step 5020. System 10 can be configured to determine (e.g., via an algorithm of system 10 as described herein) the patient's susceptibility to an arrhythmia (e.g., AF), and to further determine whether or not variable rate pacing should be delivered.

In Step 5030, implantable device 100 can deliver stimulation pulses, as instructed by algorithm 135b. For example, pacing can be delivered in which the baseline sinus rhythm is nonlinearly (deterministically) varied with "irregularly-early" pacing-pulses that impose a deterministic variation in heart rate. This pacing arrangement can be achieved by an algorithm of system 10 first deriving the mean and standard deviation (or median and IQR) of heart rate for a predetermined period. Based on these parameters, algorithm 135b can deliver stimuli according to a "fractal" and/or other appropriate nonlinear function that paces the heart at a time that is "earlier" than the mean cycle-length (inverse of heart rate) to deterministically impose a variation in heartbeat, as compared to the previous beat. Additionally or alternatively, subsequent heartbeats can be paced at differing durations of "earliness" to impose a desired variability in the heart rate over time. In some embodiments, algorithm 135b can include occasional inhibition of pacing to achieve the "intrinsically-longest" cycle-length, as a part of the overall range of variation that occurs over time.

In some embodiments, algorithm 135b can also include periodic cessation of pacing to re-assess the mean and standard deviation (or median and IQR) of heart rate. For example, algorithm 135b can follow the natural variation in heart rate and enhance the natural variation, or lack thereof, with "variably-early stimulation". The overall goal of such a pacing algorithm can be to achieve a level of variation that optimizes the probability of reducing vulnerability to initiation and/or re-initiation of arrhythmia.

In some embodiments, algorithm 135b can be configured such that the baseline sinus rhythm is paced at a rate that is faster than the intrinsic rate. This pacing arrangement can be achieved by first deriving the mean and standard deviation (or median and IQR) of heart rate for a predetermined period. For example, based on these parameters, stimuli can then be delivered at a rate that is 15%, or 20%, or 30% faster than the derived mean or median rate. Alternatively or additionally, stimuli can be delivered at a default rate of 85, or 75, or 90 bmp. In some embodiments, the higher pacing rates described above (e.g., as a percentage increase and/or a default rate) can be deterministically varied as a potential mechanism for minimizing vulnerability of the cardiac substrate to initiation and/or re-initiation of arrhythmia, including atrial fibrillation.

As described herein, system 10 can deliver, via a first algorithm, SRT configured to restore sinus rhythm, in combination with the delivery of energy, via a second algorithm that maintains normal heart rate variability to reduce vulnerability to recurrence of an arrhythmia (e.g., atrial fibrillation).

In some embodiments, implantable device 100 is implanted following an AF treatment procedure, such as an ablation procedure. During AF ablation procedures, AF is terminated into sinus rhythm during the delivery of ablation in approximately 35% of procedures. In approximately 10% of these 35%, the SA-node fails to automatically re-initiate a baseline ("normal") sinus rhythm. In such cases, the SA-node appears to have been electrically remodeled into a quiescent state that is presumably due to the rapid impingement of activation upon it during the ongoing AF. It has also been observed that such instances of cessation are temporary, with SA-node activation gradually "waking-up" and resuming the maintenance of baseline sinus rhythm. Such wake-up periods generally range from a few minutes to about 30 minutes. At this point in the procedure, the laboratory stimulator is applied to address the bradycardia and maintain a normal baseline heart rate, while the SA-node is recovering its ability to maintain sinus rhythm. This is performed by the laboratory support staff at the request of the physician, by pacing through existing catheter-electrodes that are already placed in the heart.

In some embodiments, in Step 5030, implantable device 100 can deliver stimulation pulses (e.g., as instructed by algorithm 135*b*) in which the baseline sinus rhythm is temporarily maintained at a "typically normal" rate. In some embodiments, this rate maintenance can be achieved by first deriving the mean heart rate over a short period (several beats). In accordance with a maximum threshold of cycle-length, stimulation can be delivered (including "immediately") in the "AAI" or AAI(R) pacing modes (Atrial sensing/Atrial pacing/Inhibited/Rate responsive).

In some embodiments, algorithm 135*b* can periodically inhibit pacing to re-assess the intrinsic heart rate and while pacing is inhibited determine if the SA-node has recovered; if recovery is determined, pacing can remain inhibited. Additionally or alternatively, algorithm 135*b* can include a variation in the pacing rate, (e.g., as described hereabove), with the goal of reducing the vulnerability of the cardiac substrate to initiation and/or re-initiation of arrhythmia.

In some embodiments, algorithm 135*b* can instruct (e.g., cause) the application of physiologic DDD or DDD(R) pacing modes (Dual sensing/Dual pacing/Demand/Rate responsive). Additionally or alternatively, algorithm 135*b* can instruct the application of physiologic VVI or VVI(R) pacing modes (Ventricular sensing/Ventricular pacing/Inhibited/Rate responsive). Physiologic pacing can include placing a pacing lead or leads (e.g., one or more leads including electrodes 111*b* of device 100*b*) in areas of the myocardium that promote a more synchronized contraction of the ventricles.

In some embodiments, system 10 can be configured to provide atrial pacing directly "in-line" with the SA-node, and such conduction characteristics may play a positive role in recovery of the SA-node. Ventricular pacing, on the other hand, directly addresses the undesired slow heart rate (bradycardia) without any consideration on the "health" of AV-node conduction.

In some embodiments, device 100 is configured to monitor cardiac signals to determine if the SA-node remains quiescent for a prolonged period. In some embodiments, system 10 can be configured to notify the patient's physician (e.g., system 10 can send an alert to clinician device 300 via network 50, each described in reference to FIG. 1 and otherwise herein). For example, system 10 can send an alert to clinician device 300 when system 10 transitions into an alert or other pre-determined state (e.g., undesired state) of system 10. In some embodiments, system 10 can be configured to determine (e.g., via algorithm 135) if the patient requires another type of therapy (e.g., a pacemaker), for example therapy to treat bradycardia caused by a "sick sinus node". In some embodiments, an implantable device of system 10, for example implantable device 100*b*, can be configured to operate as a pacemaker. Alternatively or additionally, system 10 can include an additional implantable device 100 configured as a pacemaker (e.g., an additional device configured to operate in conjunction with implantable device 100 that is configured to provide SRT pacing to treat AF). In some embodiments, system 10 (e.g., implantable device 100) is configured to terminate AF, prevent AF, and treat prolonged bradycardia, as described herein.

Figure 11:
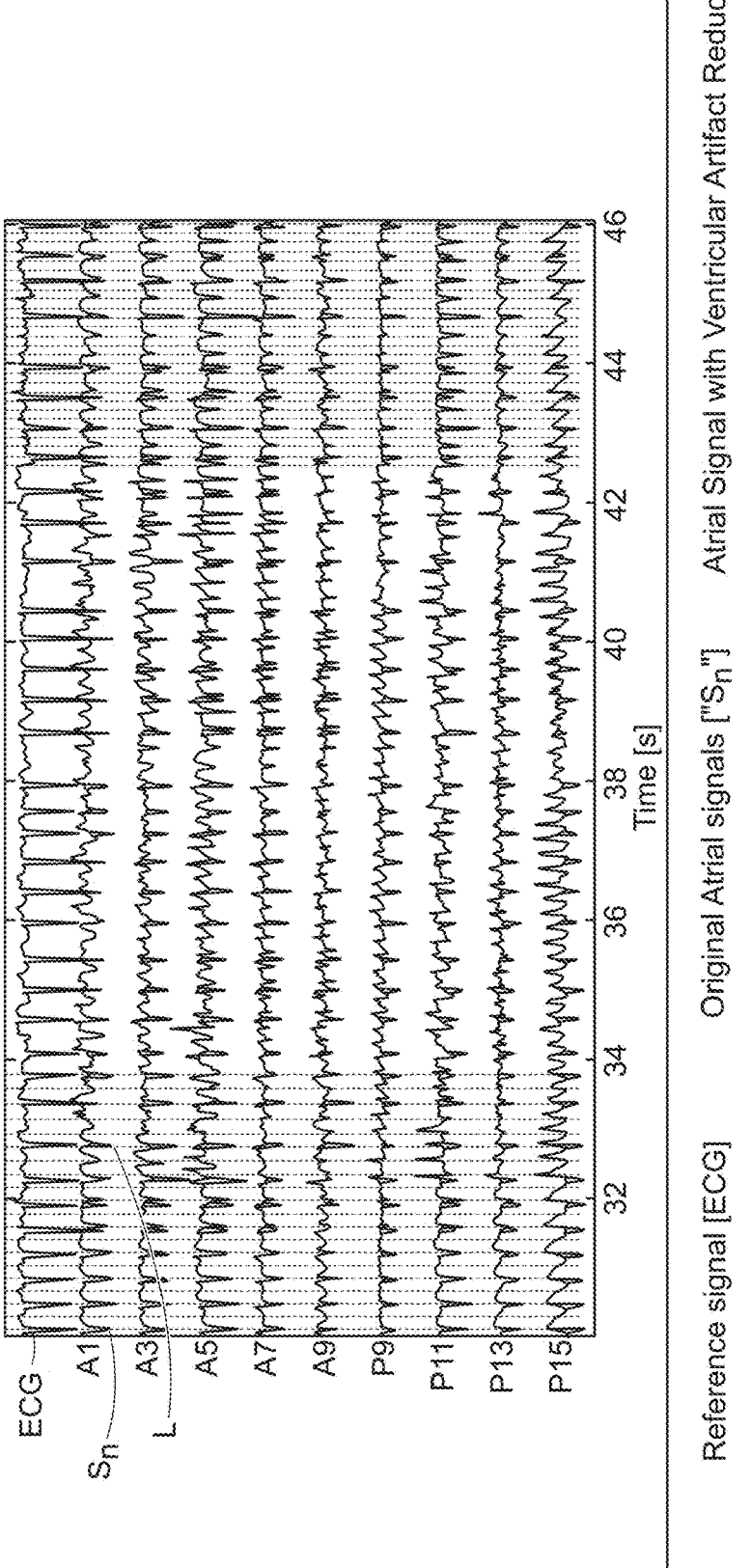
FIG. 11 illustrates a graph of recorded cardiac signal with reduced ventricular artifacts, consistent with the present inventive concepts.

Referring now to FIG. 11, a graph of recorded cardiac signals with reduced ventricular artifacts is illustrated, consistent with the present inventive concepts. Algorithms 5100 and 5110 of FIG. 11 can be performed by system 10 described in reference to FIG. 1 and otherwise herein. System 10 can include algorithm 5100 that includes Ventricular Artifact Suppression algorithm 5110, for example as described in reference to FIG. 2A and otherwise herein. In some embodiments, measured atrial signals (e.g., atrial signals recorded via one or more electrodes of system 10 as described herein) are defined as $S_n = A_n + V^*$, where "$A_n$" is the atrial component of "$S_n$" and "$V^*$" is the far-field ventricular contribution. A reference signal, "E" (e.g., a signal recorded via an ECG Lead or ventricular EGM), that contains "$V^*$" contributions that are well correlated with the atrial signals can be used to reduce the ventricular artifact of signals $S_n$. In some embodiments, the reference signal contains minimal atrial content "A" and maximal ventricular deflections "$V^*$". The "$V^*$" components can be extracted from the reference signal and subtracted from the atrial signals by calculating an optimal least-squares ($l_2$) scaling factor, a, that satisfies the following equation:

$$\min_{\alpha} \| (A_n + V^*) - \alpha E_n \|_2$$

For every channel n (e.g., for each signal recorded from each recording electrode), the atrial signal with reduced ventricular artifact can be computed by algorithm 5110 as $L_n = S_n - \alpha E_n$ which approximates "An" provided that $V^* \sim E_n$.

An additional method to remove the far-field $V^*$ from the $S_n$ signals is to blank the regions where there is a significant ventricular far-field deflection. For example, in some embodiments, algorithm 5110 first finds the peaks of the QRS complexes of the "E" signal and indexes the times when they occur. Algorithm 5110 can then blank $S_n$ in the regions by linearly interpolating the gaps between the indexed instances. The resultant signal, $B_n$, is analogous to the $L_n$ signal: $B_n \approx L_n \approx A_n$. In some embodiments, algorithm 5110 combines the more aggressive "$V^*$" elimination of the blanking method with the signal reconstruction of the least-squares method. The combination is performed by a weighted mean. The weight coefficient, "$C_n$", is computed for every channel:

$$C_n = \frac{\sum_{all\ elements} |L_n|}{\sum_{all\ elements} |S_n|}$$

The value of "$C_n$" lies between 0 and 1. If $C_n > 0.25$, the least-squares fit, "$L_n$", can be declared to be insufficient. In this case, the signal can be improved by computing a weighted average of the least-squares fit $L_n$ and the blanked signal "$B_n$" as represented in the equation $$A_n = (1 - C_n) L_n + C_n B_n.$$

Referring now to FIGS. 12A-F, various graphs and plots relating to data analyzed using a hyperplane algorithm are illustrated, consistent with the present inventive concepts. Algorithms 5100 and 5120 of FIGS. 12A-F can be performed by system 10 described in reference to FIG. 1 and otherwise herein. For example, system 10 can include algorithm 5100 that includes Hyperplane algorithm 5120, such as is described in reference to FIG. 2A and otherwise herein. In some embodiments, hyperplane algorithm 5120 performs a method of processing recorded signals to reduce a multidimensional dataset down to two dimensions that preserve the dynamical, morphological, and spectral information as the original dataset.

Hyperplane algorithm 5120 requires "n" continuous and non-divergent signals. For example, cardiac signals from any anatomical region (e.g., bipolar and/or unipolar signals) meet this requirement. All signals must be sampled across the same window of time with the same sample rate. In some embodiments, there is no strict requirement for the sampling rate. If the original signals contain one or more features of interest, hyperplane algorithm 5120 can generate an optimized two-dimensional projection of the signals which will preserve these features.

In some embodiments, the method creates a best fit plane through the spatial distribution of "n" dimensions. First, algorithm 5120 can arrange all the signal time series in a matrix "X" such that each row of the matrix corresponds to each of the "n" signals. The columns of the matrix can represent the state at multiple time steps X=[x1, x2, . . . , xm], where "x" is a column vector state at discretized time. Next, algorithm 5120 can extract the third eigenvector of the covariance matrix XX*, where X* is the complex conjugate of X. The left eigenvectors point in the directions of maximal data variance and minimize the square of the distance to each state vector under the Euler norm. In some embodiments, the eigenvectors can be calculated using the Singular Value Decomposition (SVD) of X. The SVD produces the decomposition matrix of X=U$\Sigma$V* (where the U matrix contains the eigenvectors of XX*). The orthogonal eigenvectors in U and V are hierarchically ordered by their scaled eigenvalues. The first two eigenvectors u1 and u2, in U (the first two columns) optimally span the n-dimensional dynamics of the signals through time. The optimal projected plane is constructed by the equation u1×u2=u3, where u3 is the third eigenvector and x is the cross product. Each state x1, x2, . . . , xm is thereby projected onto the optimal plane.

Alternately, if the signals are stacked as columns (e.g., if the state vectors are rows), another projection can be achieved by algorithm 5120 using the transpose of X. In this case, the right eigenvectors are used from the columns of the V matrix. The u3 vector is orthonormal to the plane spanned by u1 and u2. For this reason, it is renamed as:

$$\hat{n} = u_3$$

Provided a state vector x, the projected state onto the hyperplane is:

$$x_p = x - \frac{(x^T \hat{n})\hat{n}}{\sum_i \hat{n}_i}$$

where the sum is for all vector elements. Afterwards, $x_p$ can be rotated by algorithm 5120 to the 2D plane spanned by [1,0,0, . . . , n] and [0,1,0, . . . , n] with a rotation matrix defined as:

$$R = W^{-1} U = IU$$

where $W^{-1}$ is the inverse matrix of the cartesian basis, which in this case is equal to the identity matrix I Finally, Applying the rotation reads:

$$p_{xy} = Rx_p$$

By applying this algorithm for each electric state, algorithm 5120 can generate the projected Hyperplane signals $p_{xy}$.

When all "m" state-vectors "x" are projected onto the optimal hyperplane, the original signal dynamics are preserved within the projected plane.

In some embodiments, such as when there are very few signals (e.g., only one measured signal is available), the matrix X can be constructed by applying the principles of Takens "delay embedding". A new set of signals can be constructed by resampling the original signal with a delay and coherently arranging the signal in the second row of matrix X. Additional signals can be constructed by repeating this procedure with integer multiples of the chosen time delay. Algorithm 5120 can repeat this process "n" times to complete constructing the matrix X. Algorithm 5120 can trim the left and right ends of the matrix to achieve equal-length continuity of the signals throughout the matrix.

Figure 12A:
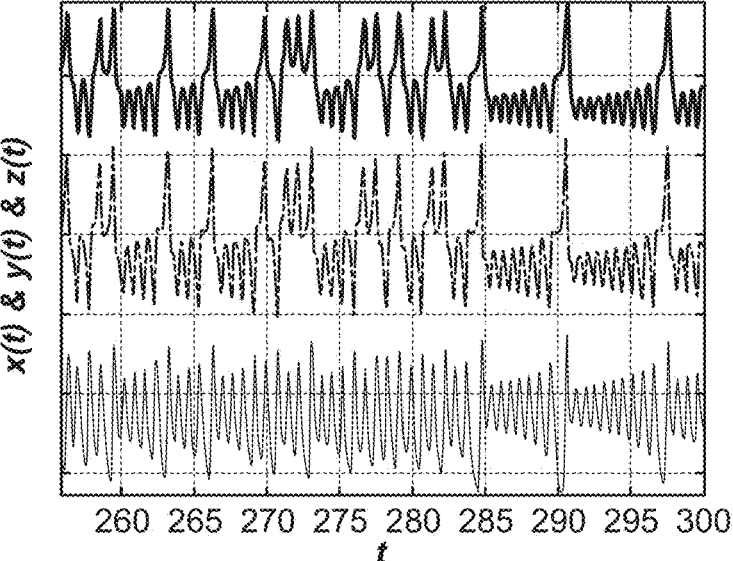
Figure 12B:
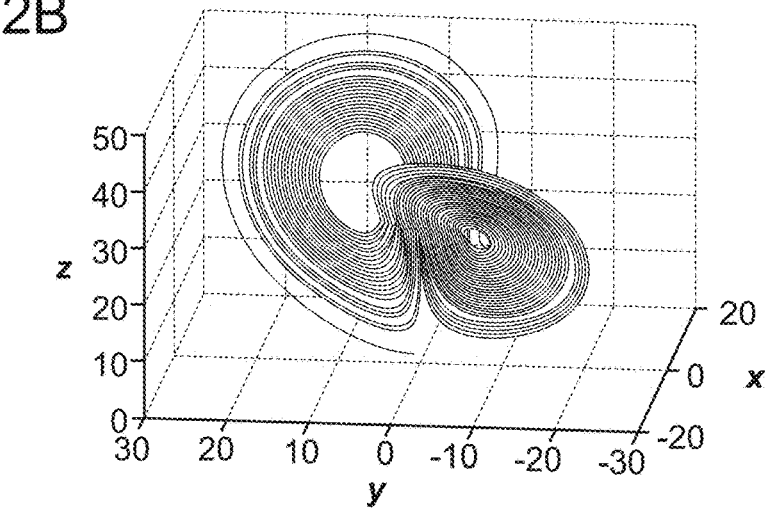
Figure 12C:
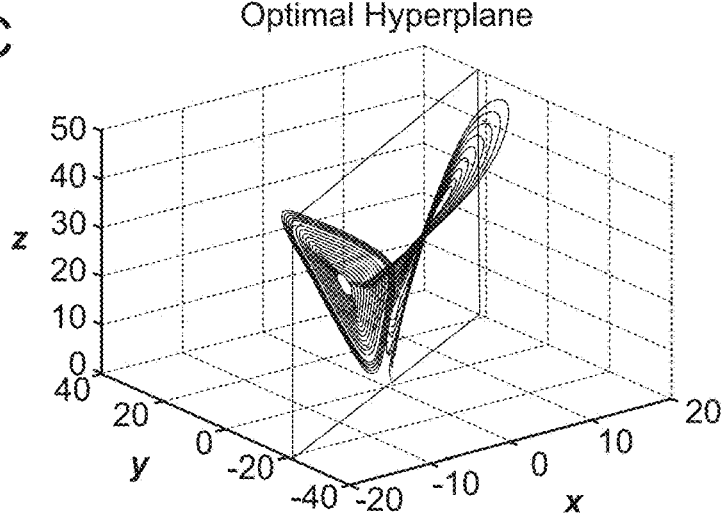
Figures 14A, 14B, 14C, 14D, 14E, 14F:
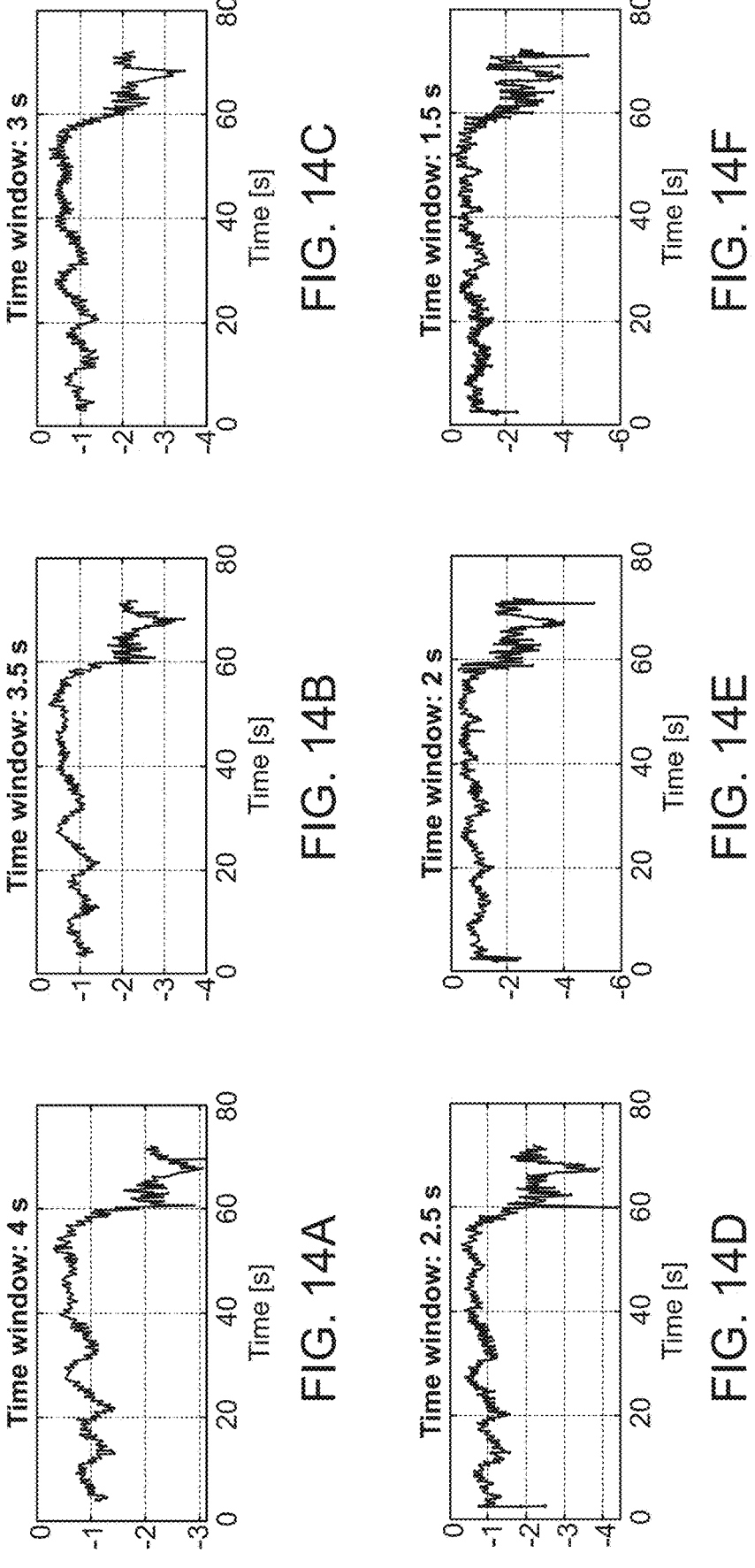
FIGS. 14A-F illustrate various graphs of recorded data and processed data, consistent with the present inventive concepts.

FIGS. 12A-F illustrate an example of three signals of a chaotic system that are projected onto a hyperplane. FIG. 12A shows three time-series from a chaotic system. By plotting the value of each signal as a three-dimensional point for each instant of time, a complex yet bounded structure called an "attractor" can be generated, as shown in FIG. 12B. An optimal hyperplane can be fitted to the attractor by algorithm 5120, which reduces three dimensions to two, for example as shown in FIG. 12C. A two-dimensional structure can be extracted from a projection onto a plane that contains the same dynamical, morphological, and spectral information as the higher dimensional attractor, as shown in FIG. 12D. The coordinates can be renamed u and v. The two components of the projected time series form an analogous time series, as shown in FIG. 12E. FIG. 12F shows a real example from four channels of atrial, unipolar signals that contain atrial fibrillation and sinus rhythm projected onto a hyperplane.

Referring now to FIGS. 13A-C, various graphs of recorded data and processed data are illustrated, consistent with the present inventive concepts. Algorithms 5100 and 5133 of FIGS. 13A-C can be performed by system 10 described in reference to FIG. 1 and otherwise herein. For example, system 10 can include algorithm 5100 that includes rhythm detection algorithm 5130, such as is described in reference to FIG. 2A and otherwise herein. Rhythm detection algorithm 5130 can include sync index algorithm 5133. In some embodiments, sync index algorithm 5133 comprises performing sync index algorithm 5132, but instead of applying the Hyperplane projection and selecting a projected window signal, a single channel can be selected and the algorithm can be performed. The result is the cycle length for that channel. In a first step, algorithm 5133 can create a kernel $g(t)=\cos(2\pi t/CL^*)$, where $CL^*$ is the dominant CL that was previously computed. Algorithm 5133 can then compute the convolution integral of g and C2, h, where C2 is a convolution from sync index algorithm 5132. Algorithm 5133 can then compute the Hilbert transform H of h. Algorithm 5133 can then compute the phase of the $-h$ and the imaginary part of the previously computed Hilbert transform as $\varphi=\text{atan } 2(-h, \text{Im}(H))$. In some embodiments, these steps are repeated for each channel. Once all the phases $\varphi\_j$, $j=1,2,\ldots,N$, where N is the number of channels, are computed, algorithm 5133 can compute the magnitude of the phase contribution vector as $|z|=|1/N^*\Sigma e^{\wedge}(i\varphi\_j)|$, where the sum is over all N channels and i is the imaginary unit and z is a complex number (e.g., based on the Kuramoto theory). Notice $z\in[0,1]$.

In theory, for a short enough window, z should be a constant for a synchronized system (e.g., the change in phase is constant or zero over time). In practice, z will fluctuate locally for regular rhythm, while with atrial fibrillation it will fluctuate through all of the domain. This observation leads to conclude that on average, for AF, the integral $I=\int|z|dt$ over the time window is less than or equal than ½. In the case of regular rhythm, it has been observed that a constant phase channel differences of the atrial depolarizations never surpasses $\pi$ radians, therefore $|z|$ will mildly oscillate with a mean value of ½ or greater. As a result, $I\in[0,a]$, where a is a positive number. In practice $I\in[0,½]$, where high values correspond to regular rhythm and lower values correspond to chaotic states. Algorithm 5133 can rescale I as $I\_s=2I-1$, so that $Is\in[0,1]$. In addition, the threshold value that separates AF from regular rhythms can be set to ½ so that a chaotic state corresponds to $I\_s$ less than ½ and a regular rhythm state to $I\_s$ greater than ½.

FIG. 13A shows an example of a 3 second time window of a hyperplane-projected unipolar signal, and the reconstructed phase of the signal as determined by sync index algorithm 5133. FIG. 13B shows the vector $|z|$ in time. The average value of the oscillations shown in FIG. 13B are greater than ½, suggesting that the expected area under the curve is larger than ½. In FIG. 13C the oscillations are more erratic, reducing the area under the curve to less than 2.

Referring now to FIGS. 14A-F, various graphs of recorded data and processed data are illustrated, consistent with the present inventive concepts. Algorithms 5100 and 5134 of FIGS. 14A-F can be performed by system 10 described in reference to FIG. 1 and otherwise herein. For example, system 10 can include algorithm 5100 that includes rhythm detection algorithm 5130, such as is described in reference to FIG. 2A and otherwise herein. Rhythm detection algorithm 5130 can include another embodiment of a sync algorithm, sync index algorithm 5134. In some embodiments, the first step of algorithm 5134 is to calculate the dominant cycle length of a signal, for example using cycle length algorithm 5142 described herein. A time window of one of the two channels from the Hyperplane projection can then be selected. Sync index algorithm 5134 can then apply a data processing algorithm that calculates the largest Lyapunov exponent, such as, for example, the algorithm titled "Mirwais (2023) Largest Lyapunov Exponent (LLE) with Rosenstein's Algorithm" (an embodiment of which was retrieved by the applicant on Jun. 23, 2023, from the MATLAB Central file exchange, https://www.mathworks.com/matlabcentral/fileexchange/38424-largest-lyapunov-exponent-with-rosenstein-s-algorithm), or an equivalent thereof, "Mirwais algorithm" herein. The following parameters are inputs for the Mirwais algorithm: the Takens embedded dimension, the Takens time delay, and the mean period round(CL*/Ts), where Ts is the sampling time. In some embodiments, the embedded dimension D=3 and the time lag $\tau$ is 10 samples (e.g., 5 ms). In some embodiments, one or more of the sections of the Mirwais algorithm can be vectorized. Additionally or alternatively, the Mirwais algorithm can be optimized by vectorizing one or more sections, changing FOR loops to WHILE loops, and/or subsampling at key sections. The algorithm can also be modified to stop the largest Lyapunov exponent convergence such that the LLE time series stops being monotonically increasing. The optimization of the Mirwais algorithm described herein preserves the quality of the results while improving the computational speed from seven times to fifteen times faster than the non-optimized Mirwais algorithm, depending on the data window size (e.g., the larger the window the greater the speed improvement). By an empirical analysis, LLE values above $-3.8$ are considered chaotic (fibrillatory), values lower than $-4.25$ are considered regular rhythm, and values in between are considered as flutter. These values comprise patient specific averages. FIGS. 14A-F show the LLE time series for various window sizes with an 0.1 sec overlap. The larger the LLE value, the more chaotic the signal is. In the case shown, the signals present a state transition from AF to Sinus rhythm at t=57 sec. This transition is well captured for all window sizes. FIGS. 14A-F demonstrate the low sensitivity of the method to the window size.

Figures 15A, 15B, 15C:
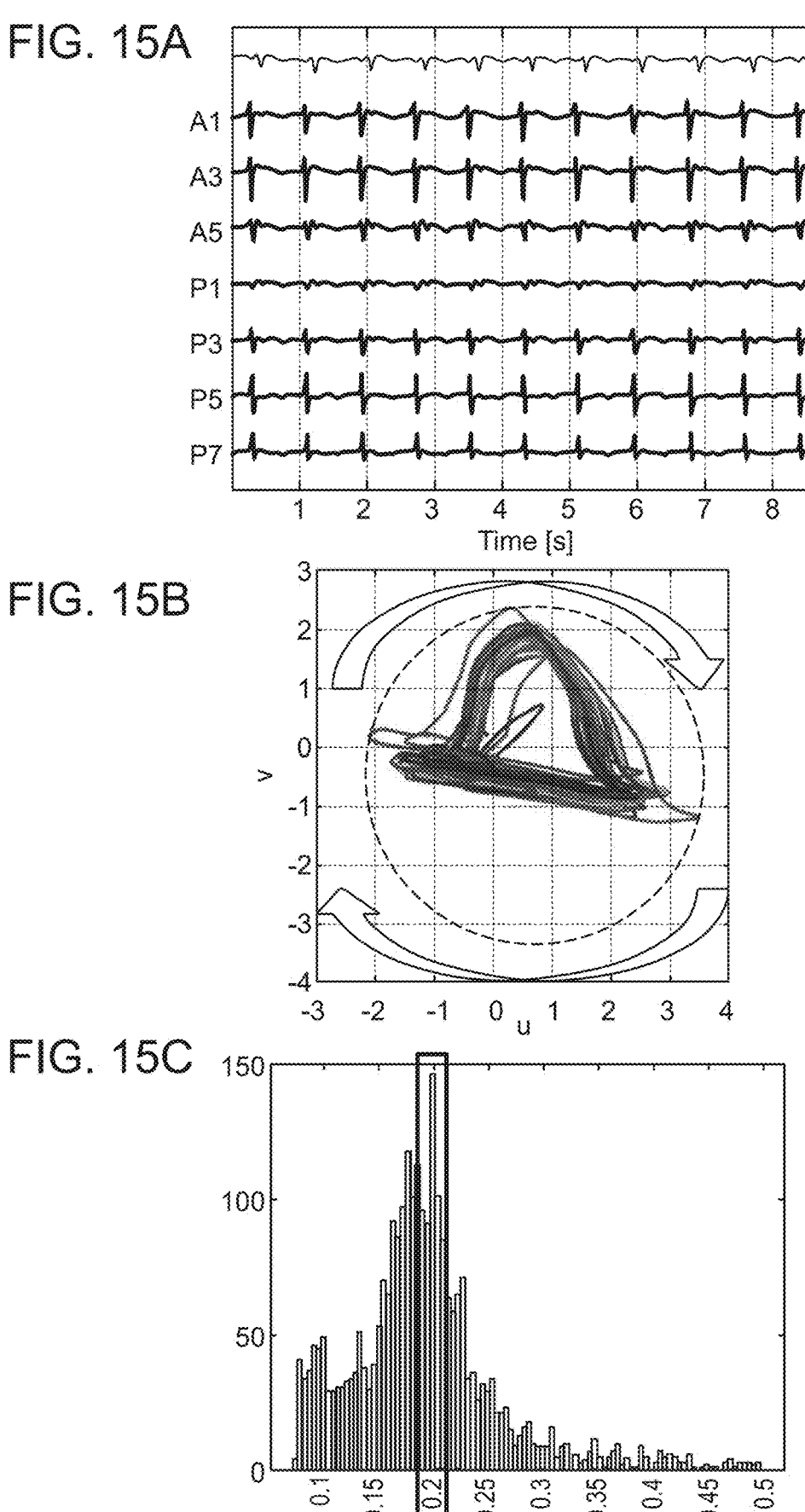
FIGS. 15A-C illustrate various graphs of recorded data and processed data, consistent with the present inventive concepts.

Referring now to FIGS. 15A-C, various graphs of recorded data and processed data are illustrated, consistent with the present inventive concepts. Algorithms 5100 and 5140 of FIGS. 15A-C can be performed by system 10 described in reference to FIG. 1 and otherwise herein. For example, system 10 can include algorithm 5100 that includes dominant cycle length algorithm 5140, such as is described in reference to FIG. 2A and otherwise herein. Dominant cycle length algorithm 5140 can include a cycle length algorithm, cycle length algorithm 5141. In some embodiments, the first step to quantify the level of chaos of a set of cardiac signals is to apply hyperplane algorithm 5120, such as is described herein. Cycle length algorithm 5141 can then define an axis for the projected set of signals (e.g., the signals projected by algorithm 5120) with coordinates [u, v]. The axis should bisect the projected attractor (PA) with an equal distribution of data about the axis. In some embodiments, algorithm 5141 creates the axis by determining the optimal circle that encloses the PA, such as by using the algorithm published by John D'Errico (2023). Algorithm 5141 can determine the center of the PA using a suite of minimal bounding objects, such as a suite from MATLAB Central File Exchange. Algorithm 5141 can translate the origin of all the coordinates to the center of the PA. Algorithm 5141 can rotate the PA in such a way that the sections corresponding to baseline values are aligned on the positive u axis (horizontal axis). This can be performed by calculating the average value of u and v, which is called $p=[u0,v0]$. Algorithm 5141 can then compute the angle $\varphi$ of p with respect to the u axis. Algorithm 5141 can then perform a two-dimensional rotation of PA by $-\varphi$. This results in the signal baseline being aligned on the positive u axis. The translation and rotation of the PA improves the accuracy of rhythm detection because the critical features of the signals are repositioned and constrained about the negative u axis and the positive and negative v (vertical) axis. The position of the PA can be incrementally rotated by an amount $\theta$, resulting in a new set of points that are repositioned around the positive u axis, or equivalently, in the region around v=0. Algorithm 5141 can determine the time at which the [u, v] trajectory crosses the positive u axis and record the u and v values each time the signal trajectory crosses the u or v axis. These recorded values can be numbered as t1, t2, . . . , tq. Once all the crossing times are collected, algorithm 5141 can take the differences between them (e.g., t2–t1, t3–t2, . . . , tq–tq–1) and store the data. Algorithm 5141 can repeat this procedure over a range of 0 angles. With the data differences for all the angles, algorithm 5141 can compute a histogram and select its mode as the dominant cycle length.

FIG. 15A shows a graph of atrial signals of the anterior and posterior regions of the heart (e.g., signals recorded via electrodes 111 of system 10, described herein). FIG. 15B shows the PA of atrial signals after projected to a hyperplane by algorithm 5120. The different signals correspond to the time progression. The dotted circle is the fitted geometric circle and the arrows represent the process of rotating the PA multiple times to compute a set of Δt's. FIG. 15C shows a histogram of Δt's and the dominant cycle length (e.g., the mode) is highlighted in the rectangle.

Referring now to FIGS. 16A-D, various graphs of recorded data and processed data are illustrated, consistent with the present inventive concepts. Algorithms 5100 and 5140 of FIGS. 16A-D can be performed by system 10 described in reference to FIG. 1 and otherwise herein. For example, system 10 can include algorithm 5100 that includes dominant cycle length algorithm 5140, such as is described in reference to FIG. 2A and otherwise herein. Dominant cycle length algorithm 5140 can include another embodiment of a cycle length algorithm, cycle length algorithm 5142. In some embodiments, algorithm 5142 applies hyperplane algorithm 5120 to a windowed set of recorded cardiac signals. One of the two channels can then be selected (e.g., automatically by algorithm 5100 and/or by the user), the selected channel referred to herein as "u". Algorithm 5142 can select a wavelet, ψ, that resembles the R-S deflections of the derivative of unipolar signals referred to as a Symlet wavelet of order M, for example as shown in FIG. 16A. In FIG. 16A, a unipolar anterior AF signal is shown, as well as a single channel of the hyperplane projection of the anterior region, and the Symlet wavelet. The Symlet wavelet can comprise a compactly supported wavelet with the least amount of asymmetry and highest number of vanishing moments (M) for a given support width. The value chosen for M can be 4 for a 1 k-2 k sample rate. Algorithm 5142 can perform a convolution, $C_1$, of u with ψ, for example as shown by the resultant data illustrated in in FIG. 16B. In some embodiments, algorithm 5142 blanks a period, such as 20 ms, at each end of the sampling window to eliminate boundary effects, for example as shown by the resultant data illustrated in FIG. 16C. Algorithm 5142 can then compute $|C_1|^2$ and blank any residual noise (e.g., small amplitude oscillations), for example as shown by the resultant data illustrated in FIG. 16D. Algorithm 5142 can apply a second convolution $C_2$ of $|C_1|^2$ and a positive bell-shaped kernel with a maximum value of 1. The result of this second convolution is referred to as "$C_3$". Algorithm 5142 can compute the differences of the timing of the maxima (peaks) of $C_2$ to estimate the dominant cycle length. If the number of peaks is too low for any statistical significance, algorithm 5142 can use the maxima of the differences as the dominant cycle length. Otherwise, algorithm 5142 can use the mean of the differences as the dominant cycle length. To compute the cycle length of a single channel, instead of computing the Hyperplane projection, algorithm 5142 can be performed on the channel of interest by first selecting the wavelet, ψ, as described herein.

Figure 17A:
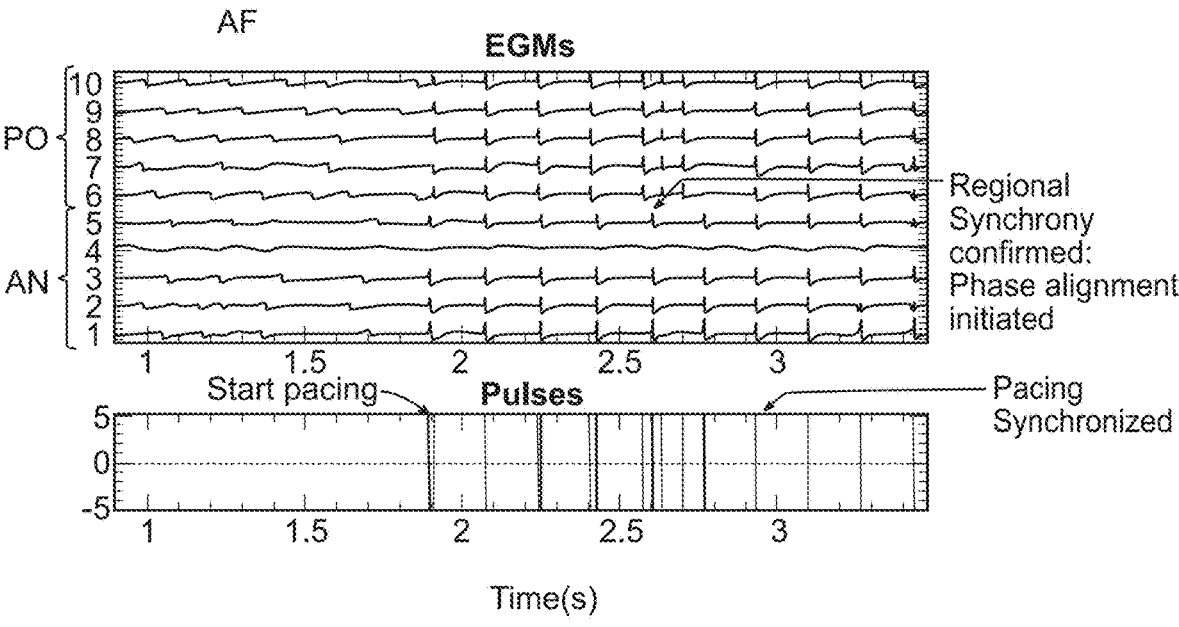
FIGS. 17A-B illustrate various graphs of recorded data and processed data, consistent with the present inventive concepts.
Figure 17B:
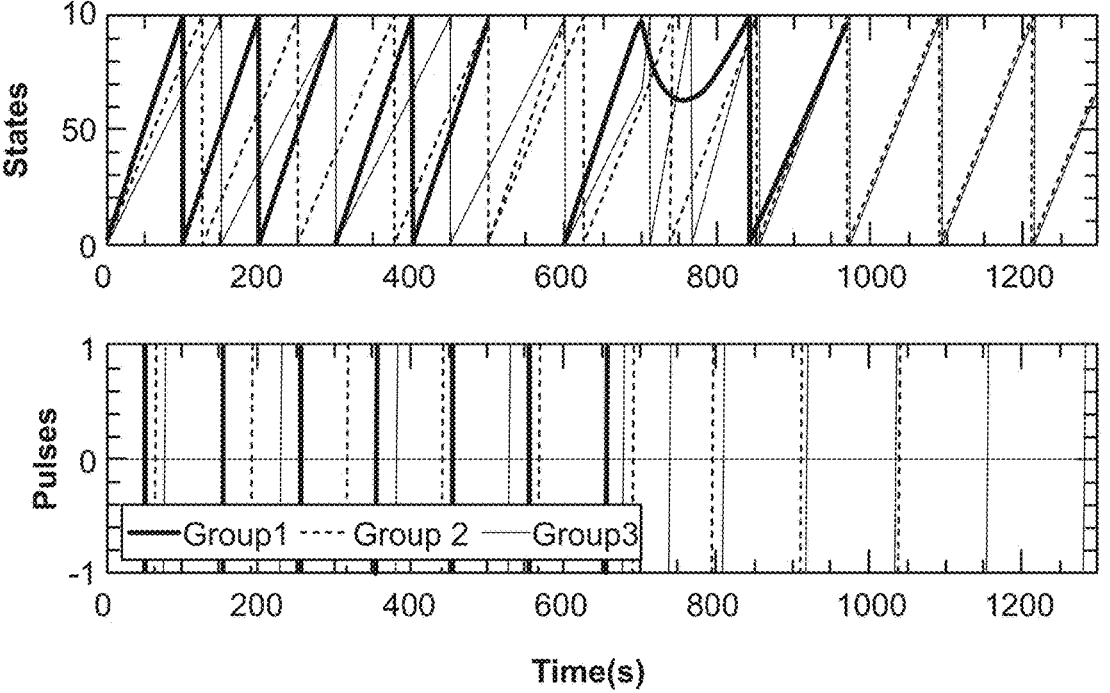

Referring now to FIGS. 17A-B, various graphs of recorded data and processed data are illustrated, consistent with the present inventive concepts. Algorithms 5100 and 5160 of FIGS. 17A-B can be performed by system 10 described in reference to FIG. 1 and otherwise herein. For example, system 10 can include algorithm 5100 that includes adaptation algorithm 5160, such as is described in reference to FIG. 2A and otherwise herein. Independent control of various atria regions characterized by their local dominant cycle lengths can necessitate a phase alignment algorithm, such as phase alignment algorithm 5162 of adaptation algorithm 5160. Phase alignment algorithm 5162 can become active when regional synchrony is confirmed (e.g., confirmed by substrate response algorithm 5161 described herein). Pacing at different rates can cause each controlled region to have a different phase, for example as shown in FIG. 17A. FIG. 17A shows an example for two controlled regions (e.g., anterior and posterior). In this example, AF is detected with dominant cycle length of 177 ms and 163 ms on anterior and posterior regions, respectively. Pacing is initiated at about 1.9 s, but since the cycle lengths are different, the pacing pulses do not align. At 2.6 s, rhythm detection algorithm 5130 confirms regional synchronization, and phase alignment algorithm 5162 is used which progressively synchronizes the pulses (300 ms later). Phase alignment algorithm 5162 can take advantage of the synchronization properties of coupled oscillators. For example, coupled heterogeneous oscillators will asymptotically synchronize if the coupling strength is greater than the critical value. By choosing the appropriate coupling strength, synchronization can be achieved and the rate of convergence can be controlled by algorithm 5162. The states of the oscillators can be used to control (e.g., trigger) the pulse generator. As an example, three groups of electrodes can be assumed that can be paced at 100 ms, 125 ms, and 150 ms, respectively. Each uncoupled oscillator can be set to oscillate with its respective cycle length, and every time the state crosses a threshold, for example a threshold of 50 as shown in FIG. 17B, the stimulator module (e.g., controller 130 of ID 100 described herein) can be triggered to generate a biphasic pulse of appropriate amplitude and pulse width, for example as determined by one or more user settings. When AF is detected and SRT is initiated, these oscillators can independently trigger pulses that, as shown in FIG. 17B, are not synchronized until regional synchronization is detected which then triggers the coupling of the oscillators to initiate synchronization.

Referring now to FIGS. 18A-C, various graphs of recorded data and processed data are illustrated, consistent with the present inventive concepts. Algorithms 5100 and 5150 of FIGS. 18A-C can be performed by system 10 described in reference to FIG. 1 and otherwise herein. For example, system 10 can include algorithm 5100 that includes control algorithm 5150, such as is described in reference to FIG. 2A and otherwise herein. In some embodiments, control algorithm 5150 includes capture assessment algorithm 5151. Algorithm 5151 can comprise a fast, accurate, automated multi-waveform capture detection algorithm configured to annotate capture of cardiac tissue during atrial arrhythmias. Capture assessment algorithm 5151 can process signals recorded from multiple spatially distributed electrodes. In some embodiments, the recording may be disturbed by far-field ventricular signals. Algorithm 5151 can be designed to reject such spurious patterns. As shown in FIG. 18A, a ventricular perturbation is indicated in the recorded unipolar signal. In some embodiments, capture is confirmed (e.g., by algorithm 5151) by nearby epochs. The number of Q-S morphology events surrounding a candidate can determine the final assessment of algorithm 5151. For example, an isolated captured candidate can be automatically demoted to "non-captured". FIG. 18B shows an example of capture classification performed by capture assessment algorithm 5151 during AF with unipolar recording and biphasic pacing. The raw AF signal is shown above with the corresponding capture classification below.

In testing performed by the applicant, capture assessment algorithm 5151 capture accuracy was evaluated by comparing to human-adjudicated annotation of capture (e.g., the Control) in 26 records. The robustness of algorithm 5151 was evaluated comparing baseline (0 noise) against five levels (1 to 5×) of the extracted 50 Hz noise re-imposed on the signals. Accuracy of algorithm 5151 at baseline relative to Control was 85%±8.8% [(TP+TN)/(TP+TN+FP+FN)]. The worst case error between algorithm 5151 and Control with respect to all levels of re-imposed 50 Hz noise was <6%. Relative error of the baseline of algorithm 5151 when compared to 1× level of re-imposed 50 Hz noise was 12.3%. The signal-to-noise ratio decreased arithmetically, and the relative error increased linearly. FIG. 18C shows a sensitivity-specific curve illustrating the performance of algorithm 5151 in the testing performed by the applicant. In some embodiments, the speed of algorithm 5151 is optimized to perform up to ten times faster compared to real-time processing, where real time processing comprises one second of processing time for one second of recorded data.

Referring now to FIGS. 19A-E, various perspective views of a portion of an implantable device are illustrated, consistent with the present inventive concepts. ID 100 of FIGS. 19A-E can be of similar construction and arrangement to the similar components described in reference to FIG. 1 and otherwise herein. In some embodiments, ID 100 comprises controller 130 that is configured to be implanted in a first location, for example a location away from the heart, and electrode array 110 that is configured to be implanted on the epicardial surface of the heart. Electrode array 110 can be operably coupled to controller 130 via one or more wires, such as via lead 1121 shown in FIG. 19A. Lead 1121 can electrically couple electrodes 111 of electrode array 110 to controller 130. ID 100 can comprise a housing, such as housing 101 shown, surrounding controller 130 and other components of ID 100 located apart from electrode array 110 (e.g., transceiver 120 and power module 140). In some embodiments, lead 1121 is configured to be tunneled through the tissue between electrode array 110 and housing 101. Housing 101 can be implanted in a subcutaneous pocket, such as a pocket located on the left side of the chest as shown. Electrode array 110 can comprise an expandable array configured to be positioned on the epicardial surface of the heart, such as between the epicardial wall of the left atrium and the pericardial sac. In some embodiments, lead 1121 is positioned through the percardial sac. FIG. 19B shows electrode array 110 positioned on the oblique sinus, between the pericardial reflections of the pericardial sac. Electrode array 110 can be configured to expand from a first geometry, shown in FIG. 19D, to a second, expanded geometry, as shown in FIG. 19E. In the expanded geometry, electrode array 110 can oppose the pericardial reflections, removably securing electrode array 110 to the heart. In some embodiments, the expanded geometry of electrode array 110 is adjustable, such as to conform to a variety of oblique sinus dimensions and contours. In some embodiments, electrode array 110 is configured to be repositioned, such as by at least partially collapsing the array, repositioning, and reexpanding the array.

Electrode array 110 can include a central shaft, shaft 1101, positioned at the distal end of lead 1121. Array 110 can include one or more expandable arms, arms 1102 shown, that are fixedly attached to a portion (e.g., the distal end) of shaft 1101, as show. The opposite ends of arms 1102 can be attached to a movable element, collar 1103, that slidingly translates on shaft 1101. Collar 1103 can be advanced along shaft 1101 to expand array 110, and/or retracted to compact array 110, for example as shown in FIGS. 19E and 19D, respectively. In some embodiments, electrode array 110 can comprise a locking mechanism, lock 1104, configured to lock collar 1103 in the forward position, locking array 110 in the expanded geometry. In some embodiments, clinician device 300, not shown but described herein, comprises a sheath through which electrode array 110 can be deployed. In some embodiments, clinician device 300 is configured to interact with lock 1104, for example to rotate a portion of collar 1103 and/or lock 1104 to lock and/or unlock array 110. In some embodiments, electrodes 111 are distributed about arms 1102 and/or shaft 1101, as shown.

The above-described embodiments should be understood to serve only as illustrative examples; further embodiments are envisaged. Any feature described herein in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the inventive concepts, which is defined in the accompanying claims.

What is claimed is:

1. A method of treating a patient, comprising:

(a) selecting the patient for treatment;

(b) implanting an implantable device in the patient, wherein the implantable device comprises:

an array of multiple electrodes;

a controller operatively connected to the multiple electrodes; and a memory storage component coupled to the controller, wherein the memory storage component stores instructions for the controller to perform one or more algorithms, wherein during the implanting the multiple electrodes are positioned on an epicardial surface of a heart of the patient proximate a left atrium;

(c) using a first set of the multiple electrodes to sense electrical activity of the heart; and (d) delivering a first configuration of pacing energy to the heart using a second set of the multiple electrodes based on an assessment of the patient's susceptibility to an arrhythmia performed by a first algorithm of the one or more algorithms, wherein the assessment is performed by analyzing the sensed electrical activity;

wherein a second algorithm of the one or more algorithms is configured to determine one or more parameters of the first configuration of pacing energy to be delivered;

wherein the first configuration of pacing energy delivery is configured to minimize susceptibility to initiation of atrial fibrillation in the patient;

wherein the first configuration of pacing energy is delivered to a portion of a cardiac substrate when the portion of the cardiac substrate is determined to be in an excitable state;

wherein a third algorithm of the one or more algorithms is configured to monitor for atrial fibrillation by analyzing the sensed electrical activity; and wherein the delivery of the first configuration of pacing energy is discontinued if atrial fibrillation is detected via the third algorithm.

2. The method according to claim 1, further comprising:

(e) delivering a second configuration of pacing energy to the heart using a third set of the multiple electrodes based on a detection of atrial fibrillation of the patient as determined by a fourth algorithm of the one or more algorithms, wherein the assessment is performed by analyzing the sensed electrical activity;

wherein a fifth algorithm of the one or more algorithms is configured to determine one or more parameters of the second configuration of pacing energy to be delivered; and wherein the second configuration of pacing energy delivery is configured to terminate the atrial fibrillation in the patient.

3. The method according to claim 2, wherein the second set of electrodes and the third set of electrodes comprises the same electrodes of the multiple electrodes.

4. The method according to claim 2, wherein step (e) is performed prior to step (d).

5. The method according to claim 2, wherein the second configuration of pacing energy is based on a complexity assessment of the atrial fibrillation detected.

6. The method according to claim 2, wherein the second configuration of pacing energy is configured to control a fibrillating substrate by deterministically pacing into a narrowed excitable gap present during the atrial fibrillation.

7. The method according to claim 2, wherein a sixth algorithm of the one or more algorithms is configured to identify a restoration of normal rhythm and to terminate the delivery of the second configuration of pacing energy.

8. The method according to claim 2, wherein the first configuration of pacing energy and/or the second configuration of pacing energy is configured to advance and/or block one or more cardiac activation wavefronts.

9. The method according to claim 2, wherein the first configuration of pacing energy and/or the second configuration of pacing energy is delivered ahead of an approaching cardiac activation wavefront.

10. The method according to claim 2, wherein the first configuration of pacing energy and/or the second configuration of pacing energy is configured to synchronize atrial activation.

11. The method according to claim 1, wherein the first configuration of pacing energy comprises a variable rate pacing arrangement.

12. The method according to claim 1, wherein the first configuration of pacing energy comprises pacing that is at least 5%, 10%, or 20% faster than normal sinus rhythm.

13. The method according to claim 1, wherein the second algorithm of the one or more algorithms is further configured to derive a mean and a standard deviation of a heart rate of the patient for a predetermined period, and wherein the first configuration of pacing energy comprises stimuli based on a fractal and/or other nonlinear function that paces the heart at a time that is earlier than a mean-cycle length to impose a variation in heartbeat.

14. The method according to claim 1, wherein the first configuration of pacing energy comprises different durations of earliness corresponding to a heartbeat, and wherein the first configuration of pacing energy is further configured to impose a desired variability in a heart rate over time.

15. The method according to claim 14, wherein the delivering of the first configuration of pacing energy is occasionally inhibited such that the intrinsically-longest cycle length is achieved.

16. The method according to claim 1, wherein the delivering of the first configuration of pacing energy is periodically inhibited, and wherein a mean and a standard deviation of a heart rate is assessed during an inhibition period.

17. The method according to claim 1, further comprising sending an alert to a clinician device when an alert condition is detected.

18. The method according to claim 1, wherein the delivering of a pacing energy is imperceptible to the patient.

19. The method according to claim 1, wherein the patient has atrial fibrillation and HFpEF.

20. The method according to claim 1, wherein the one or more algorithms are configured to detect an excitable state in the cardiac substrate, and wherein the first configuration of pacing energy is delivered during the excitable state of the cardiac substrate.

* * * * *